US011833131B2

(12) United States Patent
Koltai et al.

(10) Patent No.: US 11,833,131 B2
(45) Date of Patent: Dec. 5, 2023

(54) COMPOSITIONS AND METHODS FOR TREATING INFLAMMATORY DISEASES

(71) Applicants: The State of Israel, Ministry of Agriculture & Rural Development, Agricultural Research Organization (ARO) (Volcani Center), Rishion-LeZion (IL); Mor Research Applications Ltd., Tel-Aviv (IL)

(72) Inventors: Hinanit Koltai, Rishon-LeZion (IL); Yoram Kapulnik, Karmey Yosef (IL); Moran Mazuz, Rishon-LeZion (IL); Timna Naftali, Tel-Aviv (IL)

(73) Assignees: The State of Israel, Ministry of Agriculture & Rural Development, Agricultural Research, Rishon-LeZion (IL); Mor Research Applications Ltd., Ramat Gan (IL)

( * ) Notice: Subject to any disclaimer, the term of this patent is extended or adjusted under 35 U.S.C. 154(b) by 165 days.

(21) Appl. No.: 16/491,197

(22) PCT Filed: Mar. 5, 2018

(86) PCT No.: PCT/IL2018/050248
§ 371 (c)(1),
(2) Date: Sep. 5, 2019

(87) PCT Pub. No.: WO2018/163163
PCT Pub. Date: Sep. 13, 2018

(65) Prior Publication Data
US 2020/0222359 A1    Jul. 16, 2020

Related U.S. Application Data

(60) Provisional application No. 62/537,050, filed on Jul. 26, 2017, provisional application No. 62/467,157, filed on Mar. 5, 2017.

(51) Int. Cl.
| *A61K 31/353* | (2006.01) |
| *A61K 31/01* | (2006.01) |
| *A61K 31/015* | (2006.01) |
| *A61K 31/045* | (2006.01) |
| *A61K 31/05* | (2006.01) |
| *A61K 31/12* | (2006.01) |
| *A61K 31/194* | (2006.01) |
| *A61P 1/00* | (2006.01) |
| *A61P 29/00* | (2006.01) |
| *A61K 31/352* | (2006.01) |
| *A61K 36/185* | (2006.01) |
| *A61K 45/06* | (2006.01) |

(52) U.S. Cl.
CPC ............ *A61K 31/353* (2013.01); *A61K 31/01* (2013.01); *A61K 31/015* (2013.01); *A61K 31/045* (2013.01); *A61K 31/05* (2013.01); *A61K 31/12* (2013.01); *A61K 31/194* (2013.01); *A61K 31/352* (2013.01); *A61K 36/185* (2013.01); *A61P 1/00* (2018.01); *A61P 29/00* (2018.01); *A61K 45/06* (2013.01)

(58) Field of Classification Search
CPC .. A61K 2300/00; A61K 31/05; A61K 31/352; A61K 36/185; A61K 45/06; A61K 31/01; A61K 31/015; A61K 31/045; A61K 31/12; A61K 31/194; A61K 31/353; A61P 1/00; A61P 29/00; A61P 35/00
See application file for complete search history.

(56) References Cited

U.S. PATENT DOCUMENTS

| 6,410,588 | B1 | 6/2002 | Feldmann et al. |
| 6,949,582 | B1 | 9/2005 | Wallace |
| 8,980,942 | B2 | 3/2015 | Stinchcomb et al. |
| 9,044,390 | B1 | 6/2015 | Speier |
| 9,730,911 | B2 * | 8/2017 | Verzura .................. A61K 31/05 |
| 2002/0132021 | A1 | 9/2002 | Raskin et al. |
| 2004/0175367 | A1 | 9/2004 | Herlyn et al. |
| 2005/0266108 | A1 | 12/2005 | Flockhart et al. |
| 2007/0032544 | A1 | 2/2007 | Korthout et al. |
| 2009/0197941 | A1 | 8/2009 | Guy et al. |
| 2010/0047853 | A1 | 2/2010 | Kuo et al. |
| 2010/0249223 | A1 | 9/2010 | Di Marzo et al. |
| 2010/0286098 | A1 | 11/2010 | Robson et al. |
| 2012/0128777 | A1 | 5/2012 | Keck et al. |
| 2013/0059018 | A1 | 3/2013 | Parolaro et al. |
| 2013/0122114 | A1 | 5/2013 | Golan et al. |
| 2013/0224151 | A1 | 8/2013 | Pearson et al. |
| 2014/0221469 | A1 | 8/2014 | Ross et al. |
| 2015/0086653 | A1 | 3/2015 | Parolaro et al. |
| 2015/0297654 | A1 | 10/2015 | Speier |
| 2016/0106705 | A1 | 4/2016 | Verzura et al. |
| 2017/0007540 | A1 | 1/2017 | Gupta |
| 2018/0092954 | A1 | 4/2018 | Koltai et al. |
| 2019/0100731 | A1 | 4/2019 | Koltai et al. |
| 2020/0030282 | A1 | 1/2020 | Koltai et al. |

FOREIGN PATENT DOCUMENTS

| CN | 102869356 | 1/2013 |
| EP | 2298283 | 3/2011 |

(Continued)

OTHER PUBLICATIONS

Stancic (The GPR55 antagonist CID 16020046 protects against intestinal inflammation, Neurogastroenterol Motil. Oct. 2015 ; 27(10): 1432-1445, renumbered to pp. 1-28).*

(Continued)

*Primary Examiner* — Kathrien A Hartsfield

(57) ABSTRACT

A method of treating an inflammatory disease in a subject in need thereof is provided. The method comprising administering to the subject a therapeutically effective amount of a liquid chromatography fraction of a cannabis extract comprising at least 75% tetrahydrocannabinolic acid (THCA), wherein the fraction comprises cannabis derived active ingredients other than the THCA.

10 Claims, 26 Drawing Sheets

Specification includes a Sequence Listing.

(56) References Cited

FOREIGN PATENT DOCUMENTS

| | | |
|---|---|---|
| GB | 2393721 | 4/2004 |
| GB | 2527590 | 12/2015 |
| WO | WO 03/061563 | 7/2003 |
| WO | WO 2009/004302 | 1/2009 |
| WO | WO 2011/051947 | 5/2011 |
| WO | WO 2014/159688 | 10/2014 |
| WO | WO 2016/103254 | 6/2016 |
| WO | WO 2016/157192 | 10/2016 |
| WO | WO 2016/179581 | 11/2016 |
| WO | WO 2016/189525 | 12/2016 |
| WO | WO 2017/013661 | 1/2017 |
| WO | WO 2017/158609 | 9/2017 |
| WO | WO 2018/163163 | 9/2018 |
| WO | WO 2018/163164 | 9/2018 |

OTHER PUBLICATIONS

Official Action dated Apr. 16, 2021 from the US Patent and Trademark Office Re. U.S. Appl. No. 16/085,623. (37 pages).
Official Action dated Mar. 24, 2021 From the US Patent and Trademark Office Re. U.S. Appl. No. 16/491,243. (37 Pages).
Restriction Official Action dated Feb. 5, 2021 From the US Patent and Trademark Office Re. U.S. Appl. No. 16/085,623. (10 Pages).
Browning et al. "Organ Culture of Mucosal Biopsies of Human Small Intestine"; The Journal of Clinical Investigation, 48(8): 1423-1432, 1969.
Gracz et al. "Brief Report: CD24 and CD44 Mark Human Intestinal Epithelial Cell Populations with Characteristics of Active and Facultative Stem Cells"; Stem Cells Journals, 31: 2024-2030, 2013.
MedicineNet "Definition of Cancer", MedicineNet.com, downloaded from the internet on Mar. 8, 2011.
Merck KGaA "Millicell Inserts and Plates for Microporous Membrane-Based Cell Culture"; Fisher Scientific, 1-4 pages, 2014.
Reimund et al. "Mucosal Inflammatory Cytokine Production by Intestinal Biopsies in Patients with Ulcerative Colitis and Crohn's Disease"; Journal of Clinical Immunology, 16(3): 144-150, 1996.
International Preliminary Report on Patentability dated Nov. 9, 2017 From the International Bureau of WIPO Re. Application No. PCT/IL2016/050348. (8 Pages) Correction.
International Preliminary Report on Patentability dated Oct. 12, 2017 From the International Bureau of WIPO Re. Application No. PCT/IL2016/050348. (8 Pages).
International Preliminary Report on Patentability dated Sep. 27, 2018 From the International Bureau of WIPO Re. Application No. PCT/IL2017/050338. (7 Pages).
International Search Report and the Written Opinion dated Jul. 7, 2016 From the International Searching Authority Re. Application No. PCT/IL2016/050348.
International Search Report and the Written Opinion dated Jun. 7, 2018 From the International Searching Authority Re. Application No. PCT/ IL2018/050248. (17 Pages).
International Search Report and the Written Opinion dated Jun. 17, 2018 From the International Searching Authority Re. Application No. PCT/IL2018/050249. (15 Pages).
International Search Report and the Written Opinion dated Jun. 26, 2017 From the International Searching Authority Re. Application No. PCT/IL2017/050338. (10 Pages).
Office Action dated Jun. 13, 2019 From the Israel Patent Office Re. Application No. 61847 and Its Translation Into English. (5 Pages).
Supplementary European Search Report and the European Search Opinion dated Nov. 6, 2018 From the European Patent Office Re. Application No. 16771541.6. (8 Pages).
Supplementary European Search Report and the European Search Opinion dated Sep. 26, 2019 From the European Patent Office Re. Application No. 17765995.0. (12 Pages).
Aizpurua-Olaizola et al. "Evolution of the Cannabinoid and Terpene Content During the Growth of Cannabis Sativa Plants From Different Chemotypes", Journal of Natural Products, 79(2): 324-331, Feb. 2, 2016.
Aviello et al. "Chemopreventive Effect of the Non-Psychotropic Phytocannabinoid Cannabidiol on Experimental Colon Cancer", Journal of Molecular Medicine, 90(8): 925-934, Published Online Jan. 10, 2012.
Ben-Shabat et al. "An Entourage Effect: Inactive Endogenous Fatty Acid Glycerol Esters Enhance 2-Arachidonoyl-Glycerol Cannabinoid Activity", European Journal of Pharmacology, 353(1): 23-31, Jul. 17, 1998.
Borrelli et al. "Colon Carcinogenesis Is Inhibited by the TRPM8 Antagonist Cannabigerol, A Cannabis-Derived Non-Psychotropic Cannabinoid", Carcinogenesis, 35(12): 2787-2797, Advance Access Publication Sep. 30, 2014.
Colbert "Cannabinoid Profile: Tetrahydrocannabinolic Acid (THCa)", TheLeafOnline, 5 P., Jul. 15, 2014.
Danin "Erodium Crassifolium, Erodium Hirtum, Hoary-Leaved Heron's-Bill", Flowers of Israel, XP009506767, Retrieved From the Internet, p. 1-3, Aug. 8, 2014.
De Filippis et al. "Cannabidiol Reduces Intestinal Inflammation Through the Control of Neuroimmune Axis". PLoS ONE, 6(12): e28159-1-e28159-9, Dec. 6, 2011. Figs.5-8.
De Graaf et al. "Preparation and Incubation of Precision-Cut Liver and Intestinal Slices for Application in Drug Metabolism and Toxicity Studies", Nature Protocols, 5(9): 1540-1551. Published Online Aug. 19, 2010.
De Kanter et al. "Precision-Cut Organ Slices as A Tool to Study Toxicity and Metabolism of Xenobiotics With Special Reference to Non-Hepatic Tissues", Current Drug Metabolism, 3(1): 39-59, Feb. 2002.
D'Haens et al. "Future Directions in Inflammatory Bowel Disease Management", Journal of Crohn's and Colitis, 8(8): 726-734, Aug. 2014.
ElSohly et al. "Phytochemistry of *Cannabis sativa* L.", Progress in the Chemistry of Organic Natural Products: Phytocannabinoids. Pogrchem, 103: 1-36, Published Online Jan. 25, 2017.
Evans et al. "The Development of A Method for the Preparation of Rat Intestinal Epithelial Cell Primary Cultures", Journal of Cell Science, XP009006507, 101(1): 219-231, Jan. 31, 1992. Abstract, Figs.1, 2, Table 1, p. 222, Left col. Para 5, p. 228, Left col. 1st Para.
Gohar et al. "Antibacterial Polyphenol From Erodium Glaucophyllum", Zeitung fuer Naturforschung, 58(9-10): 670-674, Sep.-Oct. 2003. p. 670, 672-673.
Greenhough et al. "The Cannabinoid [Delta]9-Tetrahydrocannabinol Inhibits RAS-MAPK and PI3K-AKT Survival Signalling and Induces BAD-Mediated Apoptosis in Colorectal Cancer Cells", International Journal of Cancer, 121(10): 2172-2180, Published Online Jun. 21, 2007.
Greineisen et al. "Immunoactive Effects of Cannabinoids: Considerations for the Therapeutic Use of Cannabinoid Receptor Agonists and Antagonists", International Immunopharmacology, 10(5): 547-555, May 2010.
Harvey et al. "Interleukin 17A Evoked Mucosal Damage is Attenuated by Cannabidiol and Anandamide in A Human Colonic Explant Model", Cytokine, XP055602795, 65(2): 236-244, Available Online Nov. 13, 2013. p. 239, Left col. 1st Para, p. 243, Left col. 3rd Para, Figs.1, 2.
Hill et al. "Cannabidivarin-Rich Cannabis Extracts Are Anticonvulsant in Mouse and Rat Via A CB1 Receptor-Independent Mechanism", British Journal of Pharmacology, 170(3): 679-692, Oct. 2013.
Ihenetu et al. "Inhibition of Interleukin-8 Release in the Human Colonic Epithelial Cell Line HT-29 by Cannabinoids", European Journal of Pharmacology, 458(1-2): 207-215, Jan. 2003.
Izzo et al. "Cannabinoids is an Intestinal Inflammation and Cancer", Pharmacological Research, 60(2): 117-125, Aug. 2009.
Javid et al. "Cannabinoid Pharmacology in Cancer Research: A New Hope for Cancer Patients?", European Journal of Pharmacology, 775: 1-4, Mar. 15, 2016.
Kauffman et al. "Alternative Functional In Vitro Models of Human Intestinal Epithelia", Frontiers in Pharmacology, XP055503086, 4(Art.79): 1-18, Published Online Jul. 8, 2013.
MatTek Corporation "EpiIntestinal™", Overiew, MatTek Corporation, 8 P., 2017.

(56) References Cited

OTHER PUBLICATIONS

Mechoulam et al. "Cannabidiol: An Overview of Some Pharmacological Aspects", The Journal of Clinical Pharmacology, 42(S1): 11S-19S, Nov. 2002.
Mechoulam et al. "Chemical Basis of Hashish Activity", Science, 169(3945): 611-612, Aug. 7, 1970.
Mechoulam et al. "Hashish—IV: The Isolation and Structure of Cannabinolic Cannabidiolic and Cannabigerolic Acids", Tetrahedron, 21(5): 1223-1229, Jan. 1965.
Naftali et al. "Cannabis Induces A Clinical Response in Patients With Crohn's Disease: A Prospective Placebo-Controlled Study", Clinical Gastroenterology and Hepatology, 11(10): 1276-1280, Oct. 2013.
Naftali et al. "Treatment of Crohn's Disease With Cannabis: An Observational Study", The Israel Medical Association Journal, IMAJ, 13(8): 455-458, Aug. 2011.
Pagano et al. "An Orally Active Cannabis Extract With High Content in Cannabidiol Attenuates Chemically-Induced Intestinal Inflammation and Hypermotility in the Mouse", Frontiers in Pharmacology, 7(Art.341): 1-12, Oct. 4, 2016.
Pageot et al. "Human Cell Models to Study Small Intestinal Functions: Recapitulation of the Crypt-Villus Axis", Microscopy Research and Technique, XP055622386, 49(4): 394-406, May 15, 2000.
Perera et al. "Immunomodulatory Activity of A Chinese Herbal Drug Yi Shen Juan Bi in Adjuvant Arthritis", Indian Journal of Pharmacology, XP055517710, 42(2): 65-69, Apr. 2010.
Romano et al. "Inhibition of Colon Carcinogenesis by A Standarized *Cannabis sativa* Extract With High Content of Cannabidiol", Phytomedicine, 21(5): 631-639, Apr. 15, 2014.
Romano et al. "Pure [Delta]9-Tetrahydrocannabivarin and A *Cannabis sativa* Extract With High Content in [Delta]9-Tetrahydrocannabivarin Inhibit Nitrite Production in Murine Peritoneal Macrophages", Pharmacological Research, 113: 199-208, Available Online Aug. 3, 2016.
Russo et al. "Taming THC: Potential Cannabis Synergy and Phytocannabinoid-Terpenoid Entourage Effects", British Journal of Pharmacology, 163(7): 1344-1364, Aug. 2011.
Ryberg et al. "The Orphan Receptor GPR55 is A Novel Cannabinoid Receptor", British Journal of Pharmacology, 152(7): 1092-1101, Published Online Sep. 17, 2007.
Sartor "Mechanisms of Disease: Pathogenesis of Crohn's Disease and Ulcerative Colitis", Nature Clinical Practice Gastroenterology & Hepatology, 3(7): 390-407, Jul. 2006.
Sato et al. "Long-Term Expansion of Epithelial Organoids From Human Colon, Adenoma, Adenocarcinoma, and Barrett's Epithelium", Gastroenterology, XP028325676, 141(5): 1762-1772, Published Online Jul. 27, 2011. p. 1763, Left col. 5th Para, Right col. Para 1-2, p. 1764, Right col. 3rd Para, p. 1765, Left col. 2nd Para, Fig. 1.
Schicho et al. "Cannabis Finds Its Way Into Treatment of Crohn's Disease", Pharmacology, 93(1-2): 1-3, Published Online Dec. 17, 2013.
Sroka et al. "Antioxidative Effect of Extracts From *Erodium cicutarium* L.", Zeitung fuer Naturforschung, XP055319445, 49(11-12): 881-884, Nov.-Dec. 1994.
Stancic et al. "The GPR55 Antagonist CID16020046 Protects Against Intestinal Inflammation", Neurogastroenterology & Motility, 27(10): 1432-1445, Oct. 2015.

Storr et al. "Activation of the Cannabinoid 2 Receptor (CB2) Protects Against Experimental Colitis", Inflammation Bowel Disease, 15(11): 1678-1685. Published Online Apr. 30, 2009.
Sturm et al. "Epithelial Restitution and Wound Healing in Inflammatory Bowel Disease", World Journal of Gastroenterology, 14(3): 348-353, Jan. 21, 2008.
Wright et al. "Cannabinoid CB2 Receptors in the Gastrointestinal Tract: A Regulatory System in States of Inflammation". British Journal of Pharmacology, 153(2): 263-270, Published Online Oct. 1, 2007.
Office Action dated Nov. 10, 2020 From the Israel Patent Office Re. Application No. 261847 and Its Translation Into English. (5 Pages).
Restriction Official Action dated Nov. 5, 2020 from the US Patent and Trademark Office Re. U.S. Appl. No. 16/491,243. (11 pages).
English Summary dated May 17, 2022 of Notification of Office Action and Search Report dated May 7, 2022 From the State Intellectual Property Office of the People's Republic of China Re. Application No. 201880029756.5. (1 Page).
Final Official Action dated Dec. 15, 2021 from US Patent and Trademark Office Re. U.S. Appl. No. 16/085,623. (21 pages).
Notice of Allowance dated Jan. 21, 2022 from US Patent and Trademark Office Re. U.S. Appl. No. 16/491,243. (10 pages).
Notice of Allowance dated Sep. 23, 2021 from the US Patent and Trademark Office Re. U.S. Appl. No. 16/491,243. (12 pages).
Notification of Office Action and Search Report dated May 7, 2022 From the State Intellectual Property Office of the People's Republic of China Re. Application No. 201880029756.5. (9 Pages).
Notification of Office Action and Search Report dated Jun. 22, 2022 From the State Intellectual Property Office of the People's Republic of China Re. Application No. 201880026618.1 and its Summary in English. (15 Pages).
Office Action dated Jan. 4, 2022 From the Israel Patent Office Re. Application No. 269158. (4 Pages).
Office Action dated Dec. 20, 2021 From the Israel Patent Office Re. Application No. 261847 and Its Translation Into English. (5 Pages).
Office Action dated Dec. 28, 2021 From the Israel Patent Office Re. Application No. 269157 and Its Translation Into English. (7 Pages).
Supplementary European Search Report and the European Search Opinion dated Dec. 2, 2020 From the European Patent Office Re. Application No. 18764952.0. (12 Pages).
Supplementary European Search Report and the European Search Opinion dated Nov. 26, 2020 From the European Patent Office Re. Application No. 18764840.7. (12 Pages).
Moreno-Sanz "Can You Pass the Acid Test? Critical Review and Novel Therapeutic Perspectives of Delta9-Tetrahydrocannabinolic Acid A", Cannabis and Cannabinoid Research, XP055633812, 1(1): 124-130, Published Online Jun. 1, 2016.
Naftali et al. "Cannabis for Inflammatory Bowel Disease", Digestive Diseases, XP009524112, 32(4): 468-474, Jun. 23, 2014.
Nallathambi et al. "Anti-Inflammatory Activity in Colon Models is Derived From Delta9-Tetrahydrocannabinolic Acid That Interacts With Additional Compounds in Cannabis Extracts", Cannabis and Cannabinoid Research, XP055751236, 2(1): 167-182, Jul. 1, 2017.
Ruhaak et al. "Evaluation of the Cyclooxygenase Inhibiting Effects of Six Major Cannabinoids Isolated From *Cannabis sativa*", Biological & Pharmaceutical Bulletin, XP055622634, 34(5): 774-778, Published Online Feb. 28, 2011.
Sigma-Aldaich "Product Specification: Colagenase from Clostridium Histolyticum—Release of Physiologically Active Rat Pancreatic Islets Tested, type XI, 2-5, FALGPA Units/mg Solid. Z800 CDU/mg Solid", Sigma-Aldaich, 1, 2021.
Unknwon "Collagenase Type I", Millipore Sigma, 1-4, 2021.

\* cited by examiner

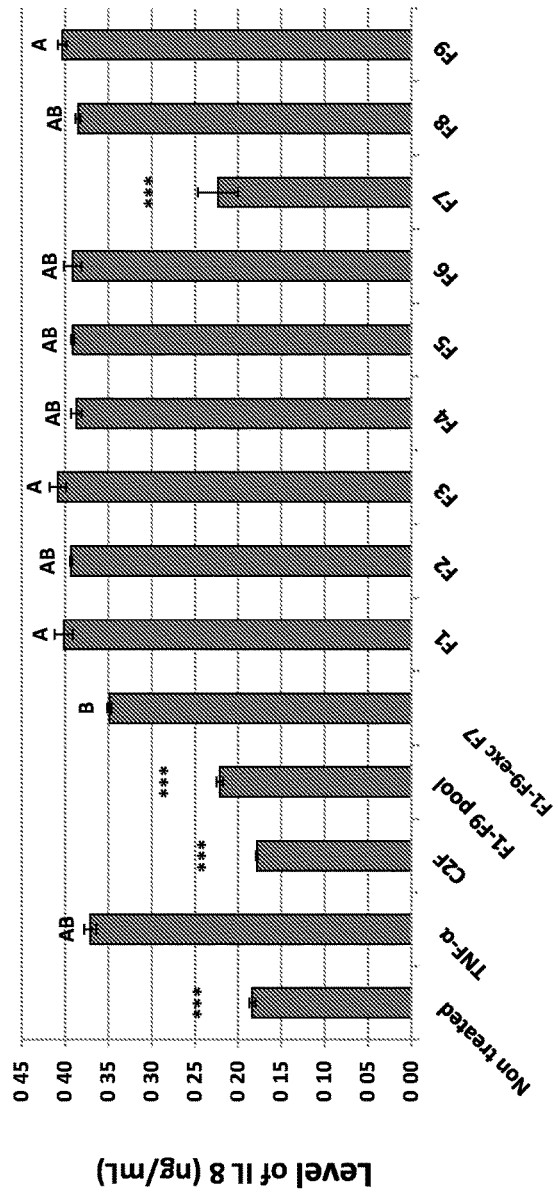
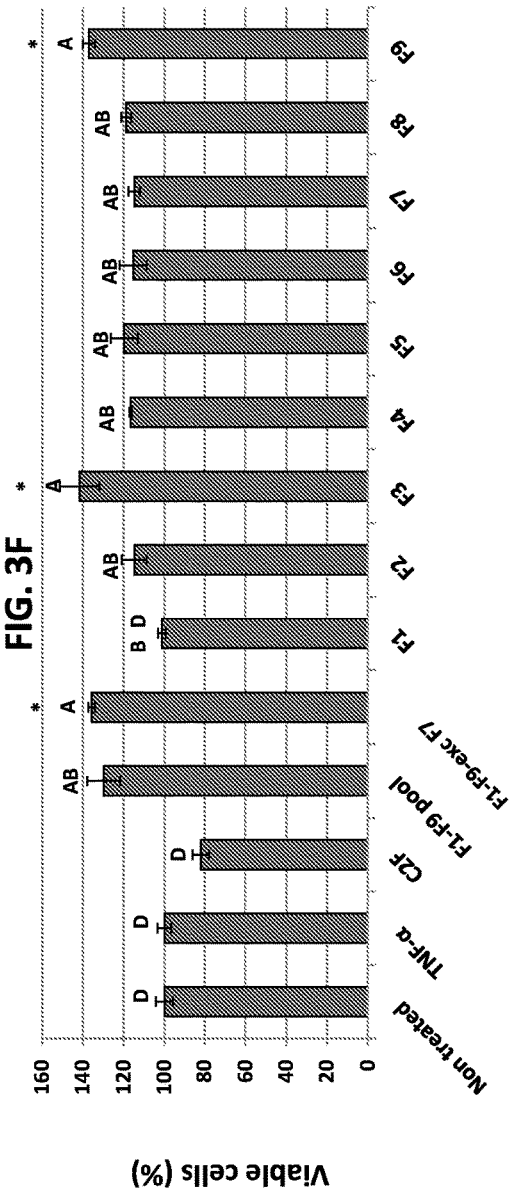
FIG. 3E
FIG. 3F

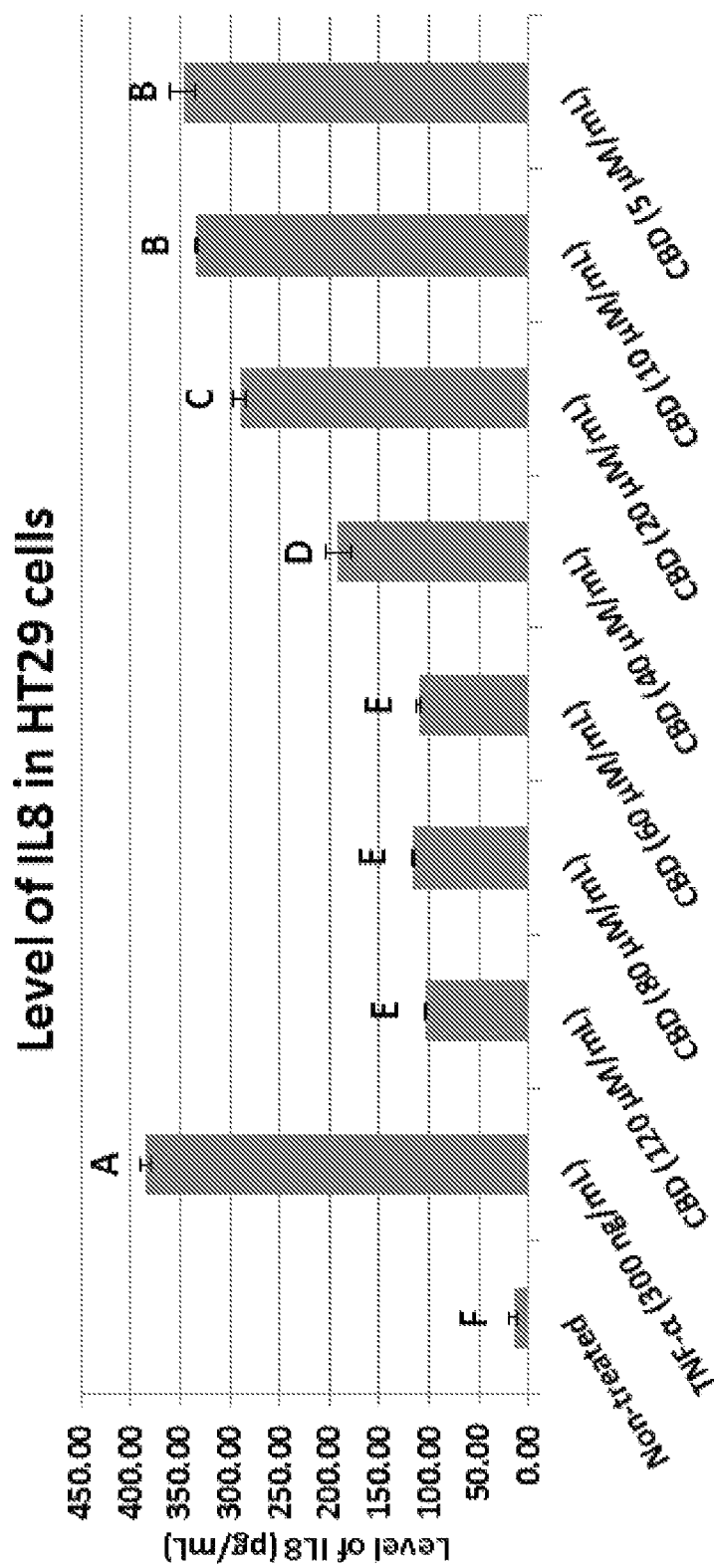

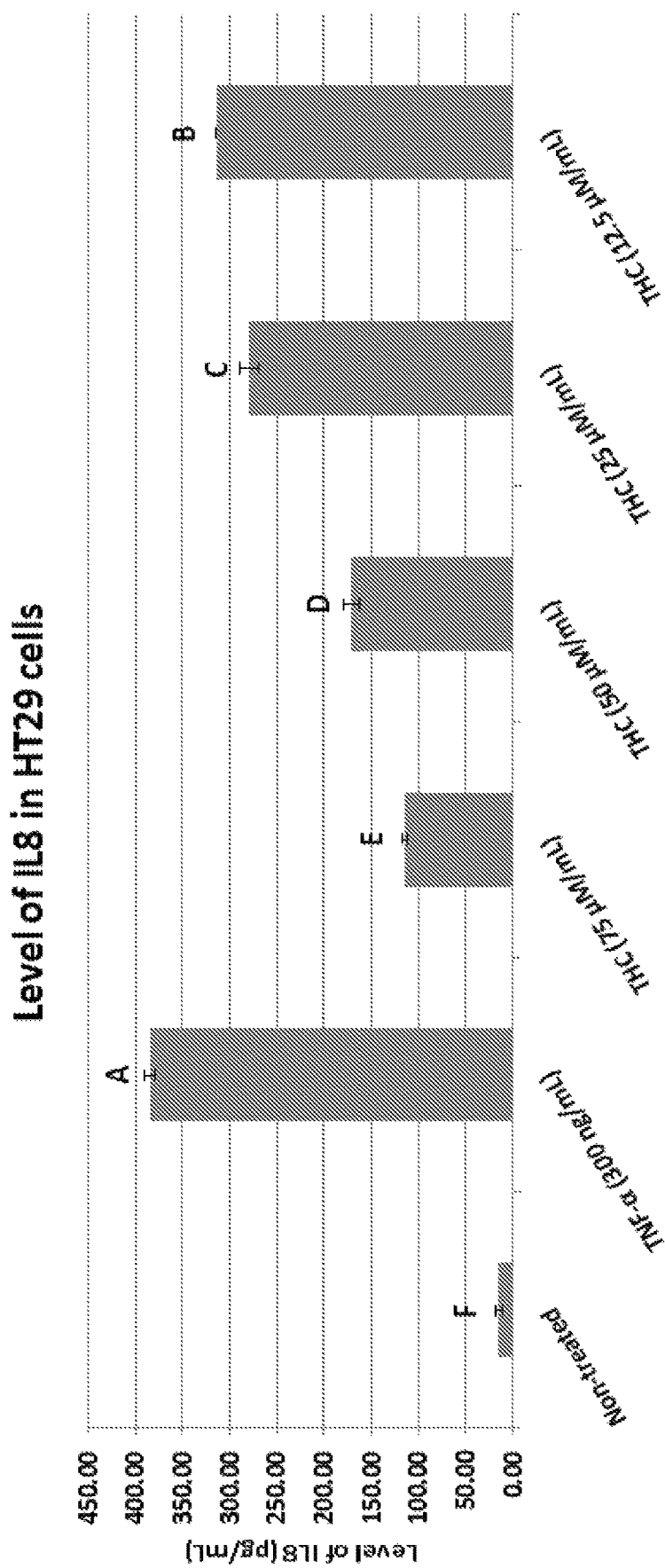

COMPOSITIONS AND METHODS FOR TREATING INFLAMMATORY DISEASES

RELATED APPLICATIONS

This application is a National Phase of PCT Patent Application No. PCT/IL2018/050248 having International filing date of Mar. 5, 2018, which claims the benefit of priority under 35 USC § 119(e) of U.S. Provisional Patent Application Nos. 62/537,050 filed on Jul. 26, 2017 and 62/467,157, filed on Mar. 5, 2017. The contents of the above applications are all incorporated by reference as if fully set forth herein in their entirety.

SEQUENCE LISTING STATEMENT

The ASCII file, entitled 79363SequenceListing.txt, created on 2019, 5 Sep., comprising 1,365 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to compositions and methods for the treatments of inflammatory diseases.

Several human diseases are inflammatory in nature, including asthma, Crohn's disease, rheumatoid arthritis, polymyalgia rheumatica, tendonitis, bursitis, laryngitis, gingivitis, gastritis, otitis, celiac disease, diverticulitis, and inflammatory bowel disease. Additionally, a number of chronic diseases have inflammatory components, such as atherosclerosis, obesity, diabetes mellitus, cancer, and perhaps even Alzheimer's disease.

Inflammatory bowel diseases (IBDs), Crohn's disease (CD) and ulcerative colitis (UC) are characterized by chronic intestinal inflammation. Both diseases are chronic, relapsing and associated with different genetic predisposing backgrounds. Their onset and reactivation are triggered by environmental factors which transiently break the mucosal barrier. This may alter the balance between beneficial and pathogenic enteric bacteria and consequently stimulate immune responses. Both CD and UC patients have activated innate (macrophage, neutrophil) and acquired (T and B cell) immune responses (e.g., [1]).

Epithelial cells in the gastrointestinal (GI) tract act as barriers against the intrusion of potentially deleterious luminal substances and microorganisms from the intestinal lumen, and play an important role in inflammatory responses. They express a variety of pro-inflammatory cytokines, which are upregulated in IBD patients [2]. Therapies aimed at down-regulating intestinal inflammation utilize both mediator-specific and nonspecific immune suppression, but with potentially considerable side effects [3].

Different preparations of marijuana (Cannabis sativa) have been used for the treatment of GI problems, such as GI pain, gastroenteritis and diarrhea [4,5]. C. sativa contains more than 60 terpenophenolic compounds termed phytocannabinoids (reviewed by [6]). Of these, Δ9-tetrahydrocannabinol (THC) and cannabidiol (CBD), which were discovered about 50 years ago, have been defined as the most active [7-9]. Cannabinoids have been previously shown to be immune modulators. They shift the balance of pro- and anti-inflammatory cytokines and act to suppress cell-mediated immunity in different physiological systems [10]. For example, Δ9-tetrahydrocannabivarin (THCV) was demonstrated to inhibit nitrite production in macrophages and thereby to play an immunomodulatory role [11].

Cannabinoids derived from Cannabis sativa (Phytocannabinoids) have been shown to exert their biological functions on the GI tract by mainly activating two types of G-protein-coupled cannabinoid receptors: cannabinoid type 1 (CB1) and cannabinoid type 2 (CB2) [4, 12]. Later, a third cannabinoid receptor, GPR55, was identified [13]. These receptors are part of the endocannabinoid system in the GI tract [13,14].

Cannabinoids have been shown to be effective in a mouse model of colitis [15]. In the human colonic epithelial cell line HT29, a number of cannabinoid receptor agonists and antagonists, including the plant-derived THC, have been shown to inhibit tumor necrosis factor alpha (TNF-α)-induced interleukin-8 (IL-8) release [12]. This inhibition was antagonized by a CB2 receptor antagonist. Cannabinoids have also been shown to promote wound healing in the GI tract via CB1 receptor activation [4,16]. In addition, we have recently reported clinical data from IBD patients. In a retrospective study we interviewed 30 CD patients who were licensed to use medical cannabis [17], while in a prospective trial we randomized 20 CD patients to receive either cannabis or placebo for their IBD [18]. Both revealed beneficial effects.

C. sativa extracts contain hundreds of different compounds. The activity of many synthetic or isolated cannabinoids and their receptor agonists or antagonists have been investigated and verified. However, there seems to be an advantage of the unrefined content of the flower versus an isolated compound in IBD. For example, standardized Cannabis sativa extract with high content of cannabidiol (CBD) was shown in animal model of GI inflammation to attenuate injury and motility, once given after the inflammatory insult, further sustaining the rationale of combining CBD with other minor Cannabis constituents [19]. Also, cannabis-derived botanical drug substances exerted significant anti-convulsant effects in three models of seizure and were of comparable efficacy with purified cannabidivarin (CBDV) [20].

Additional background art includes:

U.S. Pat. Appls. 20160106705, 20100249223, 20130059018, 20140221469 www(dot)//theleafonline(dot)com/c/science/2014/07/cannabinoid-profile-crash-course-thca/

SUMMARY OF THE INVENTION

According to an aspect of some embodiments of the present invention there is provided a method of treating an inflammatory disease in a subject in need thereof, the method comprising administering to the subject a therapeutically effective amount of a liquid chromatography fraction of a cannabis extract comprising at least 75% tetrahydrocannabinolic acid (THCA), wherein the fraction comprises cannabis derived active ingredients other than the THCA, thereby treating the inflammatory disease in the subject.

According to an aspect of some embodiments of the present invention there is provided a therapeutically effective amount of a liquid chromatography fraction of a cannabis extract comprising at least 75% tetrahydrocannabinolic acid (THCA), wherein the fraction comprises cannabis derived active ingredients other than the THCA, for use in treating an inflammatory disease in a subject in need thereof.

According to an aspect of some embodiments of the present invention there is provided a method of treating an inflammatory disease in a subject in need thereof, the method comprising administering to the subject a composition of matter comprising a therapeutically effective amount of liquid chromatography pooled fractions of cannabis extract comprising active ingredients detectable by a detector operated at 220 nm, wherein the active ingredients comprise THCA, thereby treating the inflammatory disease in the subject.

According to an aspect of some embodiments of the present invention there is provided a therapeutically effective amount of liquid chromatography pooled fractions of cannabis extract comprising active ingredients detectable by a detector operated at 220 nm, wherein the active ingredients comprise THCA, for use in treating an inflammatory disease in a subject in need thereof.

According to an aspect of some embodiments of the present invention there is provided a method of treating an inflammatory disease in a subject in need thereof, the method comprising administering to the subject a therapeutically effective amount of a composition comprising tetrahydrocannabinolic acid (THCA), wherein the THCA constitutes at least 30% of the active ingredients in the composition, thereby treating the inflammatory disease in the subject.

According to an aspect of some embodiments of the present invention there is provided a therapeutically effective amount tetrahydrocannabinolic acid (THCA) for use in treating an inflammatory disease in a subject in need thereof, wherein the THCA constitutes at least 30% of the active ingredients in the composition.

According to an aspect of some embodiments of the present invention there is provided a composition comprising liquid chromatography pooled fractions of cannabis extract comprising active ingredients detectable by a detector operated at 220 nm, the active ingredients comprising THCA.

According to an aspect of some embodiments of the present invention there is provided a composition comprising liquid chromatography-purified cannabis fraction obtainable by subjecting the cannabis extract to liquid chromatography and collecting fractions detectable by a detector operated at 220 nm.

According to an aspect of some embodiments of the present invention there is provided a composition comprising liquid chromatography pooled fractions of cannabis extract comprising active ingredients detectable by a detector operated at 220 nm, the composition being characterized by: (i) having a cytotoxic activity on cancer cells; (ii) reducing the level of pro-inflammatory cytokine secretion by cells; and/or (iii) reducing the level of MMP9 and COX2 expression in cells.

According to an aspect of some embodiments of the present invention there is provided a composition comprising THCA and CBD, wherein the composition is devoid of at least one of cannabichromene (CBC), cannabigerolic acid (CBGA), cannabidiolic acid (CBDA), cannabigerol (CBG) and/or cannabinol (CBN).

According to an aspect of some embodiments of the present invention there is provided a method of treating an inflammatory disease in a subject in need thereof, the method comprising administering to the subject a therapeutically effective amount of the composition of some embodiments of the invention, thereby treating the inflammatory disease in the subject.

According to an aspect of some embodiments of the present invention there is provided a therapeutically effective amount of the composition of some embodiments of the invention for use in treating an inflammatory disease in a subject in need thereof.

According to an aspect of some embodiments of the present invention there is provided a method of generating an anti-inflammatory composition, the method comprising: (i) adding a polar solvent to a dry Cannabis inflorescence so as to obtain a crude extract; (ii) filtering the crude extract so as to obtain a filtered extract; (iii) fractionating the filtered extract on a high pressure liquid chromatography (HPLC); (iv) collecting at least one fraction comprising active ingredients detectable by a detector operated at 220 nm.

According to an aspect of some embodiments of the present invention there is provided an anti-inflammatory composition obtainable by the method of some embodiments of the invention.

According to an aspect of some embodiments of the present invention there is provided a method of treating an inflammatory disease in a subject in need thereof, the method comprising administering to the subject a therapeutically effective amount of the composition of some embodiments of the invention, thereby treating the inflammatory disease in the subject.

According to an aspect of some embodiments of the present invention there is provided a therapeutically effective amount of the composition of some embodiments of the invention for use in treating an inflammatory disease in a subject in need thereof.

According to an aspect of some embodiments of the present invention there is provided a method of determining an anti-inflammatory activity of the composition of any one of some embodiments of the invention, the method comprising ex-vivo contacting an inflamed tissue of a subject with the composition, wherein an increased anti-inflammatory response of the inflamed tissue above a predetermined threshold is indicative of the anti-inflammatory activity of the composition.

According to some embodiments of the invention, the composition comprises THCA.

According to some embodiments of the invention, the composition comprises at least 75% THCA.

According to some embodiments of the invention, the composition comprises at least one of D-Limonene, β-Caryophyllene, Humulene, malic acid, α-Farnesene, cannabinol (CBN), Δ9-tetrahydrocannabinol (THC), and/or cannabigerol (CBG).

According to some embodiments of the invention, the composition comprises D-Limonene, β-Caryophyllene, Humulene, malic acid, α-Farnesene, cannabinol (CBN), Δ9-tetrahydrocannabinol (THC), and cannabigerol (CBG).

According to some embodiments of the invention, the composition comprises at least one of the components listed in Table 6.

According to some embodiments of the invention, the composition is characterized by: (i) having a cytotoxic activity on cancer cells (ii) reducing the level of pro-inflammatory cytokine secretion by cells; and/or (ii) reducing the level of MMP9 and COX2 expression in cells.

According to some embodiments of the invention, the composition comprises CBD.

According to some embodiments of the invention, the method further comprises administering to the subject a therapeutically effective amount of cannabidiol (CBD).

According to some embodiments of the invention, the fraction, THCA or composition for use further comprises the use of a therapeutically effective amount of cannabidiol (CBD).

According to some embodiments of the invention, the method further comprises administering to the subject an agonist of CB1 receptor, CB2 receptor and/or GPR55.

According to some embodiments of the invention, the fraction, THCA or composition for use further comprises the use of an agonist of CB1 receptor, CB2 receptor and/or GPR55.

According to some embodiments of the invention, the THCA comprises a synthetic THCA or analog thereof having an anti-inflammatory activity.

According to some embodiments of the invention, the THCA comprises a liquid chromatography fraction of a cannabis extract, the fraction comprising at least 75% tetrahydrocannabinolic acid (THCA), wherein the fraction comprises cannabis derived active ingredients other than the THCA.

According to some embodiments of the invention, the cannabis extract comprises about 80-95% THCA.

According to some embodiments of the invention, the fraction or fractions comprise at least one of D-Limonene, β-Caryophyllene, Humulene, malic acid, α-Farnesene, cannabinol (CBN), Δ9-tetrahydrocannabinol (THC), and/or cannabigerol (CBG).

According to some embodiments of the invention, the fraction or fractions comprises at least two of the D-Limonene, β-Caryophyllene, Humulene, malic acid, α-Farnesene, cannabinol (CBN), Δ9-tetrahydrocannabinol (THC), and/or cannabigerol (CBG).

According to some embodiments of the invention, the fraction or fractions comprises components as listed in Table 6.

According to some embodiments of the invention, the CBD comprises a synthetic CBD or analog thereof having an anti-inflammatory activity.

According to some embodiments of the invention, the inflammatory disease is an inflammatory bowel disease (IBD).

According to some embodiments of the invention, the IBD is selected from the group consisting of ulcerative colitis and Crohn's disease.

According to some embodiments of the invention, the subject is a human subject.

According to some embodiments of the invention, the liquid chromatography comprises high pressure liquid chromatography (HPLC).

According to some embodiments of the invention, the liquid chromatography is performed on a reverse stationary phase.

According to some embodiments of the invention, the liquid chromatography is performed using a mobile phase comprising from 10 to 30% acidic aqueous solution and from 90 to 70% alcohol.

According to some embodiments of the invention, the HPLC comprises a stationary phase comprising RP-18 end capped column, and a mobile phase of 15% solvent A (0.1% acetic acid in water) and 85% solvent B (methanol) at a flow rate of 1.5 mL/min for 28-35 minutes.

According to some embodiments of the invention, the conditions for the HPLC comprise an UltiMate 3000 HPLC system coupled with WPS-3000(T) Autosampler, HPG-3400 pump, and DAD-300 detector, a Purospher RP-18 end capped column a mobile phase of 15% solvent A (0.1% acetic acid in water) and 85% solvent B (methanol) at a flow rate of 1.5 mL/min for 28-35 minutes.

According to some embodiments of the invention, the detector is a diode array detector.

According to some embodiments of the invention, the at least one fraction comprises THCA.

According to some embodiments of the invention, the at least one fraction comprises at least 75% THCA.

According to some embodiments of the invention, the at least one fraction comprises at least one of D-Limonene, β-Caryophyllene, Humulene, malic acid, α-Farnesene, cannabinol (CBN), Δ9-tetrahydrocannabinol (THC), and/or cannabigerol (CBG).

According to some embodiments of the invention, the at least one fraction comprises components as listed in Table 6.

According to some embodiments of the invention, the HPLC comprises a stationary phase comprising RP-18 end capped column, and a mobile phase of 15% solvent A (0.1% acetic acid in water) and 85% solvent B (methanol) at a flow rate of 1.5 mL/min for 28-35 minutes.

According to some embodiments of the invention, the conditions for the HPLC comprise an UltiMate 3000 HPLC system coupled with WPS-3000(T) Autosampler, HPG-3400 pump, and DAD-300 detector, a Purospher RP-18 end capped column a mobile phase of 15% solvent A (0.1% acetic acid in water) and 85% solvent B (methanol) at a flow rate of 1.5 mL/min for 28-35 minutes.

According to some embodiments of the invention, the detector is a diode array detector.

According to some embodiments of the invention, the inflamed tissue is a gastrointestinal tissue biopsy.

According to some embodiments of the invention, the anti-inflammatory activity of the composition comprises an upregulation in secretion of an anti-inflammatory factor and/or reduction in secretion of a pro-inflammatory factor.

According to some embodiments of the invention, the anti-inflammatory activity of the composition comprises reduction in expression of a gene associated with the inflammation.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-D depict (FIG. 1A) Determination of HCT116 cell viability using Alamar Blue fluorescence (Resazurin assay) as a function of cell number. HCT116 cells were seeded (50,000 per well) in triplicate in 500 μL growing media and incubated for 24 hours at 37° C. in a humidified 5% $CO_2$-95% air atmosphere. Cells were treated with 50 ng/mL TNF-α and *C. sativa* ethanolic extracts of fresh (C2F, 0.2 mg/mL) or baked (C2B, 0.2 mg/mL) cannabis flowers, 20 μM dexamethasone for 16 hours. Following, the cells were incubated with Alamar Blue for 4 hours. Relative fluorescence at the excitation/emission of 544/590 nm was measured. Values were calculated as percentage of live cells relative to the non-treated (cells without TNF-α and treatments) control after reducing the auto fluorescence of Alamar Blue without cells (n=3). (FIG. 1B) Anti-inflammatory activity of *C. sativa* ethanolic extracts 0.2 mg/mL C2F, 0.2 mg/mL C2B, and 20 μM dexamethasone, measured as level of IL-8 on HCT116 cells. Cells were seeded and treated as described in (FIG. 1A) and IL-8 values were measured from the supernatant using a commercial kit. Values (ng/mL) were calculated relative to a TNF-α-treated control. Non-treated are the cells without TNF-α and treatments. Error bars indicate±SEM (n=3). *, , * indicates data statistically significantly different in comparison with the control (TNF-α treated cells) at $p≤0.05$, $p≤0.001$, $p≤0.0001$, respectively. Levels with different letters are significantly different from all combinations of pairs by turkey HSD. (FIGS. 1C-D) Dose-effect curves of *C. sativa* ethanolic extracts of fresh (C2F) and baked (C2B) flowers at different dilution range from 1 mg/ml to 0.07 mg/ml of crude extract on viability of HCT-116 colon cancer cells, determined by Alamar Blue fluorescence (Resazurin assay). HCT116 cells were seeded (50,000 per well) in triplicate in 500 μL, growing media and incubated for 24 hours at 37° C. in a humidified 5% $CO_2$-95% air atmosphere. Cells were treated with 50 ng/mL TNF-α and C2F, C2B for 16 hours. Following, the cells were incubated with Alamar Blue for 4 hours. Relative fluorescence at the excitation/emission of 544/590 nm was measured. Values were calculated as percentage of live cells relative to the non-treated (cells without TNF-α and treatments) control after reducing the auto fluorescence of Alamar Blue without cells (n=3). For dose response assays, data points were connected by non-linear regression lines of the sigmoidal dose-response relation. GraphPad Prism was employed to produce dose-response curve and $IC_{50}$ doses for C2F and C2B extracts.

Figure 1A:
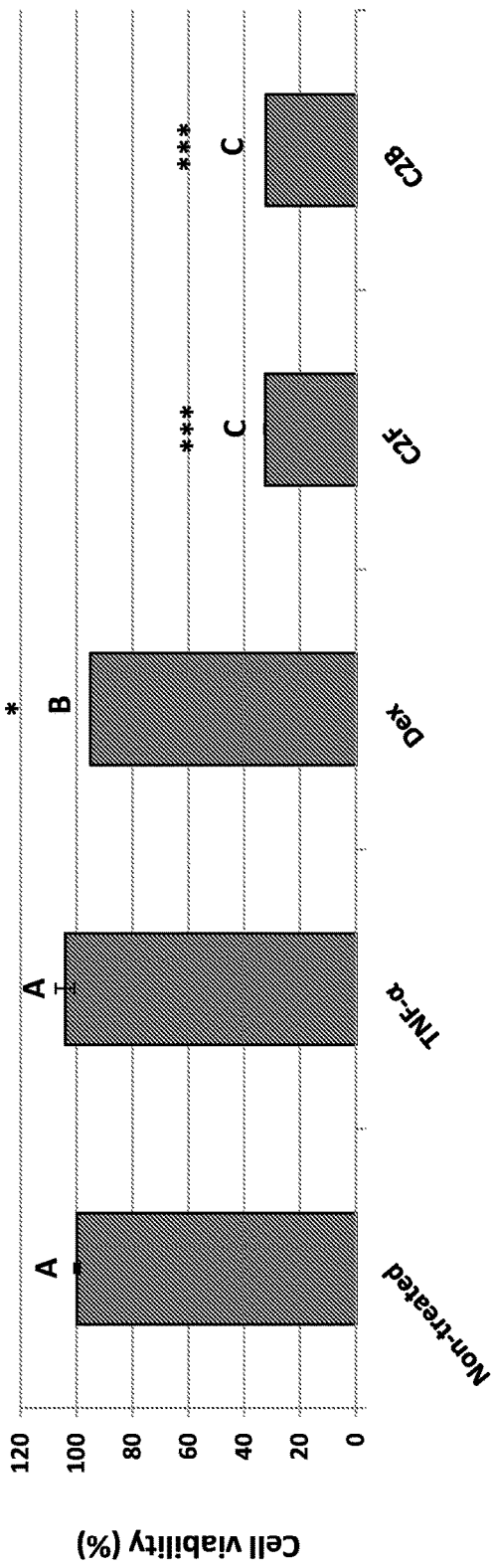
Figure 1B:
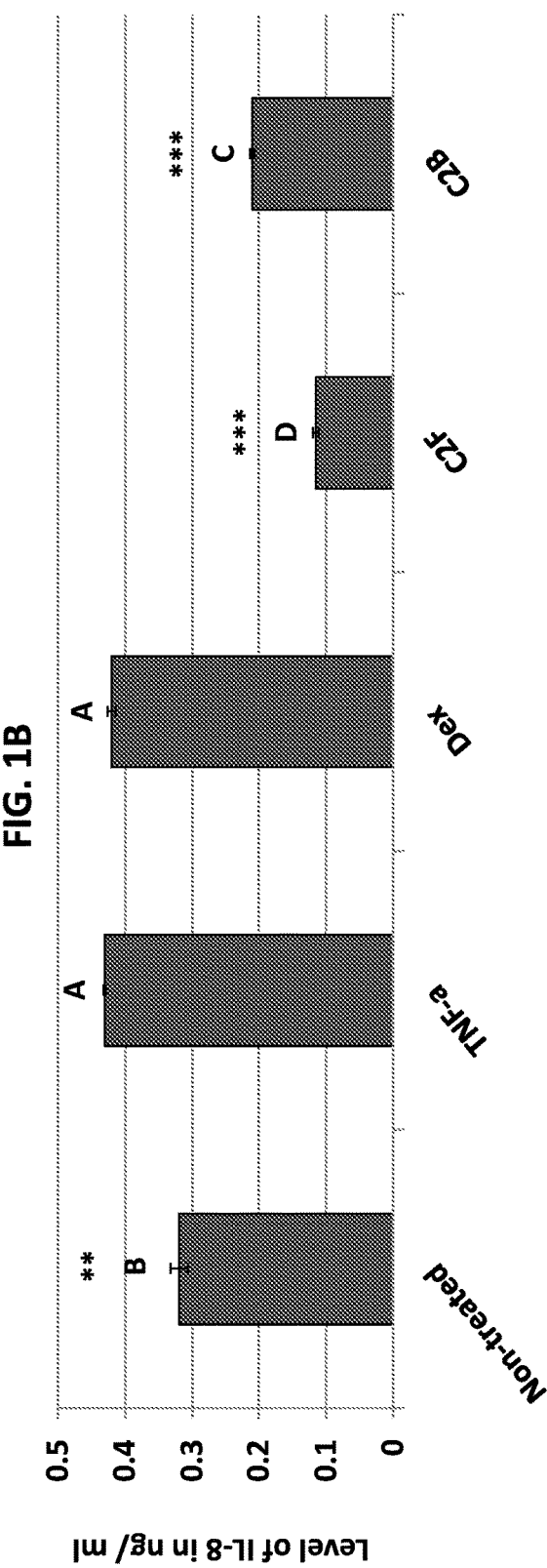
Figure 1C:
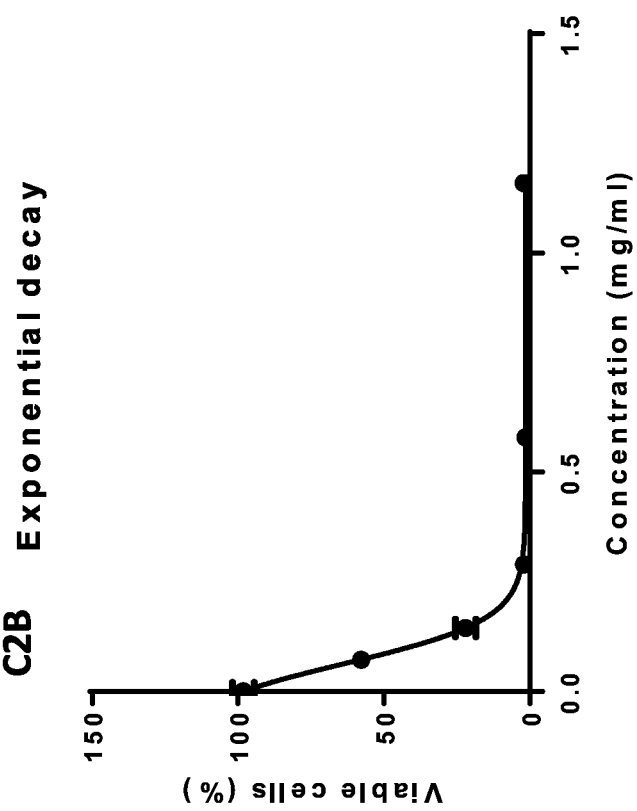
Figure 1D:
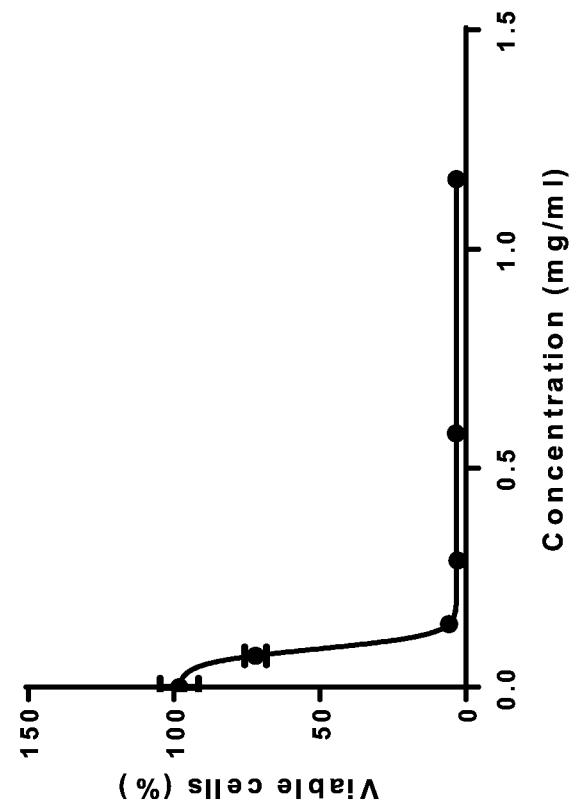
Figure 1E:
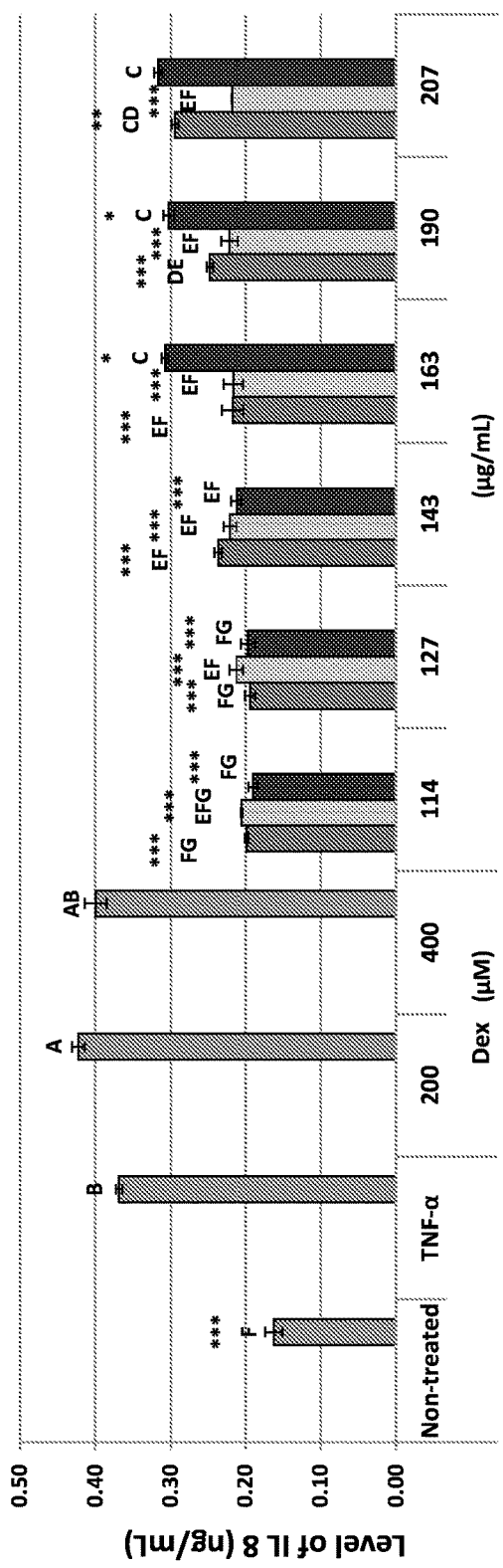
Figure 1F:
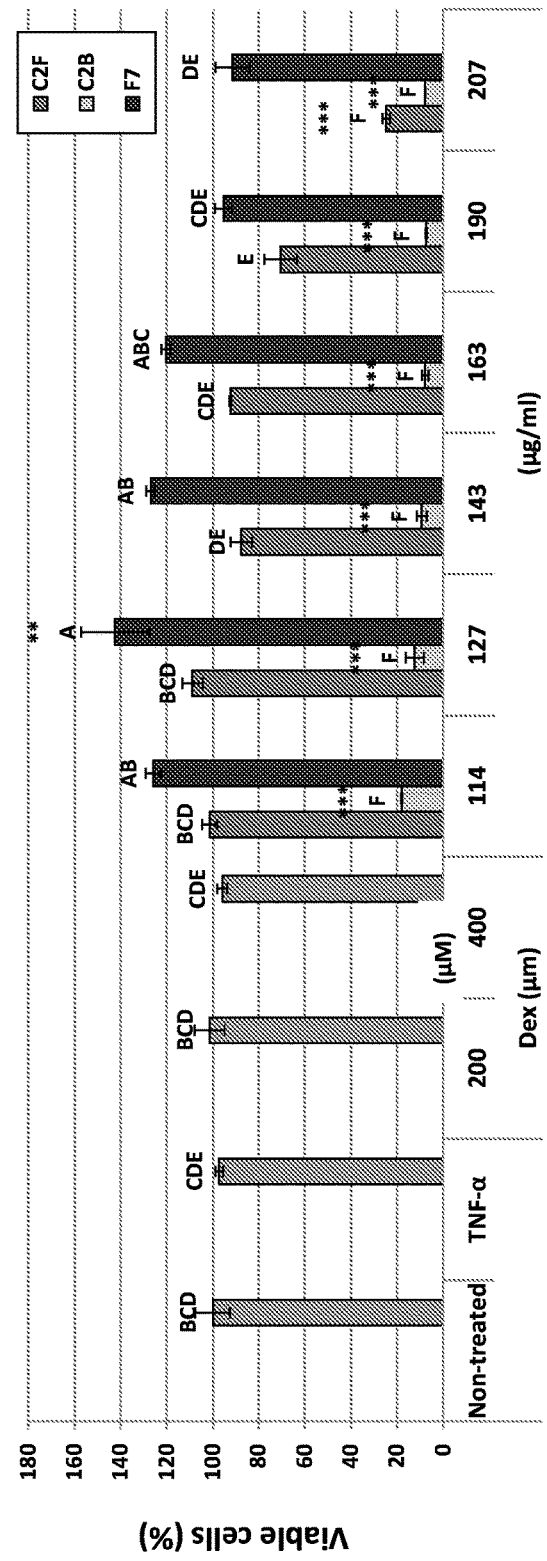

FIGS. 1E-F depict (FIG. 1E) Anti-inflammatory activity at different concentrations of *Cannabis sativa* ethanolic fresh flower extracts (C2F; 114-207 μg/mL), baked flower extracts (C2B; 114-207 μg/mL), F7 from fresh flower extracts (an HPLC fraction of C2F at concentrations of 114-207 μg/mL), and Dex at 200 and 400 μM on HCT 116 cells measured as level of IL-8 (ng/mL). HCT116 cells were seeded (50,000 per well) in triplicate in 500 μL, growing media and incubated for 24 hours at 37° C. in a humidified 5% CO2-95% air atmosphere. Cells were treated with 300 ng/mL TNF-α and 50 μL of *C. sativa* ethanol extract of C2F or fractions for 4 hours. Non-treated are the cells without TNF-α and treatments. Levels of IL-8 were measured from the supernatant using a commercial kit. Values (ng/mL) were calculated relative to a TNF-α-treated control. (FIG. 1F) Determination of HCT116 cell viability using Alamar Blue fluorescence (resazurin assay) as a function of live cell number. Cells were seeded and treated as described in (FIG. 1E). Next, the cells were incubated with Alamar Blue for 2 hours. Relative fluorescence at the excitation/emission of 544/590 nm was measured. Values were calculated as percentage of live cells relative to the non-treated (cells without TNF-α and treatments) control after reducing the auto fluorescence of Alamar Blue without cells. Error bars indicate—SE (n=3). *, , * Indicate data statistically significantly different in comparison with the control (TNF-α-treated cells) at $p≤0.01$, $p≤0.001$, $p≤0.0001$, respectively. Levels with different letters are significantly different from all combinations of pairs by Tukey's HSD. Of note, HPLC, high-performance liquid chromatography; HSD, honest significant difference; Dex, dexamethasone; IL, interleukin; TNF-α, tumor necrosis factor alpha; SE, standard error; F7, fraction 7.

Figure 1G:
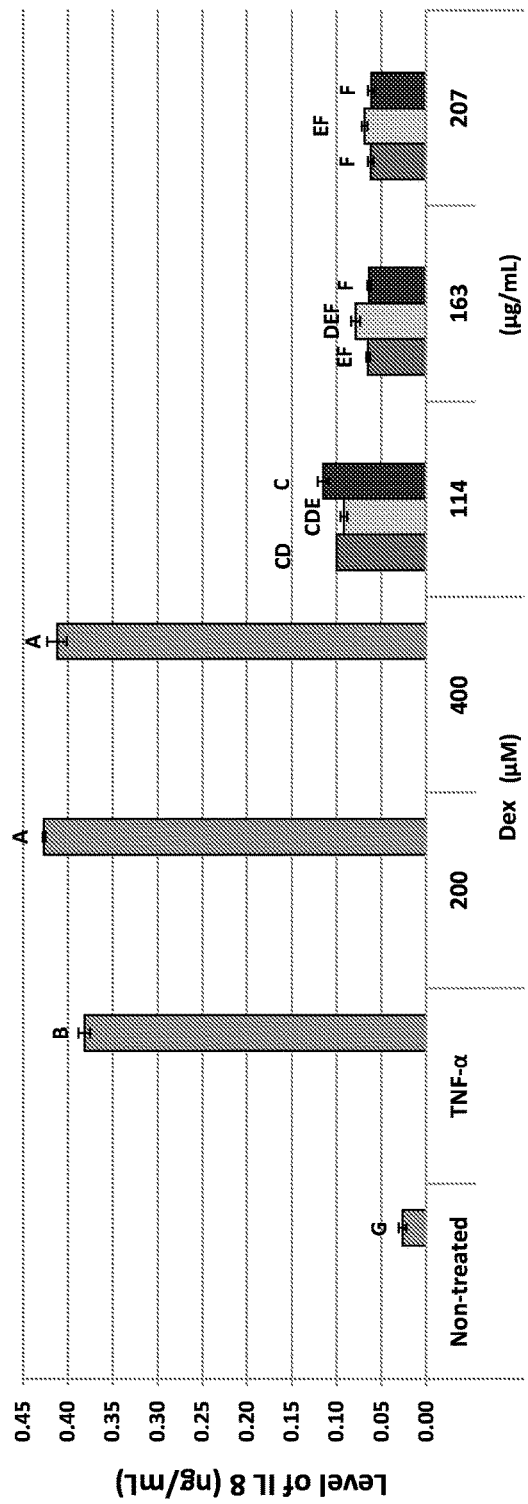
Figure 1H:
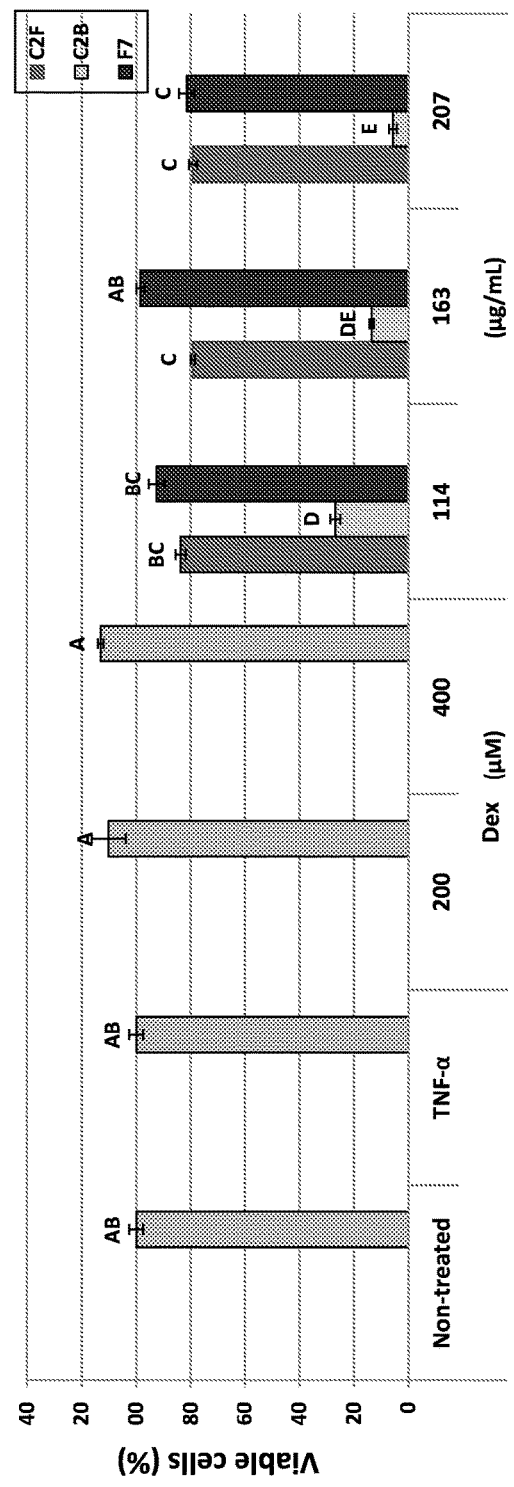

FIGS. 1G-H depict (FIG. 1G) Anti-inflammatory activity at different concentration of *C. sativa* ethanolic fresh flower extracts (C2F; 114 μg/mL to 207 μg/mL), baked flower extracts (C2B; 114 μg/mL to 207 μg/mL), F7 from fresh flower extracts (an HPLC fraction of C2F at concentrations of 114 μg/mL to 207 μg/mL) and dexamethasone (Dex) at 200 and 400 μM on HT 29 cells measured as level of IL-8 (ng/ml). HT 29 were seeded (50,000 per well) in triplicate in 500 μL, growing media and incubated for 24 hours at 37° C. in a humidified 5% $CO_2$-95% air atmosphere. Cells were treated with 300 ng/mL TNF-α and 50 μL of *C. sativa* ethanol extract of C2F or fractions for 4 hours. Non-treated are the cells without TNF-α and treatments. Levels of IL-8 were measured from the supernatant using a commercial kit. Values (ng/mL) were calculated relative to a TNF-α-treated control. (FIG. 1H) Determination of HT29 cell viability using Alamar Blue fluorescence (Resazurin assay) as a function of live cell number. Cells were seeded and treated as described in (FIG. 1G). Next, the cells were incubated with Alamar Blue for 2 hours. Relative fluorescence at the excitation/emission of 544/590 nm was measured. Values were calculated as percentage of live cells relative to the non-treated (cells without TNF-α and treatments) control after reducing the auto fluorescence of Alamar Blue without cells. Error bars indicate ±SE (n=3). *, , * indicates data statistically significantly different in comparison with the control (TNF-α treated cells) at $p≤0.01$, $p≤0.001$, $p≤0.0001$ respectively. Levels with different letters are significantly different from all combinations of pairs by Tukey HSD.

Figure 1I:
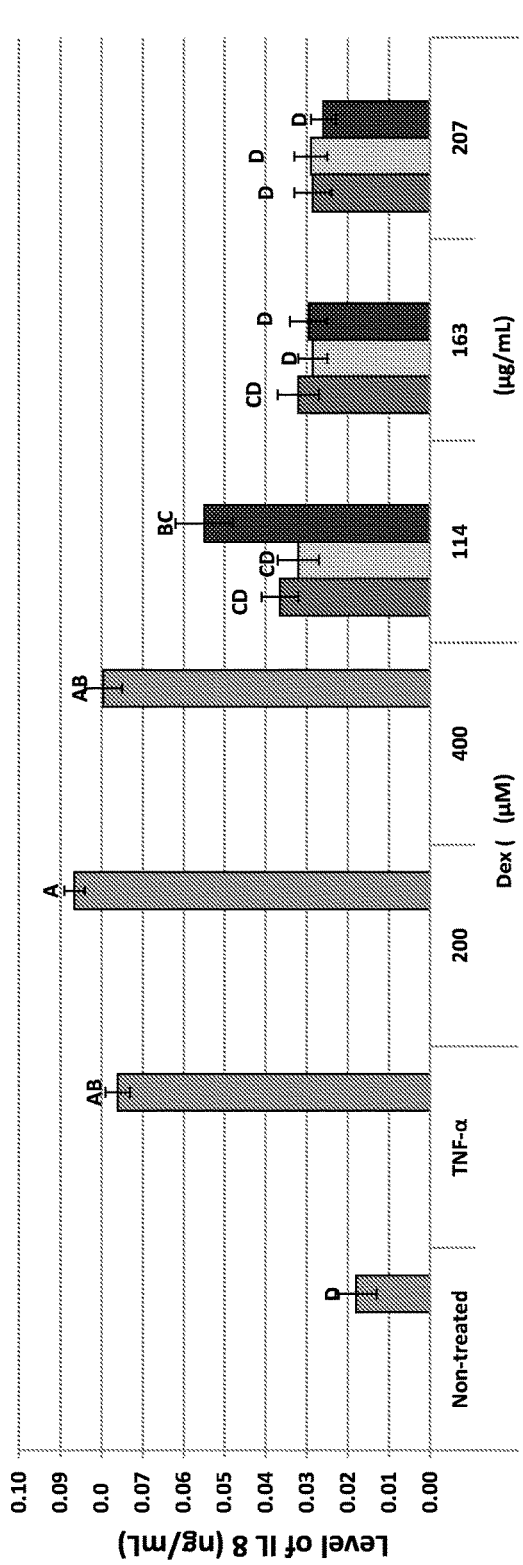
Figure 1J:
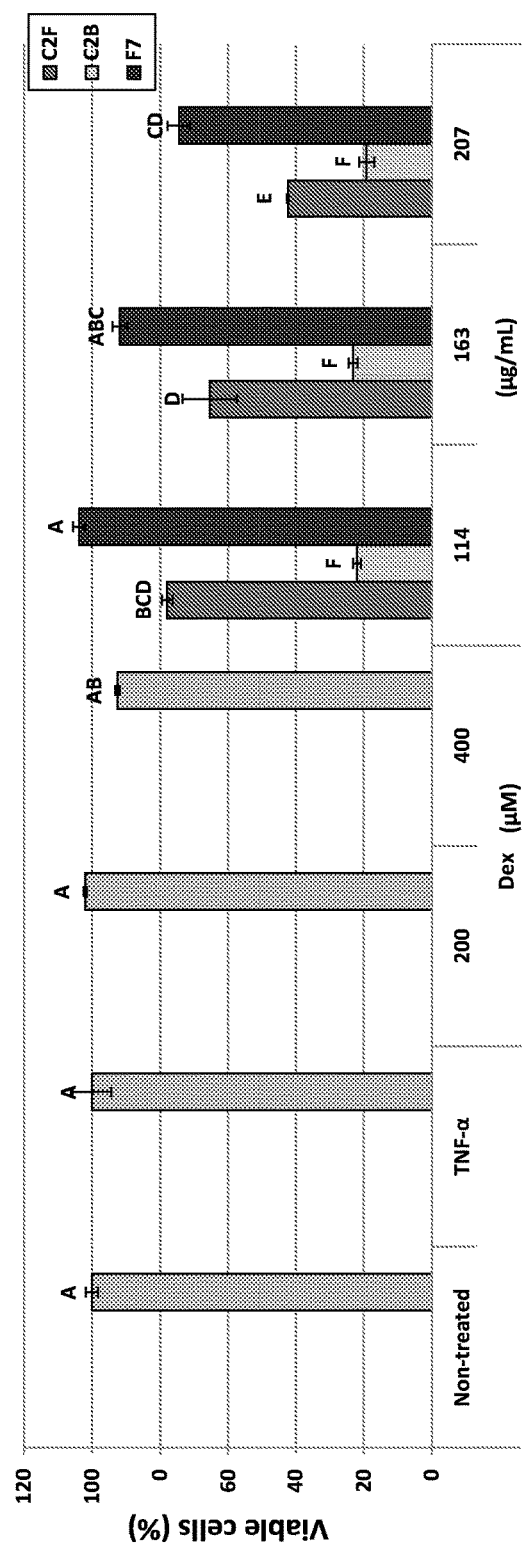

FIGS. 1I-J depict (FIG. 1I) Anti-inflammatory activity at different concentration of *C. sativa* ethanolic fresh flower extracts (C2F; 114 μg/mL to 207 μg/mL), baked flower extracts (C2B; 114 μg/mL to 207 μg/mL), F7 from fresh flower extracts (an HPLC fraction of C2F at concentrations of 114 μg/mL to 207 μg/mL) and dexamethasone (Dex) at 200 and 400 μM on CaCO2 cells measured as level of IL-8 (ng/ml). CaCO2 were seeded (50,000 per well) in triplicate in 500 μL, growing media and incubated for 24 hours at 37° C. in a humidified 5% $CO_2$-95% air atmosphere. Cells were treated with 300 ng/mL TNF-α and 50 μL of *C. sativa* ethanol extract of C2F or fractions for 4 hours. Non-treated are the cells without TNF-α and treatments. Levels of IL-8 were measured from the supernatant using a commercial kit. Values (ng/mL) were calculated relative to a TNF-α-treated control. (FIG. 1J) Determination of CaCO2 cell viability using Alamar Blue fluorescence (Resazurin assay) as a function of live cell number. Cells were seeded and treated as described in (FIG. 1I). Next, the cells were incubated with Alamar Blue for 2 hours. Relative fluorescence at the excitation/emission of 544/590 nm was measured. Values were calculated as percentage of live cells relative to the non-treated (cells without TNF-α and treatments) control after reducing the auto fluorescence of Alamar Blue without cells. Error bars indicate ±SE (n=3). *, , * indicates data statistically significantly different in comparison with the control (TNF-α treated cells) at p≤0.01, p≤0.001, p≤0.0001 respectively. Levels with different letters are significantly different from all combinations of pairs by Tukey HSD.

Figure 2A:
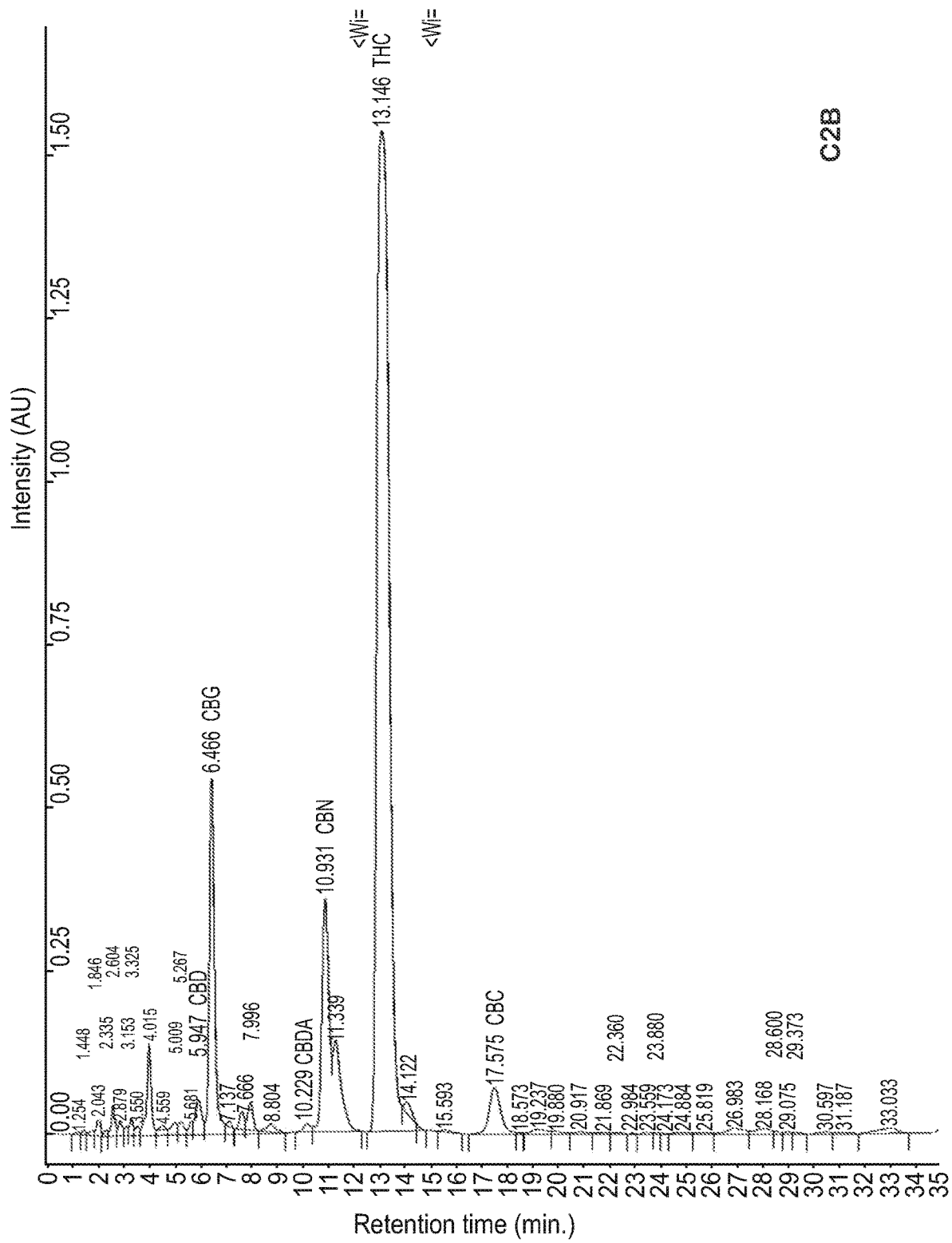
Figure 2B:
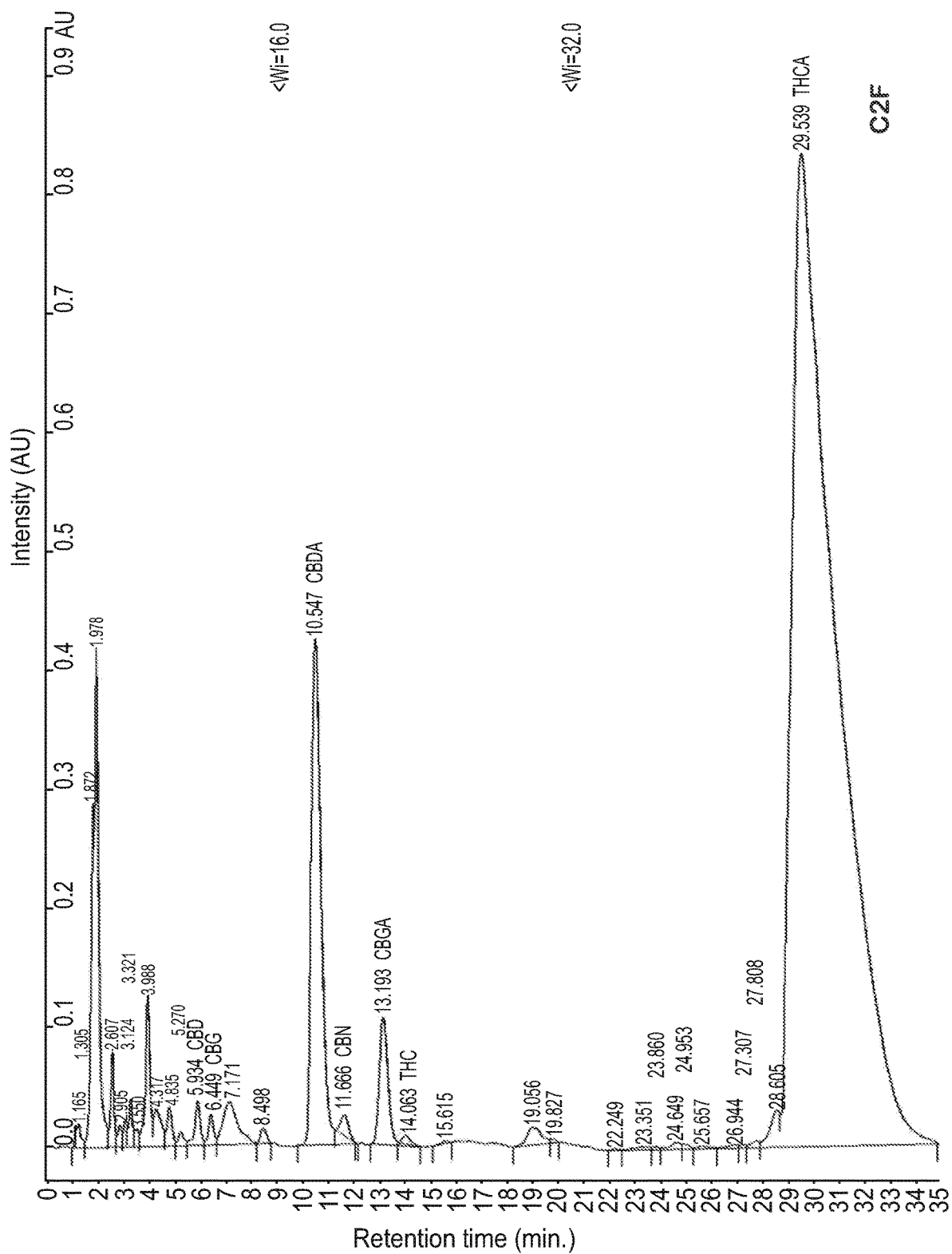

FIGS. 2A-B depicts HPLC chromatograms of *C. sativa* ethanolic extracts. Chromatogram of fresh cannabis extract (FIG. 2B, C2F, 0.1 mg/mL) and baked (i.e., fresh flowers which were baked at 150° C. for 3 hours) cannabis extract (FIG. 2A, C2B, 0.1 mg/mL) obtained from isocratic elution with a mixture of 15% water containing 0.1% acetic acid (solvent A) and 85% MeOH (solvent B) for a total run time of 35 minutes at 220 nm. The samples were injected at a concentration of 0.58 mg/mL in a volume of 20 μL for C2B and 0.33 mg/mL in a volume of 20 μL for C2F.

FIGS. 3A-D depict (FIG. 3A) HPLC profile of fractions of *C. sativa* ethanolic extract. HPLC profile was obtained from isocratic elution with a mixture of 15% water containing 0.1% acetic acid (solvent A) and 85% MeOH (solvent B) for a total run time of 40 minutes at 220 nm. The sample was injected at a concentration of 0.1 mg crude dried extract/mL in a volume of 50 μL per cycle. Fractions were collected every 2 minutes. F1-F9 represent the nine fractions into which the peaks were divided. (FIG. 3B) Anti-inflammatory activity of fractions F1-F9 pooled together, F1-F9 pooled together without F7, F1-F9 separately from fresh flowers (C2F, 0.9 mg/mL) of *C. sativa* ethanolic extracts measured as level of IL-8 (ng/mL) on HCT116 cells. (FIG. 3C) Anti-inflammatory activity of fractions F1-F9 pooled together without F7, F1-F9 pooled together with F7, F7 from fresh flowers (C2F) of *C. sativa* ethanolic extracts with different dilution (a) 0.14, (b) 0.15 and (c) 0.16 mg/ml, measured as level of IL-8 (ng/mL) on HCT116 cells. HCT116 cells were seeded (50,000 per well) in triplicate in 500 μL, growing media and incubated for 24 hours at 37° C. in a humidified 5% $CO_2$-95% air atmosphere. Cells were treated with 50 ng/mL TNF-α and 50 μL of *C. sativa* ethanol extract of C2F or fractions for 16 hours. Non-treated are the cells without TNF-α and treatments. Levels of IL-8 were measured from the supernatant using a commercial kit. Values (ng/mL) were calculated relative to a TNF-α-treated control. Error bars indicate ±SEM (n=3). *, , * indicates data statistically significantly different in comparison with the control (TNF-α treated cells) at p≤0.05, p≤0.001, p≤0.0001 respectively. Levels with different letters are significantly different from all combinations of pairs by turkey HSD. (FIG. 3D) Anti-inflammatory activity of *C. sativa* ethanolic extracts of fresh (C2F, 0.2 mg/mL) and baked (C2B, 0.2 mg/mL) cannabis flowers, 25 μM CBD and 20 μM dexamethasone, measured as level of IL-8 on HT29 cells. HT29 cells were seeded (50,000 per well) in triplicate in 500 μL, growing media and incubated for 24 hours at 37° C. in a humidified 5% $CO_2$-95% air atmosphere. Cells were treated with 50 ng/mL TNF-α and 50 μL *C. sativa* ethanol extracts of C2F, C2B, CBD or dexamethasone. IL-8 values were measured from the supernatant using a commercial kit. Values (ng/mL) were calculated relative to a TNF-α-treated control. Non-treated are the cells without TNF-α and treatments. Error bars indicate ±SEM (n=3). *, , * indicates data statistically significantly different in comparison with the control (TNF-α treated cells) at p≤0.05, p≤0.001, p≤0.0001 respectively. Levels with different letters are significantly different from all combinations of pairs by turkey HSD.

FIGS. 3E-F depict (FIG. 3E) Anti-inflammatory activity of *C. sativa* ethanolic extracts (C2F; 163 μg/mL), fractions F1-F9 pooled together (HPLC fractions of C2F at concentrations of 163 μg/mL), F1-F9—excluding F7 (HPLC fractions of C2F at concentrations of 163 μg/mL), F1-F9 (each an HPLC fraction of C2F at concentrations of 163 μg/mL) on HCT 116 cells measured as level of IL-8 (ng/mL). HCT116 cells were seeded (50,000 per well) in triplicate in 500 μL, growing media and incubated for 24 hours at 37_° C. in a humidified 5% CO2-95% air atmosphere. Cells were treated with 300 ng/mL TNF-α and 50 μL of *C. sativa* ethanol extract of C2F or fractions for 4 hours. Non-treated are the cells without TNF-α and treatments. Levels of IL-8 were measured from the supernatant using a commercial kit. Values (ng/mL) were calculated relative to a TNF-α-treated control. (FIG. 3F) Determination of HCT116 cell viability using Alamar Blue fluorescence (resazurin assay) as a function of live cell number. Cells were seeded and treated as described in (FIG. 3E). Next, the cells were incubated with Alamar Blue for 2 hours. Relative fluorescence at the excitation/emission of 544/590 nm was measured. Values were calculated as percentage of live cells relative to the non-treated (cells without TNF-α and treatments) control after reducing the auto fluorescence of Alamar Blue without cells. Error bars indicate—SE (n=3). *, *** Indicate data statistically significantly different in comparison with the control (TNF-α treated cells) at p≤0.01 and p≤0.0001, respectively. Levels with different letters are significantly different from all combinations of pairs by Tukey's HSD.

Figure 3A:
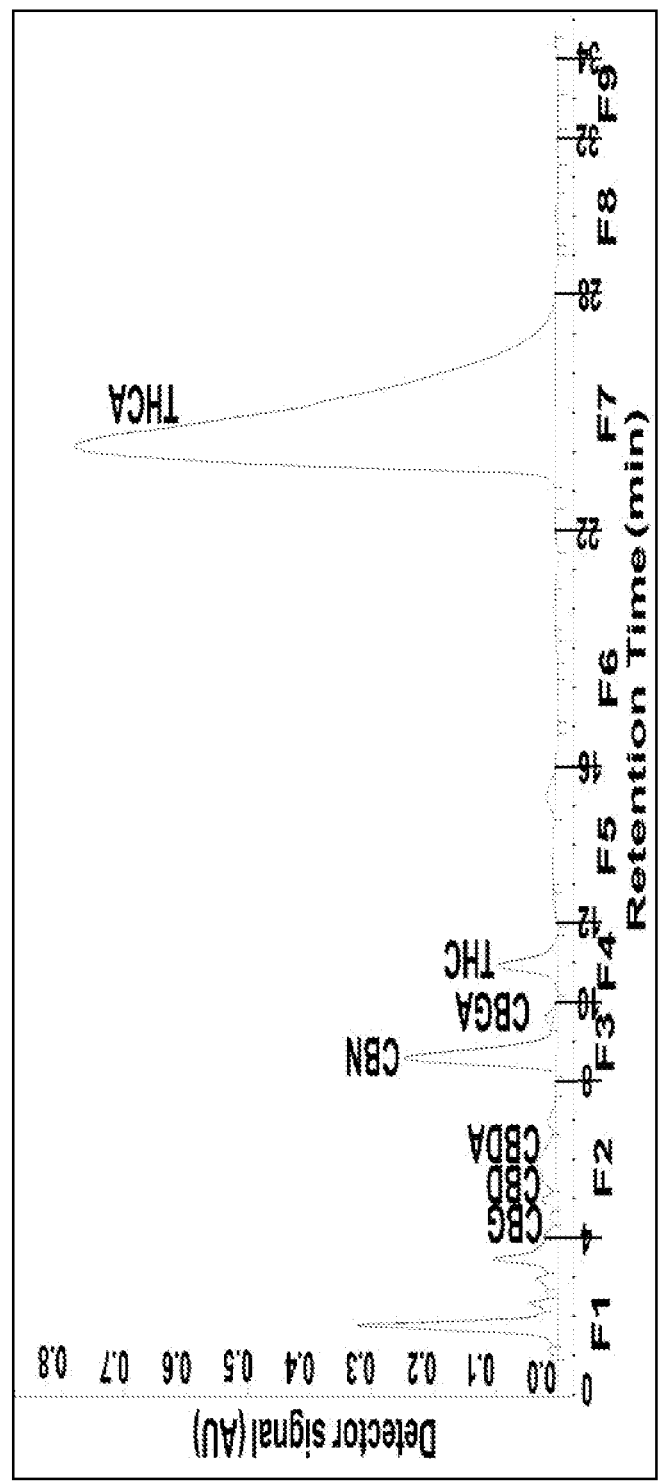
Figure 3B:
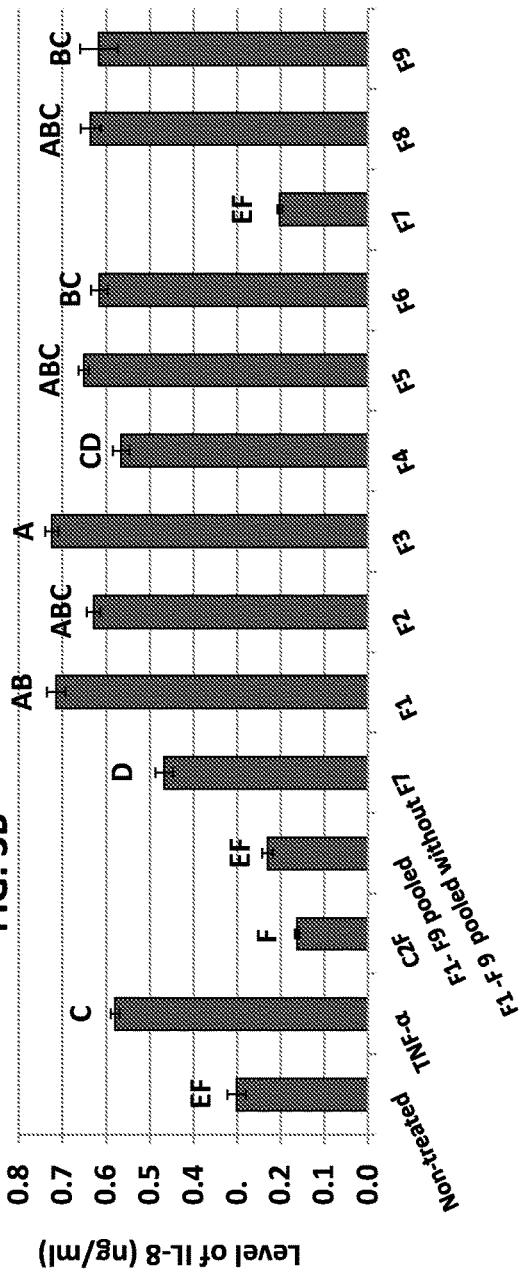
Figure 3C:
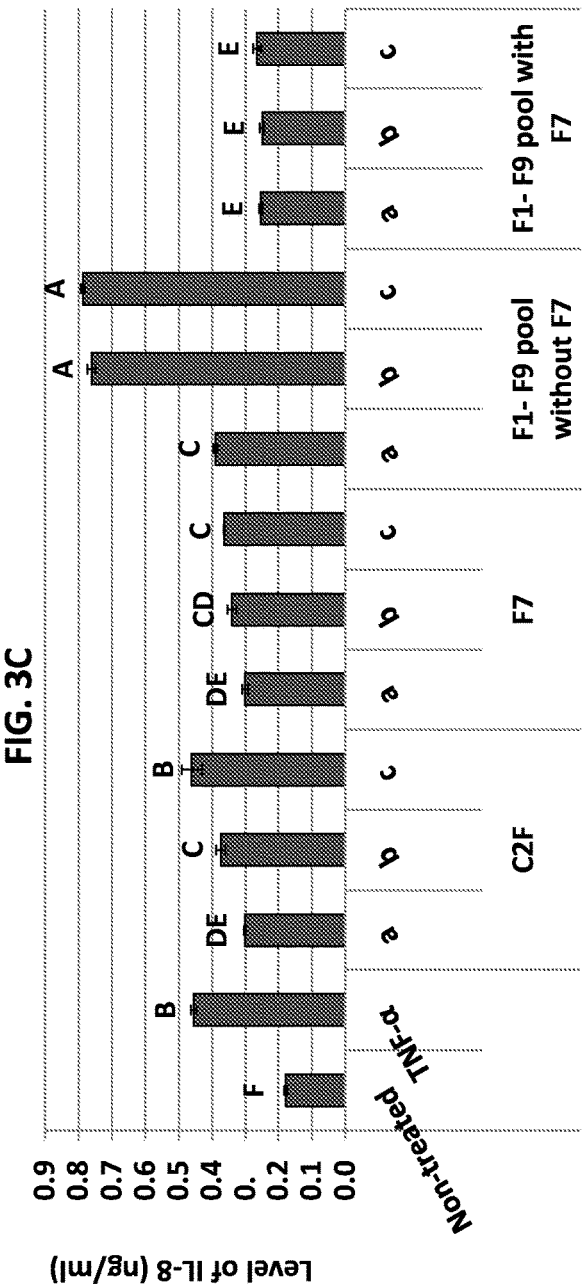
Figure 3D:
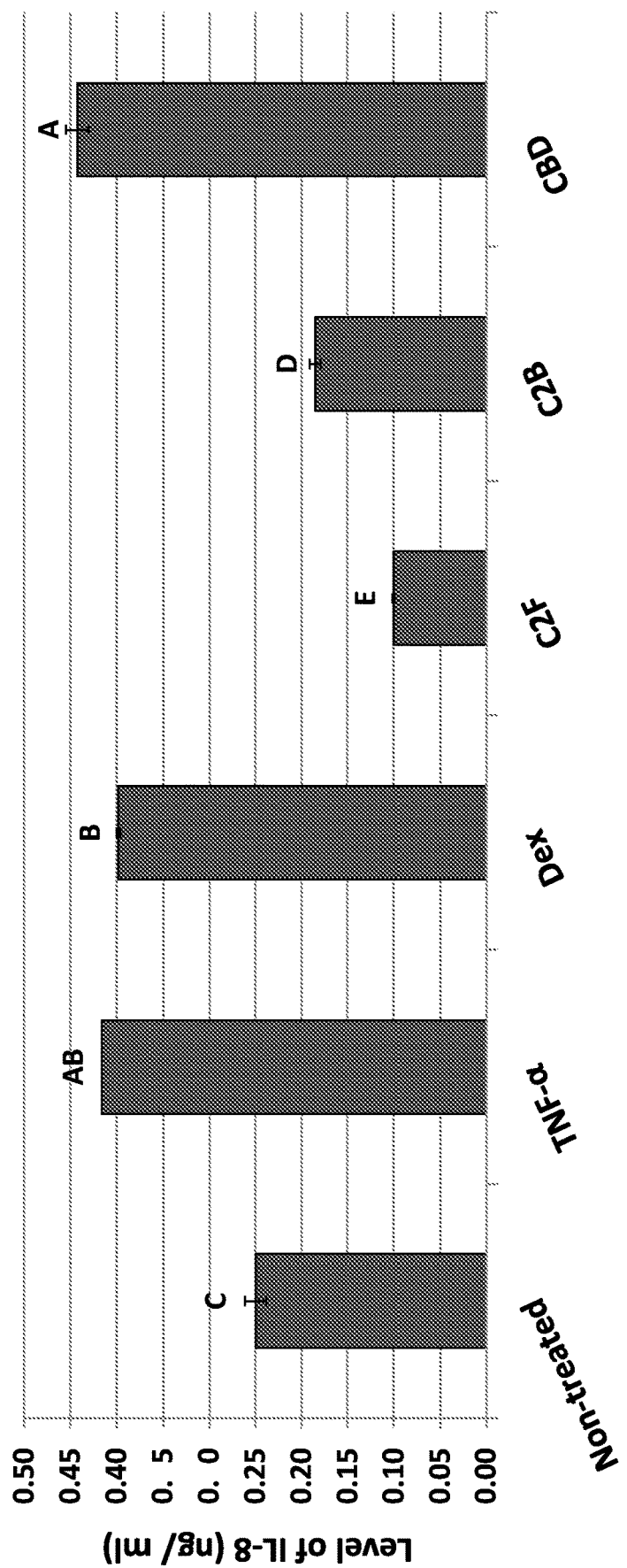
Figure 3G:
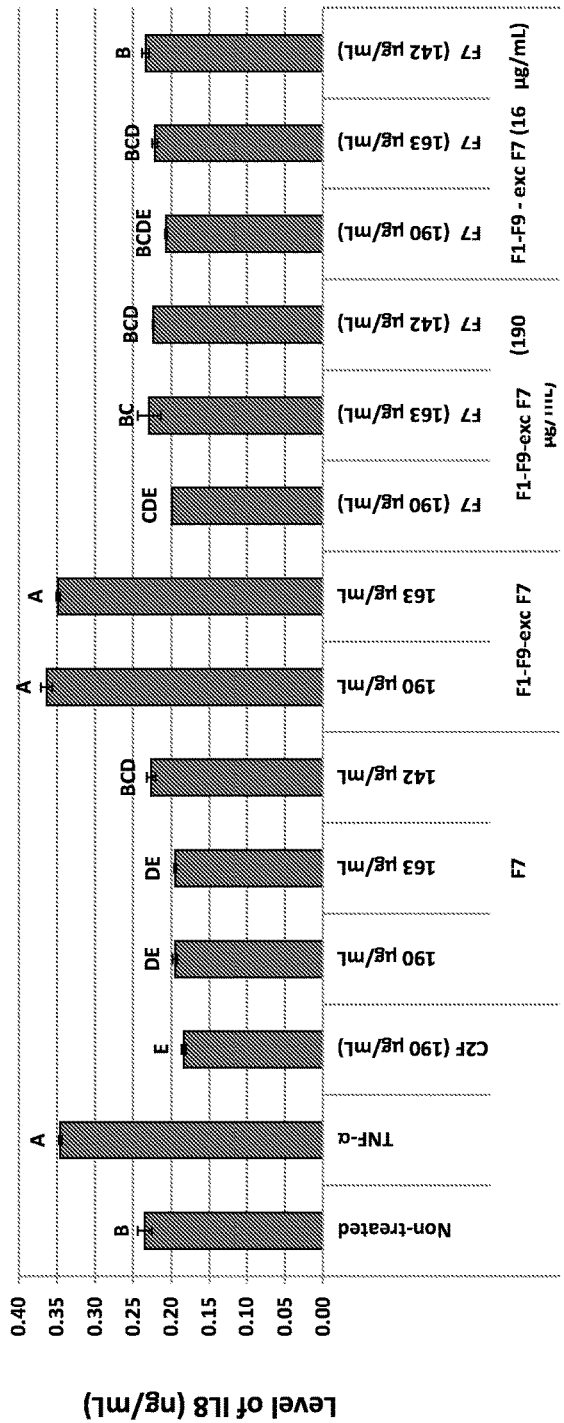
Figure 3H:
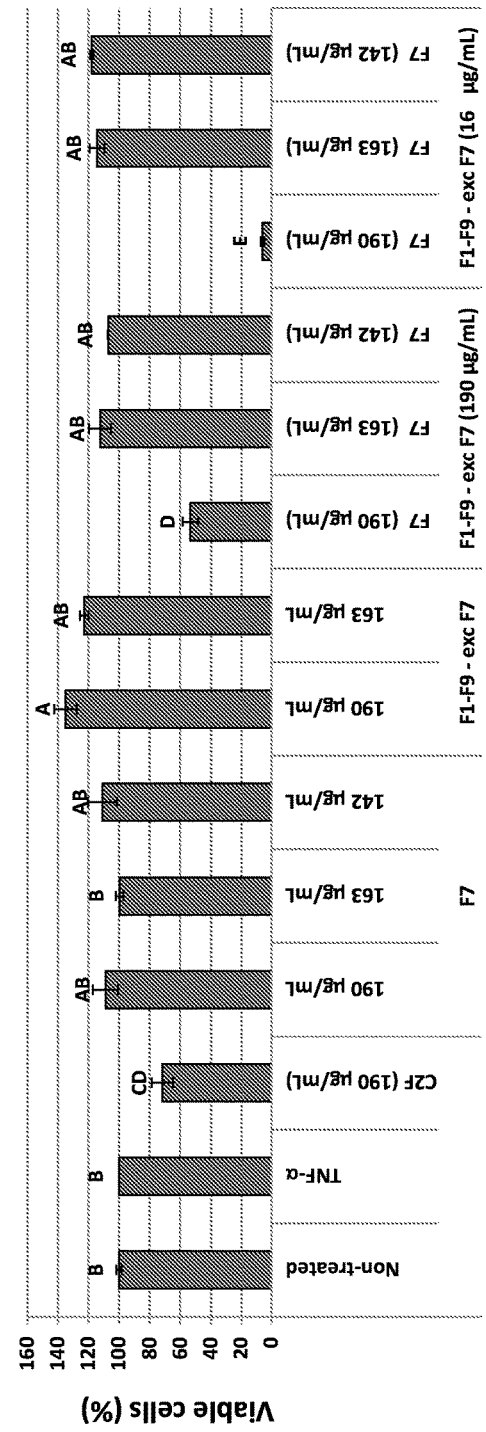

FIGS. 3G-H depict (FIG. 3G) Anti-inflammatory activity of *C. sativa* ethanolic extracts (C2F; 163 μg/mL), F7 at three different concentrations (an HPLC fraction of C2F at concentrations of 142, 163, and 190 μg/mL), fractions F1-F9— excluding F7 (F1-F9—exc F7) at two concentrations (HPLC fractions of C2F at concentrations of 163 and 190 μg/mL), combination of each concentration of F1-F9—excluding F7 along with each concentration of F7 on HCT 116 cells measured as level of IL-8 (ng/mL). HCT116 cells were seeded (50,000 per well) in triplicate in 500 μL, growing media and incubated for 24 hours at 37_° C. in a humidified 5% CO2-95% air atmosphere. Cells were treated with 300 ng/mL TNF-α and 50 μL of *C. sativa* ethanol extract of C2F or fractions for 4 hours. Non-treated are the cells without TNF-α and treatments. Levels of IL-8 were measured from the supernatant using a commercial kit. Values (ng/mL) were calculated relative to a TNF-α-treated control. (FIG. 3H) Determination of HCT116 cell viability using Alamar Blue fluorescence (resazurin assay) as a function of live cell number. Cells were seeded and treated as described in (FIG. 3G). Next, the cells were incubated with Alamar Blue for 2 hours. Relative fluorescence at the excitation/emission of 544/590 nm was measured. Values were calculated as percentage of live cells relative to the non-treated (cells without TNF-α and treatments) control after reducing the auto fluorescence of Alamar Blue without cells. Error bars indicate—SE (n=3). , * Indicate data statistically significantly different in comparison with the control (TNF-α-treated cells) at p≤0.001 and p≤0.0001, respectively. Levels with different letters are significantly different from all combinations of pairs by Tukey's HSD.

Figure 3I:
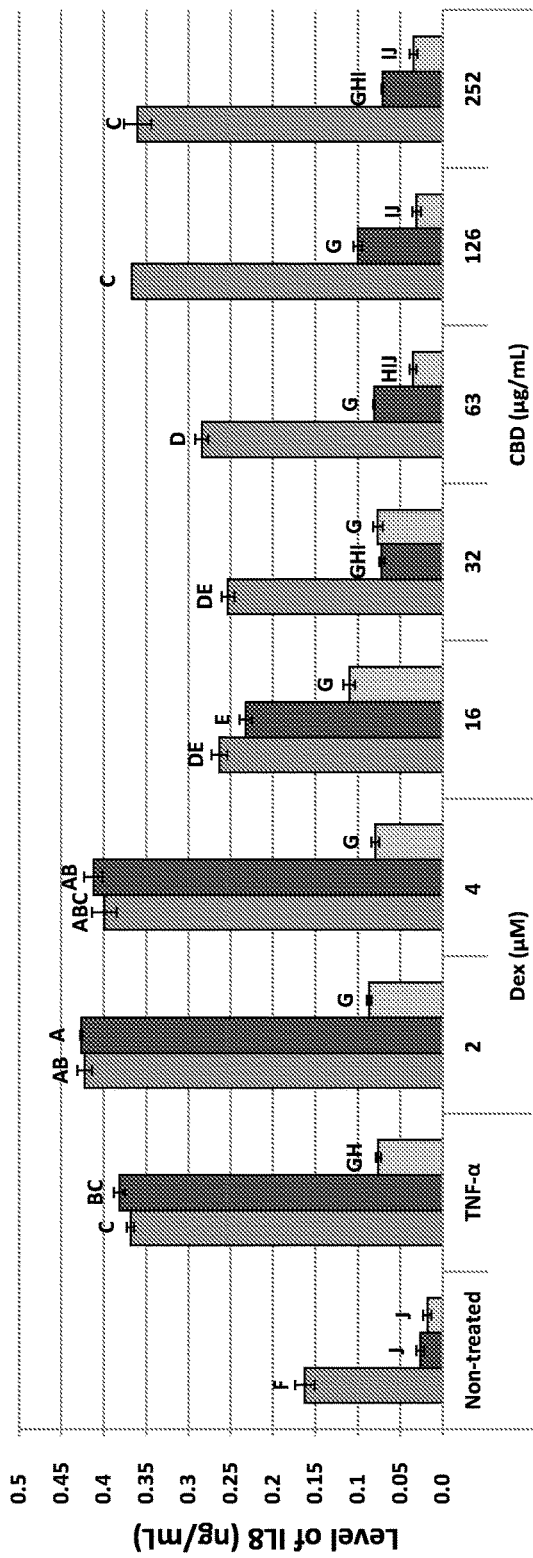
Figure 3J:
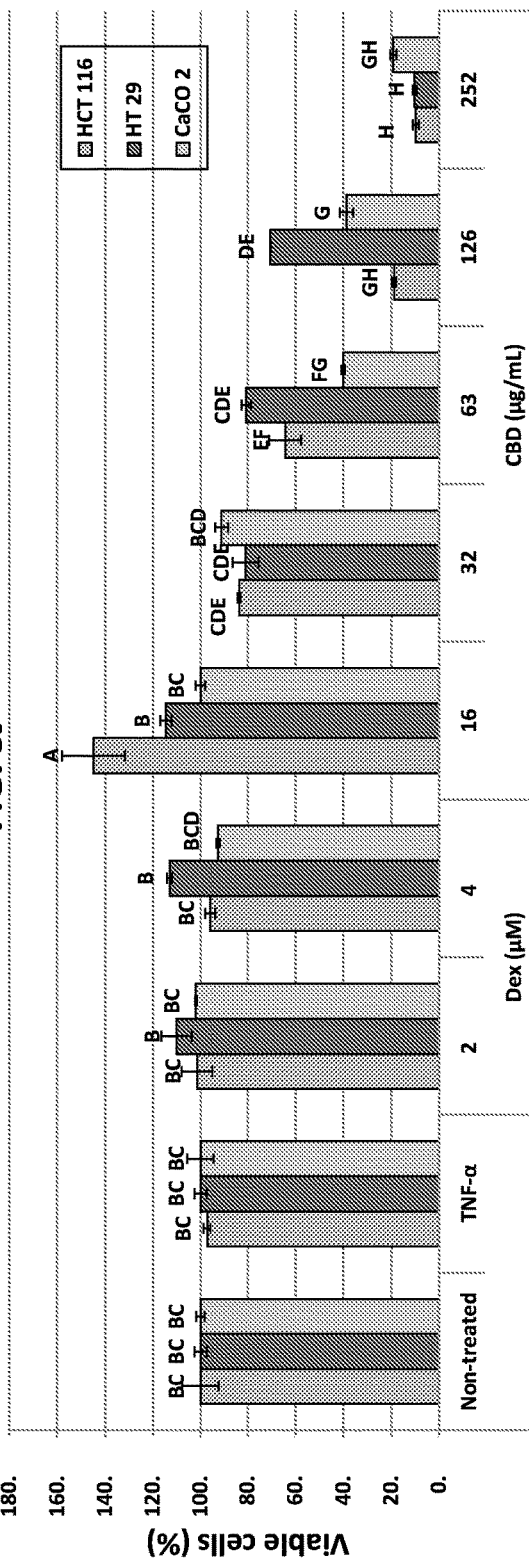

FIGS. 3I-J depict (FIG. 3I) Anti-inflammatory activity of cannabidiol (CBD) at different concentrations (16 μg/mL to 252 μg/mL) and dexamethasone (Dex; 200 and 400 μM), measured as level of IL-8 on HCT116, HT29 or CaCO2 cells. HCT116, HT29 or CaCO2 cells were seeded (50,000 per well) in triplicate in 500 μL growing media and incubated for 24 hours at 37° C. in a humidified 5% $CO_2$-95% air atmosphere. Cells were treated with 300 ng/mL TNF-α and CBD and dexamethasone for 4 hours and IL-8 values were measured from the supernatant using a commercial kit. Values (ng/mL) were calculated relative to a TNF-α-treated control. Non-treated are the cells without TNF-α and treatments. (FIG. 3J) Determination of HCT116, HT29 and CaCO2 cell viability using Alamar Blue fluorescence (Resazurin assay) as a function of live cell number. Cells were seeded and treated as described in (FIG. 3I). Following the cells were incubated with Alamar Blue for 2 hours. Relative fluorescence at the excitation/emission of 544/590 nm was measured. Values were calculated as percentage of live cells relative to the non-treated (cells without TNF-α and treatments) control after reducing the auto fluorescence of Alamar Blue without cells. Error bars indicate ±SE (n=3). *, , * indicates data statistically significantly different in comparison with the control (TNF-α treated cells) at $p \leq 0.01$, $p \leq 0.001$, $p \leq 0.0001$ respectively. Levels with different letters are significantly different from all combinations of pairs by Tukey HSD.

Figure 4:
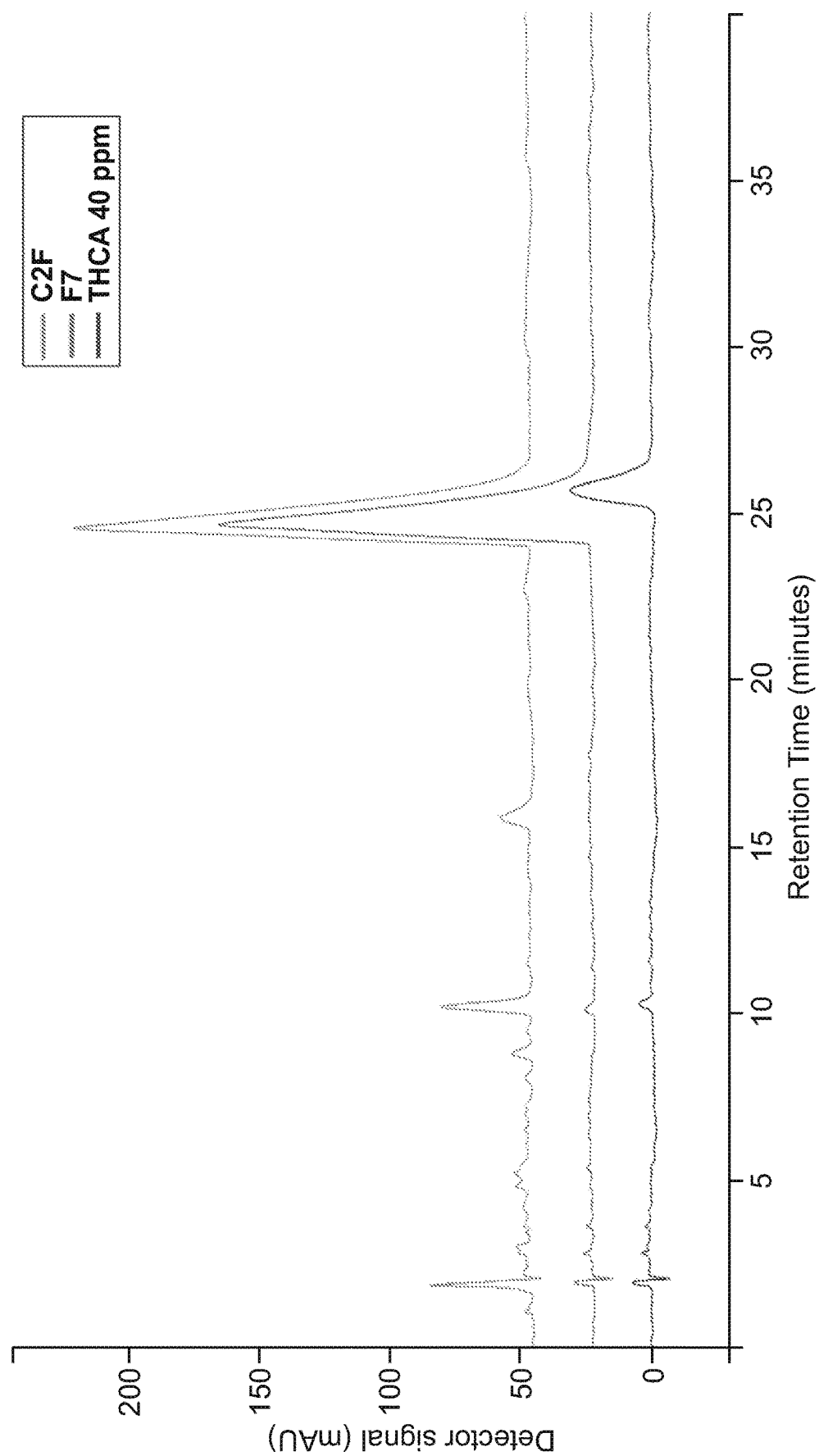

FIG. 4 depicts a HPLC profile of C2F, F7 and THCA. Chromatograms of THCA standard at 40 ppm (marked in blue), whole *C. sativa* extract at 0.1 mg/mL (marked in green) and F7 at 0.04 mg/mL (marked in red). All samples were injected in a volume of 20 μL and were obtained from isocratic elution with a mixture of 15% water containing 0.1% acetic acid (solvent A) and 85% MeOH (solvent B) for a total run time of 40 minutes at 220 nm.

Figure 5:
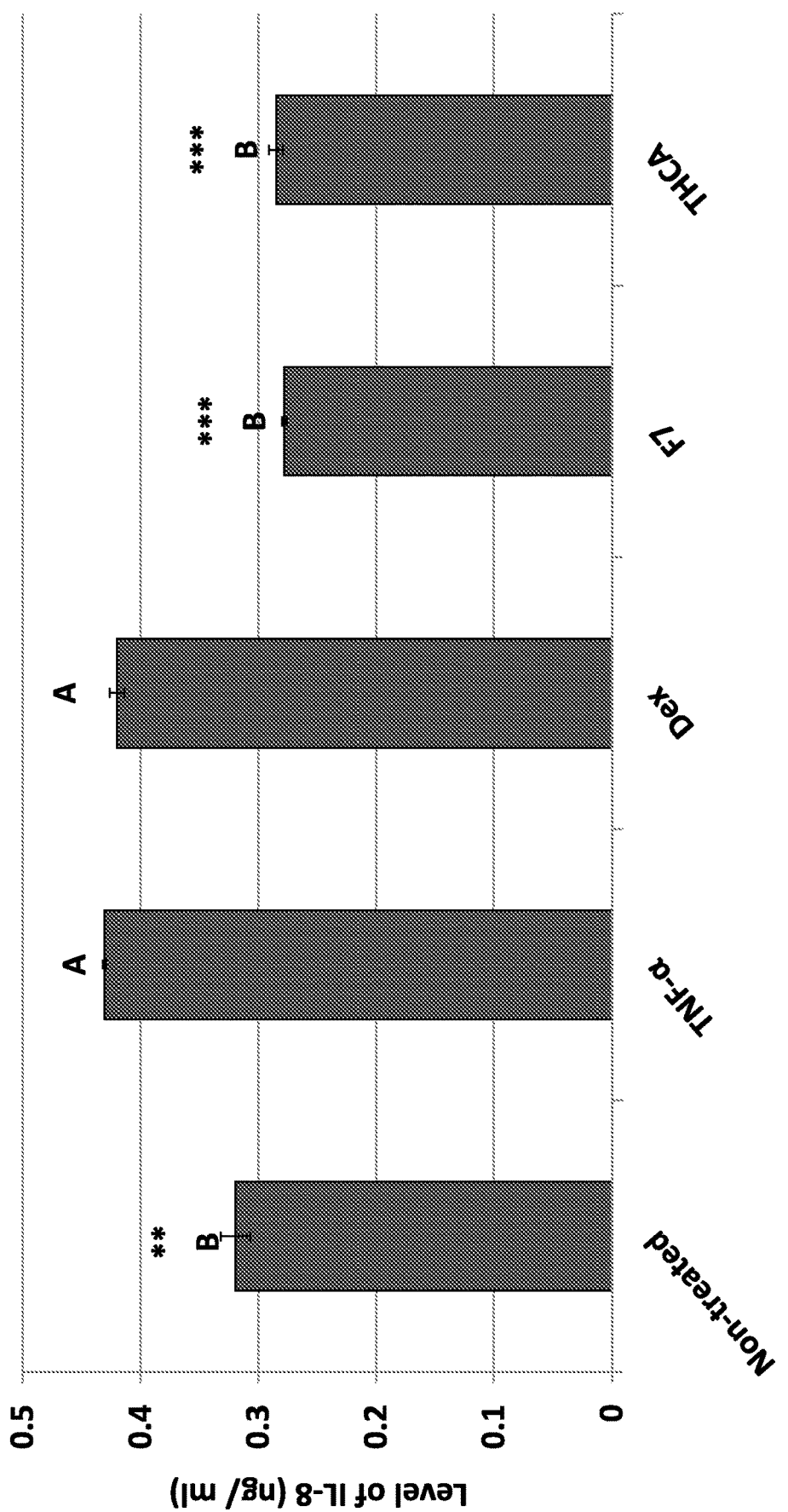

FIG. 5 depicts the anti-inflammatory activity of F7 (0.07 mg/mL) from *C. sativa* fresh flowers ethanol extracts diluted accordingly to the concentration of 0.2 mM THCA, 0.2 mM THCA and 20 μM dexamethasone, measured as level of IL-8 on HCT116 cells. HCT116 cells were seeded (50,000 per well) in triplicate in 500 μL growing media and incubated for 24 hours at 37° C. in a humidified 5% $CO_2$-95% air atmosphere. Cells were treated with 50 ng/mL TNF-α and F7, THCA, dexamethasone for 16 hours. Levels of IL-8 were measured from the supernatant using a commercial kit. Values (ng/mL) were calculated relative to a TNF-α treated control. Non-treated are the cells without TNF-α and treatments. Error bars indicate ±SEM (n=3). *, , * indicates data statistically significantly different in comparison with the control (TNF-α treated cells) at $p \leq 0.05$, $p \leq 0.001$, $p \leq 0.0001$ respectively. Levels with different letters are significantly different from all combinations of pairs by turkey HSD.

Figure 6:
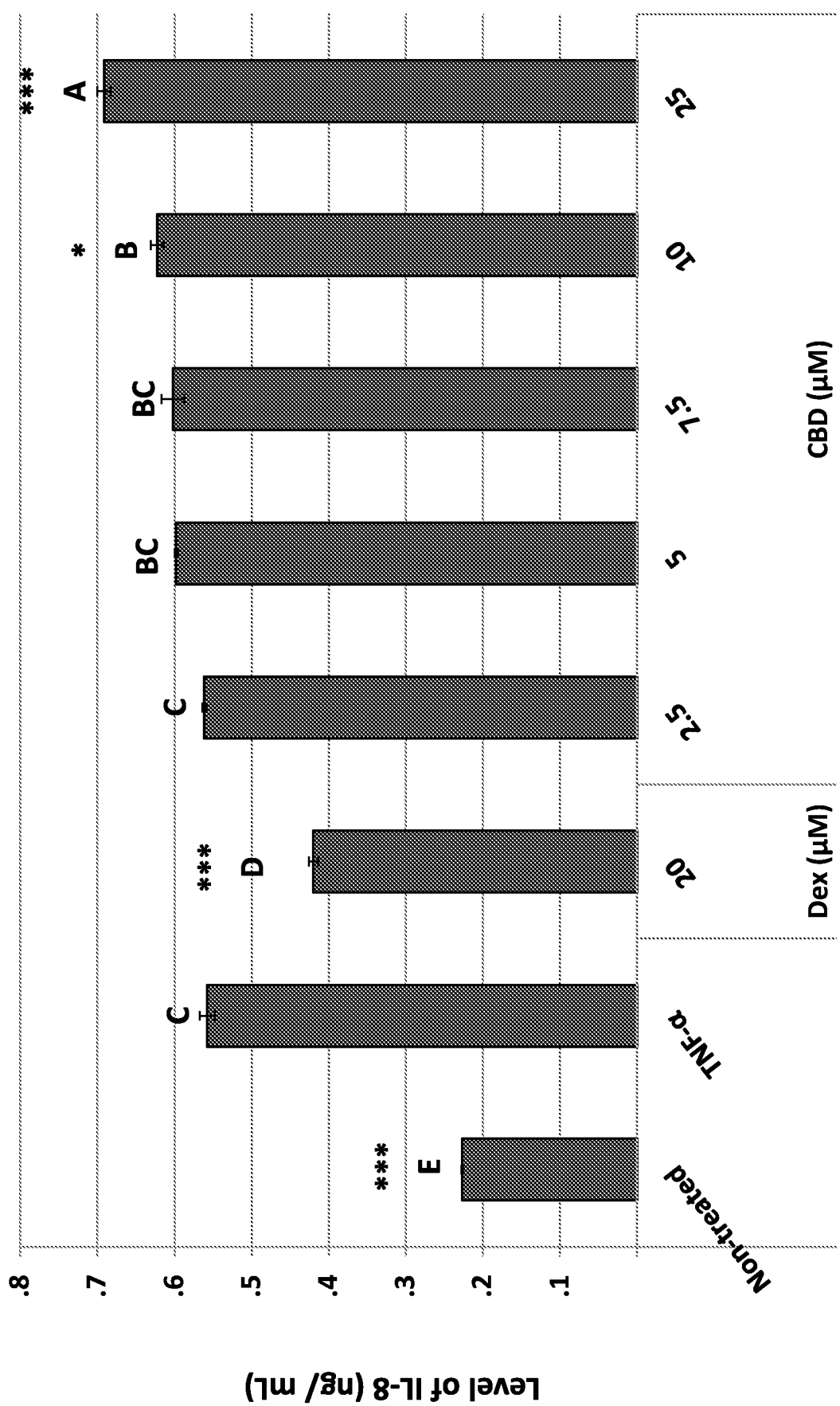

FIG. 6 depicts the anti-inflammatory activity of pure CBD or 20 μM dexamethasone, measured as level of IL-8 levels (ng/mL) on HCT116 cells. HCT116 cells were seeded (50,000 per well) in triplicate in 500 μL, growing media and incubated for 24 hours at 37° C. in a humidified 5% $CO_2$-95% air atmosphere. Cells were treated with 50 ng/mL TNF-α and pure CBD at the different concentrations (2.5, 5, 7.5, 10 and 25 μM), or 20 μM dexamethasone for 16 hours. Non-treated are the cells without TNF-α and treatments. Levels of IL-8 were measured from the supernatant using a commercial kit. Values (ng/mL) were calculated relative to a TNF-α-treated control. Error bars indicate ±SEM (n=3). *, , * indicates data statistically significantly different in comparison with the control (only TNF-α treated cells) at $p \leq 0.05$, $p \leq 0.001$, $p \leq 0.0001$ respectively. Levels with different letters are significantly different from all combinations of pairs by turkey HSD.

Figure 7:
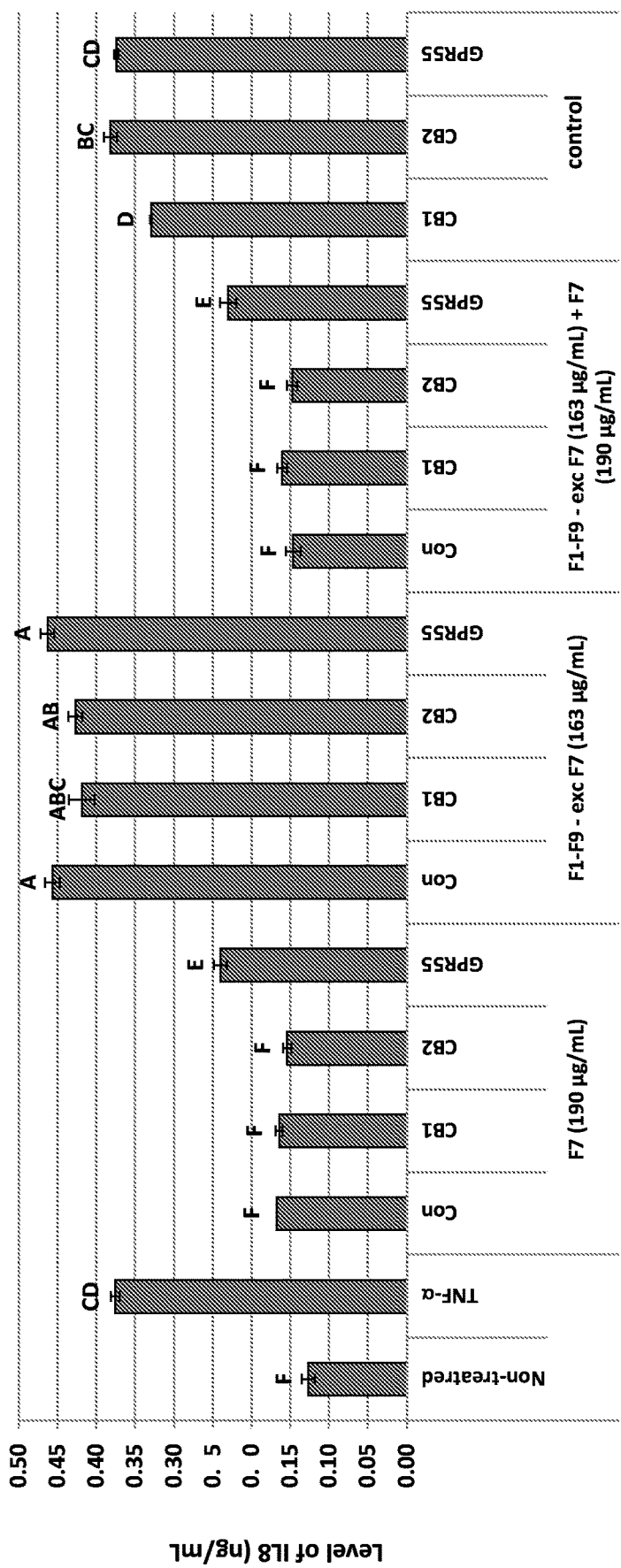

FIG. 7 depicts Anti-inflammatory activity of *C. sativa* F7 at three different concentrations (an HPLC fraction of C2F at concentrations of 190 μg/mL), fractions F1-F9—excluding F7 (F1-F9—exc F7; HPLC fractions of C2F at concentrations of 163 μg/mL), combination of F1-F9—excluding F7 along with F7 measured as level of IL-8 on HCT116 cells, with and without antagonists to CB1, CB2, and GPR55 receptors (antagonists at a concentration of 20 μM, CB1, CB1 receptor antagonist rimonabant; CB2, CB2 receptor antagonist SR144528; GPR55, GPR55 antagonist CID16020046). HCT116 cells were seeded (50,000 per well) in triplicate in 500 μL, growing media and incubated for 24 hours at 37_° C. in a humidified 5% CO2-95% air atmosphere. Cells were treated with 300 ng/mL TNF-α and 50 μL of *C. sativa* ethanol extract of C2F fractions for 4 hours. Treatments with F7, F1-F9, and combination of fractions without antagonists served as a positive control (Con). Non-treated are the cells without TNF-α and treatments. Levels of IL-8 were measured from the supernatant using a commercial kit. Values (ng/mL) were calculated relative to control.

Figure 8:
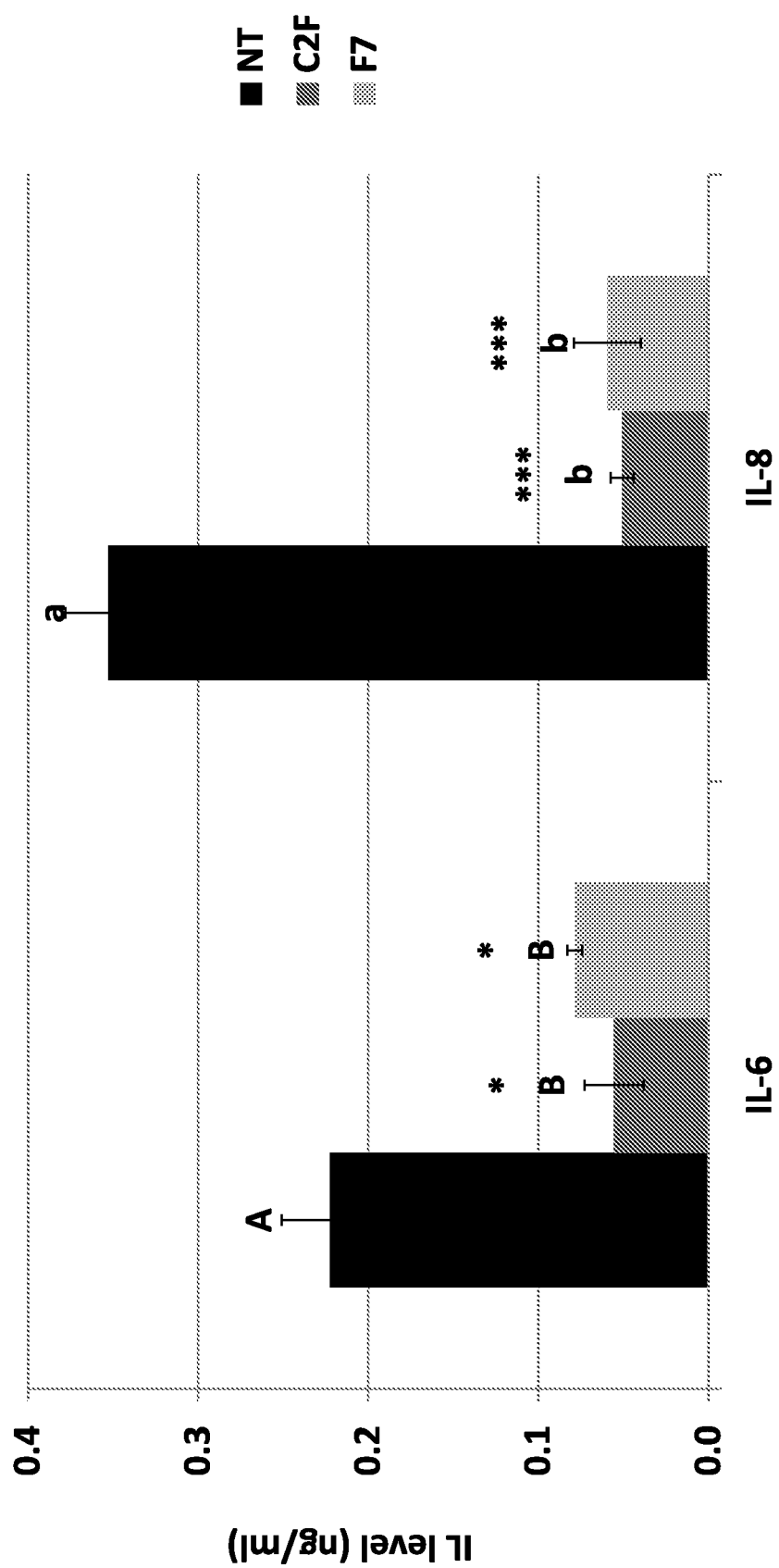

FIG. 8 depicts the anti-inflammatory activity of *C. sativa* fresh flowers ethanol extracts (C2F, 0.2 mg/ml) and F7 (0.08 mg/ml) measured as level of IL-8 and IL-6 from biopsies of Intestine Bowel Disease (IBD) patients. Biopsies from inflamed and normal tissue were taken and processed in tissue culture media and then treated with C2F (n=29), F7 (n=9) and non-treated controls (n=29) for 16 hours. Levels of IL-8 and IL-6 were measured from the supernatant using a commercial kit. Error bars indicate ±SEM. *, , * indicates data statistically significantly different in comparison with the control (Non-treated tissues) at $p \leq 0.05$, $p \leq 0.001$, $p \leq 0.0001$ respectively. Levels with different letters are significantly different from all combinations of pairs by turkey HSD.

Figure 9A:
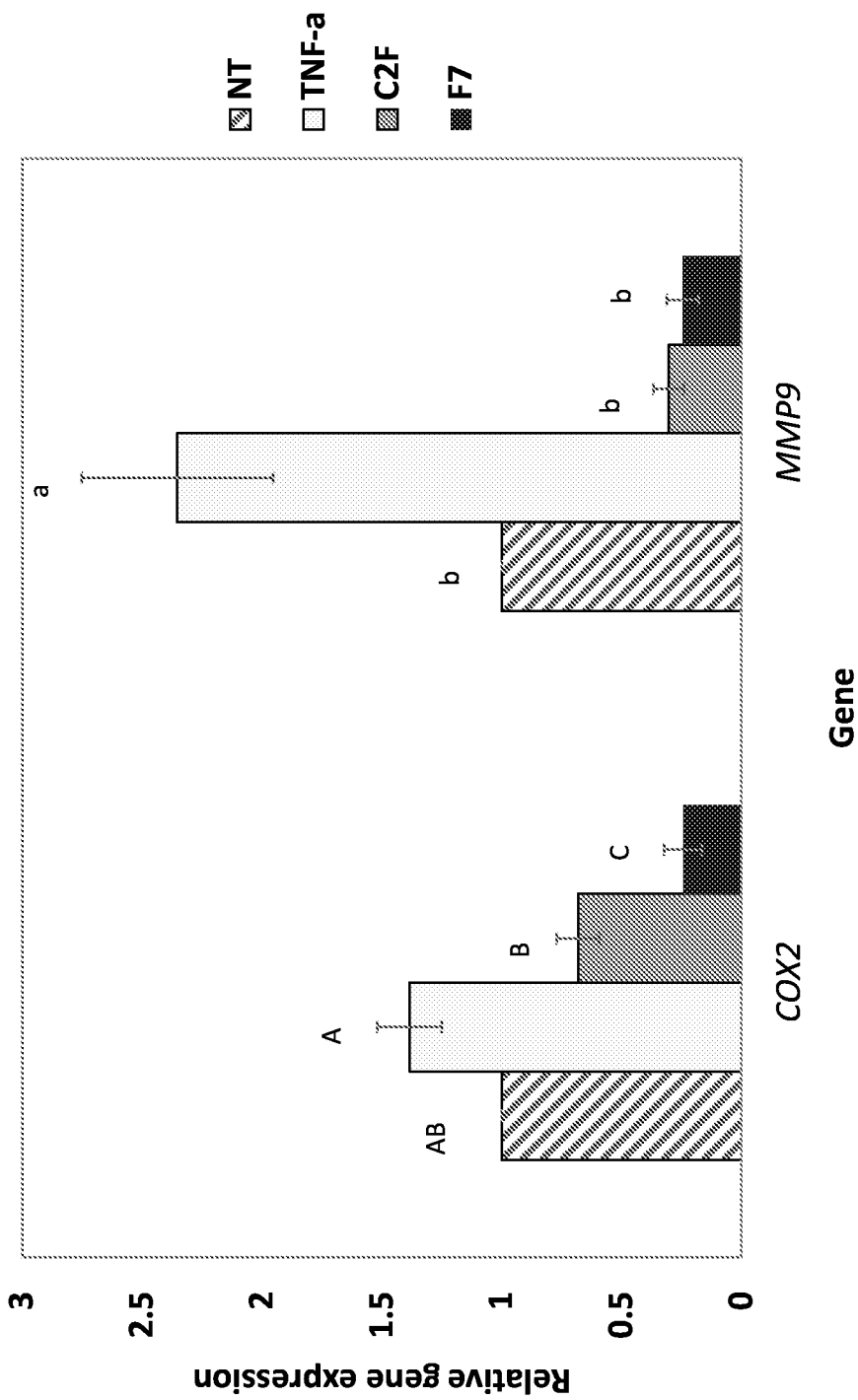
Figure 9B:
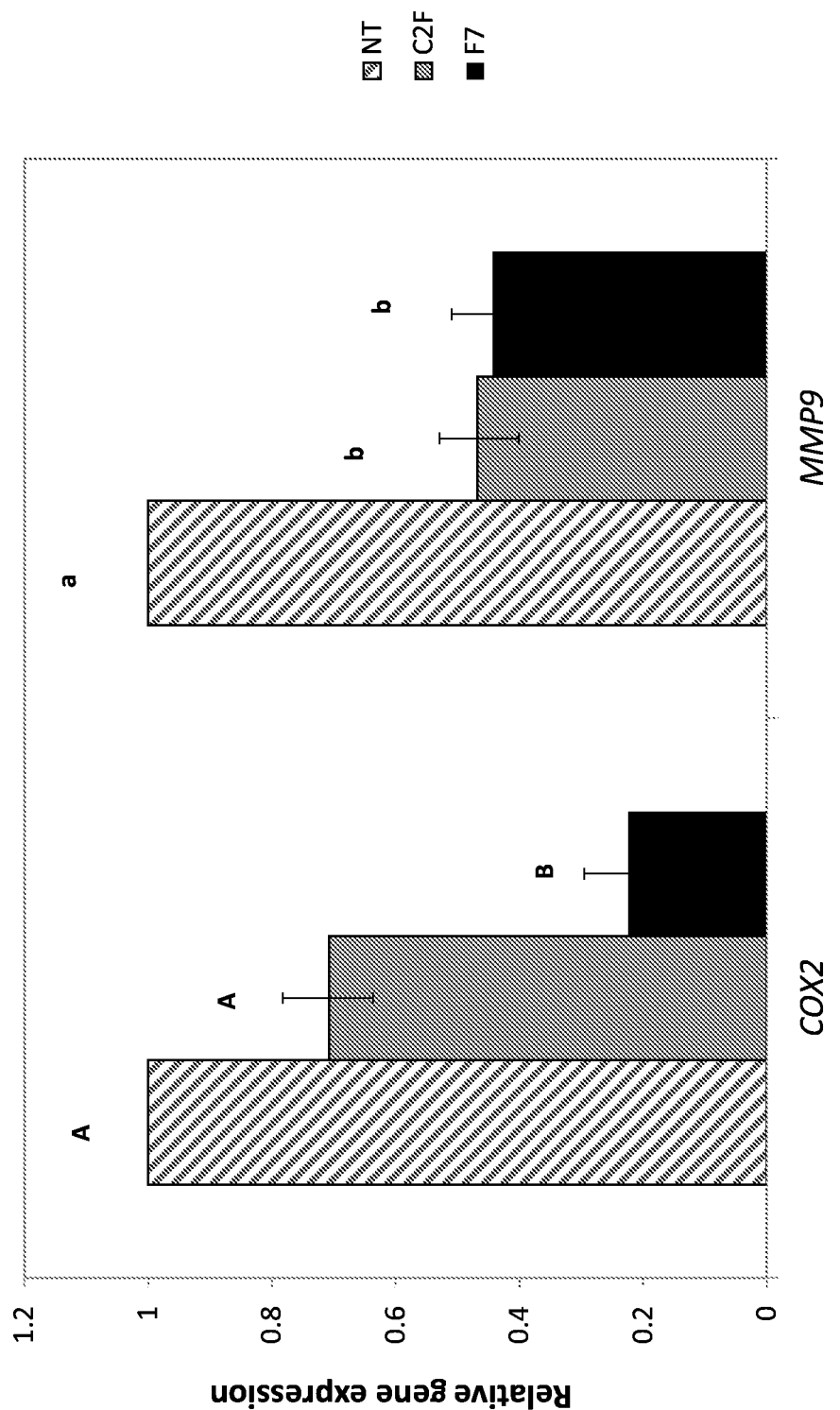

FIGS. 9A-B depicts COX2 and MMP9 gene expression. (FIG. 9A) HCT116 cell line. Cells were seeded (1,500,000 per well) in triplicate in 500 μL, growing media and incubated for 24 hours at 37° C. in a humidified 5% $CO_2$-95% air atmosphere. Cells were treated with 50 ng/mL TNF-α overnight and then treated with *C. sativa* C2F or F7 added 5 hours before RNA extraction. (FIG. 9B) Biopsies. C2F and F7 were added overnight to four UC patients and one CD patient biopsies at concentrations of 0.2 mg/mL and 0.07 mg/mL, respectively. RNA was extracted and reverse transcribed, and values of the steady-state level of gene transcripts were determined as the ratio between the target gene (COX2 or MMP9) and a reference gene (GAPDH), and that of treatment vs. no treatment (NT), using the 2-ΔΔCT method. The experiment was performed in three biological replicates, with three technical repeats for each (n=3). SE was calculated for three biological replicates for each examined treatment. Different letters above bars indicate statistically significant differences between means by one-way analysis of variance (ANOVA) with Tukey-Kramer multiple comparison test (P<0.01).

Figure 10:
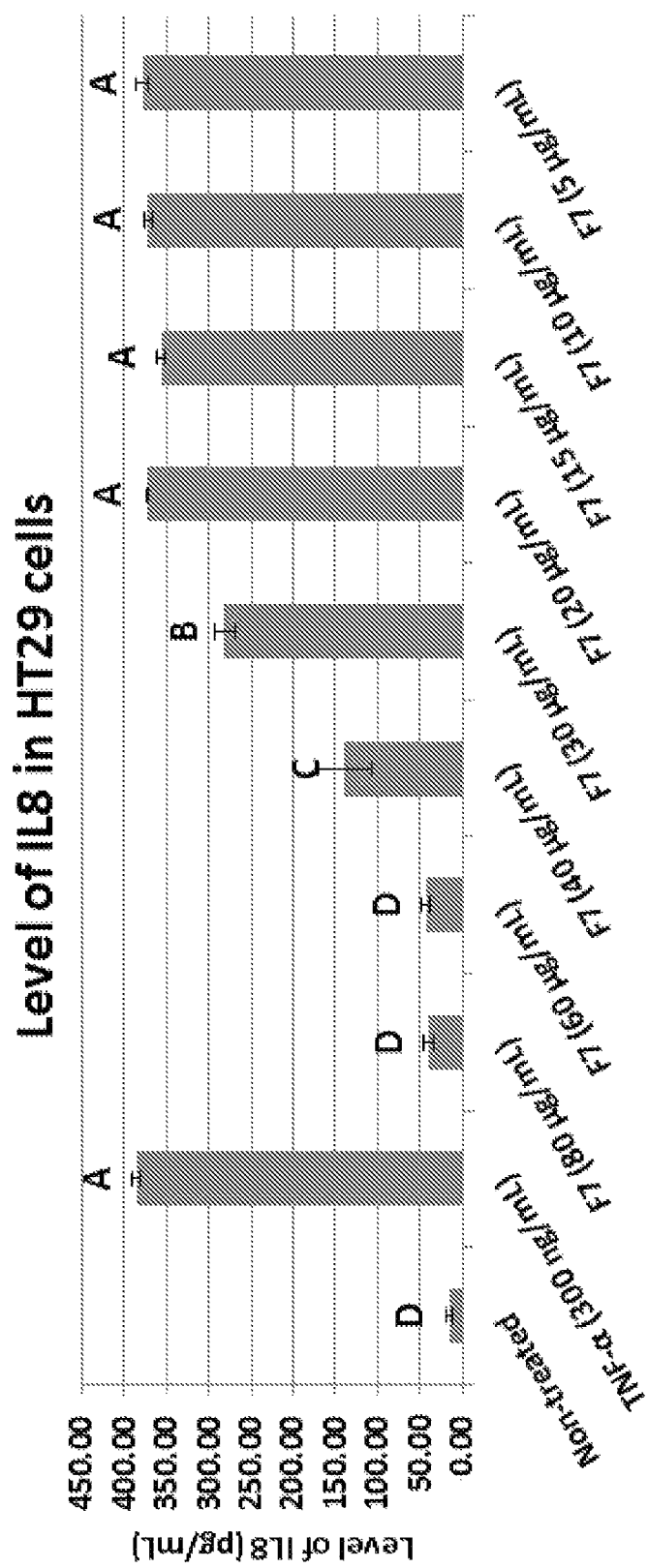

FIG. 10 depicts anti-inflammatory (ELISA) assay on HT29 cells treated with different concentrations of fraction 7 of *C. sativa* fresh flower extract (F7) measured as level of IL-8 on HT29 cells. F7 from *C. sativa* fresh flowers ethanol extracts was diluted to 80, 60, 40, 30, 20 15, 10 and 5 μg/ml. HT29 cells were seeded (50,000 per well) in triplicate in 500 μL growing media and incubated for 24 hours at 37° C. in a humidified 5% $CO_2$-95% air atmosphere. Cells were treated with 50 ng/mL TNF-α and F7 for 16 hours. Levels of IL-8 were measured from the supernatant using a commercial kit. Values (ng/mL) were calculated relative to a TNF-α treated control. Non-treated are the cells without TNF-α and treatments. Error bars indicate ±SEM (n=3). Levels with different letters are significantly different from all combinations of pairs by turkey HSD.

FIG. 11 depicts anti-inflammatory (ELISA) assay on HT29 cells treated with different concentrations of CBD, measured as level of IL-8 on HT29 cells. CBD dissolved in methanol—at concentration of ~5 mM was diluted to 80, 60, 40, 30, 20 15, 10 and 5 µM/ml. HT29 cells were seeded (50,000 per well) in triplicate in 500 µL, growing media and incubated for 24 hours at 37° C. in a humidified 5% $CO_2$-95% air atmosphere. Cells were treated with 50 ng/mL TNF-α and CBD for 16 hours. Levels of IL-8 were measured from the supernatant using a commercial kit. Values (ng/mL) were calculated relative to a TNF-α treated control. Non-treated are the cells without TNF-α and treatments. Error bars indicate ±SEM (n=3). Levels with different letters are significantly different from all combinations of pairs by turkey HSD.

FIG. 12 depicts anti-inflammatory (ELISA) assay on HT29 cells treated with different concentrations of THC, measured as level of IL-8 on HT29 cells. THC dissolved in methanol—at concentration of ~5 mM was diluted to 75, 50, 25 and 12.5 µM/ml. HT29 cells were seeded (50,000 per well) in triplicate in 500 µL, growing media and incubated for 24 hours at 37° C. in a humidified 5% $CO_2$-95% air atmosphere. Cells were treated with 50 ng/mL TNF-α and THC for 16 hours. Levels of IL-8 were measured from the supernatant using a commercial kit. Values (ng/mL) were calculated relative to a TNF-α treated control. Non-treated are the cells without TNF-α and treatments. Error bars indicate ±SEM (n=3). Levels with different letters are significantly different from all combinations of pairs by turkey HSD.

Figure 13C:
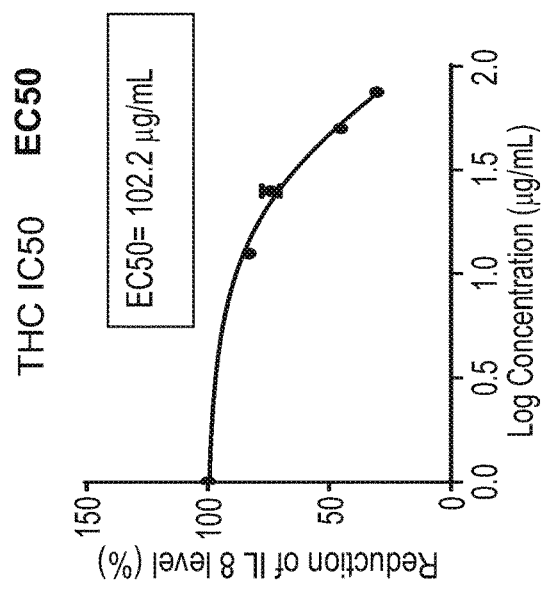
Figure 13B:
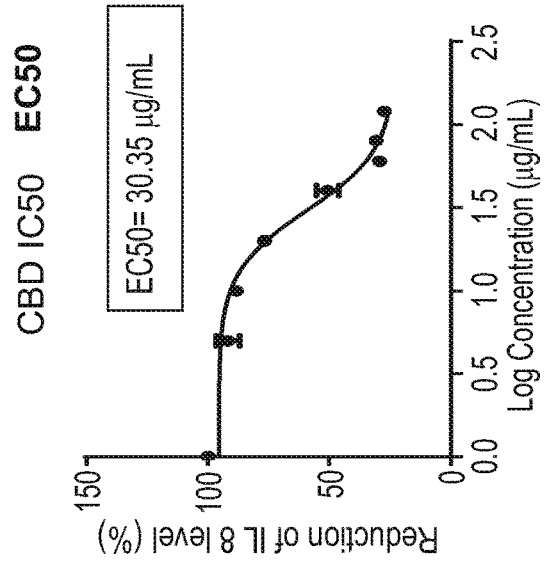
Figure 13A:
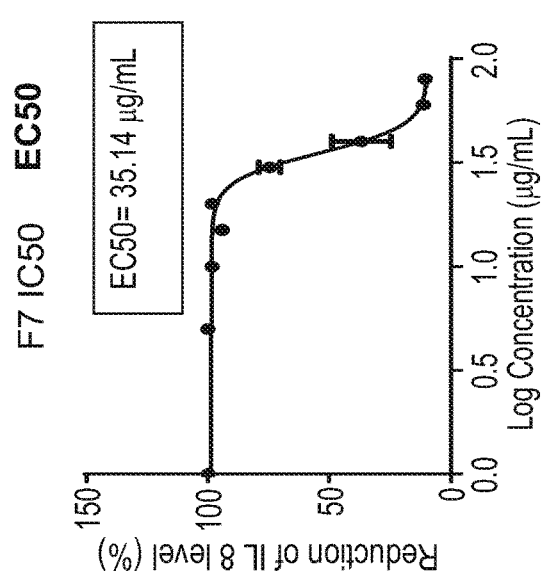

FIGS. 13A-C depict $EC_{50}$ dose of fractions on HCT116 cells. (FIG. 13A) Fraction 7 (F7), (FIG. 13B) CBD and (FIG. 13C) THC. Dose-effect curves of F7, CBD or THC on IL-8 levels of HCT116 colon cancer cells. HCT116 cells were seeded (50,000 per well) in triplicate in 500 µL, growing media and incubated for 24 hours at 37° C. in a humidified 5% $CO_2$-95% air atmosphere. Cells were treated with 50 ng/mL TNF-α and F7, CBD or THC for 16 hours. Levels of IL-8 were measured from the supernatant using a commercial kit. Values (ng/mL) were calculated relative to a TNF-α treated control. Non-treated are the cells without TNF-α and treatments. For dose response assays, data points were connected by non-linear regression lines of the sigmoidal dose-response relation. GraphPad Prism was employed to produce dose-response curve and $EC_{50}$ doses.

Figure 14:
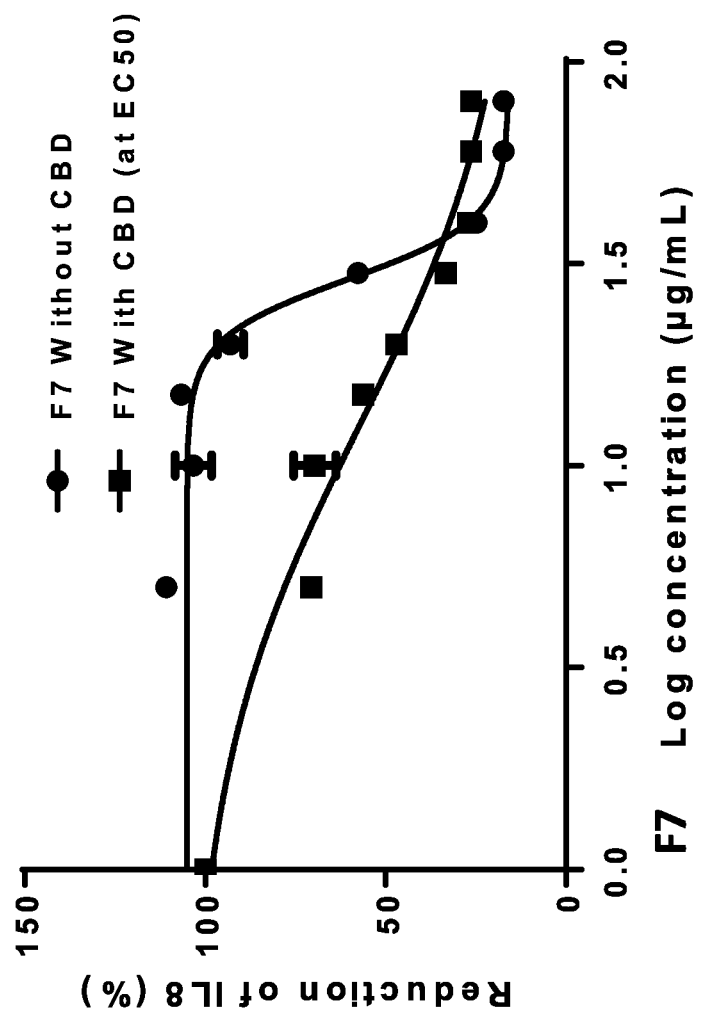

FIG. 14 depicts EC50 of F7 with and without CBD at its $EC_{50}$ dose on HT29 cells. Dose-effect curves of F7 with and without CBD on IL-8 levels of HT29 colon cancer cells. HT29 cells were seeded (50,000 per well) in triplicate in 500 µL, growing media and incubated for 24 hours at 37° C. in a humidified 5% $CO_2$-95% air atmosphere. Cells were treated with 300 ng/mL TNF-α and F7 (at EC50 concentration) with and without CBD at different concentrations for 4 hours. Levels of IL-8 were measured from the supernatant using a commercial kit. Values (ng/mL) were calculated relative to a TNF-α treated control. Non-treated are the cells without TNF-α and treatments. For dose response assays, data points were connected by non-linear regression lines of the sigmoidal dose-response relation. GraphPad Prism was employed to produce dose-response curves.

Figure 15:
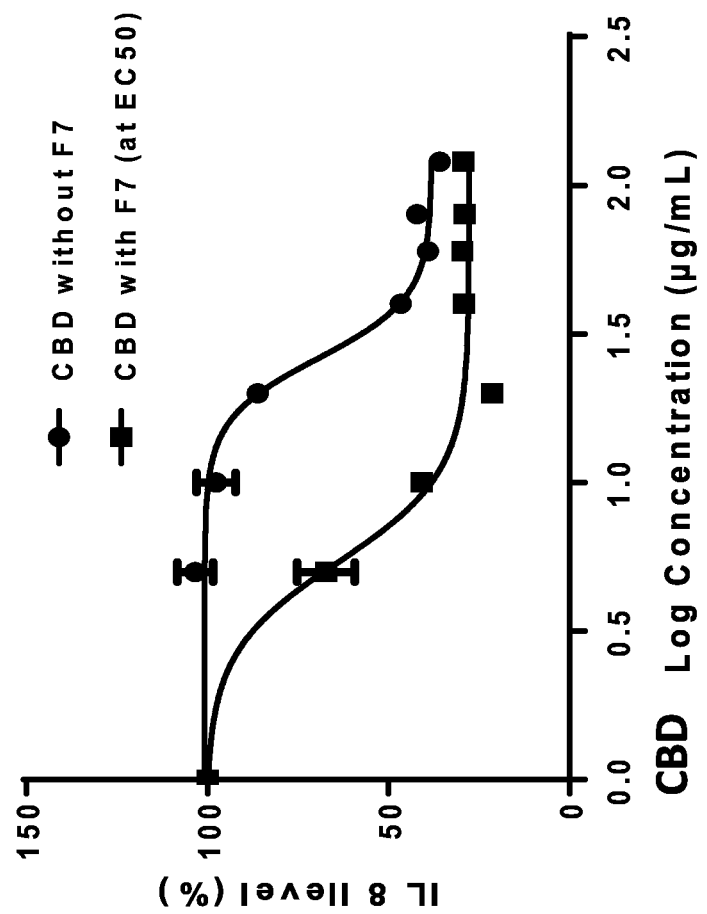

FIG. 15 depicts EC50 of CBD with and without F7 at its EC50 dose on HT29 cells. Dose-effect curves of CBD with and without F7 on IL-8 levels of HT29 colon cancer cells. HT29 cells were seeded (50,000 per well) in triplicate in 500 µL, growing media and incubated for 24 hours at 37° C. in a humidified 5% $CO_2$-95% air atmosphere. Cells were treated with 300 ng/mL TNF-α and CBD (at EC50 concentration) with and without F7 at different concentrations for 4 hours. Levels of IL-8 were measured from the supernatant using a commercial kit. Values (ng/mL) were calculated relative to a TNF-α treated control. Non-treated are the cells without TNF-α and treatments. For dose response assays, data points were connected by non-linear regression lines of the sigmoidal dose-response relation. GraphPad Prism was employed to produce dose-response curves.

DESCRIPTION OF SPECIFIC EMBODIMENTS OF THE INVENTION

The present invention, in some embodiments thereof, relates to compositions and methods for treating inflammatory diseases.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Inflammatory bowel diseases (IBDs), Crohn's disease (CD) and ulcerative colitis (UC), are characterized by chronic intestinal inflammation. Different preparations of marijuana (*Cannabis sativa*) have been shown to have beneficial effects for IBD patients. However, *C. sativa* extracts contain hundreds of compounds.

The present inventor has now uncovered that liquid chromatography fractions of cannabis inflorescence extracts are effective in reducing inflammation.

Specifically, the anti-inflammatory activity of *C. sativa* inflorescence extracts was tested on epithelial cells, colon cells and colon tissues. It was shown that the anti-inflammatory activity of cannabis flower extracts derives from Δ9-tetrahydrocannabinolic acid (THCA). *C. sativa* polar extracts had a significant anti-inflammatory activity (see Example 1 of the Examples section which follows). This activity was also observed for fraction F7 which comprises mainly of THCA (see Examples 3, 5 and 12 of the Examples section which follows). However, *C. sativa* whole extract has an increased activity over THCA only (see Example 6 of the Examples section which follows). Also, while CBD exhibited only minor anti-inflammatory activity in the examined assays (see Example 4 of the Examples section which follows), synergistic activity was evident when combining treatment with fraction F7 and CBD, or with THCA and CBD (see Example 10 of the Examples section which follows). Activity of the extract and active fraction (fraction F7) was verified on colon tissues taken from IBD patients (see Example 8, of the Examples section which follows), and was shown to suppress COX2 and MMP9 gene expression in both cell culture and colon tissue (see Example 9, of the Examples section which follows). The present inventors therefore propose that the cannabis extracts may be used in the treatment of inflammatory diseases.

Thus, according to one aspect of the present invention, there is provided a method of generating an anti-inflammatory composition, the method comprising: (i) adding a polar solvent to a dry Cannabis inflorescence so as to obtain a crude extract; (ii) filtering the ethanol crude extract so as to obtain a filtered extract; (iii) fractionating the filtered extract on a high pressure liquid chromatography (HPLC); (iv) collecting at least one fraction comprising active ingredients detectable by a detector operated at 220 nm.

*Cannabis* is a genus of flowering plants in the family Cannabaceae that includes three different species, *Cannabis sativa, Cannabis indica* and *Cannabis ruderalis*. The term *Cannabis* encompasses wild type *Cannabis* and also variants thereof, including cannabis chemovars which naturally contain different amounts of the individual cannabinoids. For example, some *Cannabis* strains have been selectively bred to produce high or low levels of THC and other cannabinoids. Accordingly, *Cannabis* cultivars that are rich in THCA can be used in accordance with the present teachings.

According to one embodiment, the *Cannabis* plant is a wild-type plant.

According to one embodiment, the *Cannabis* plant is transgenic.

According to one embodiment, the *Cannabis* plant is genomically edited.

According to one embodiment, the *Cannabis* plant is *Cannabis sativa* (*C. sativa*).

The extract may be derived from a cultivated *Cannabis* plant (i.e. not grown in their natural habitat) or may be derived from *Cannabis* plants which grow in the wild.

The tissue of the *Cannabis* plant from which the extract is typically obtained is the inflorescence. Accordingly, the extract may be obtained from the complete flower head of a plant including stems, stalks, bracts, and flowers. However, it will be appreciated that a cannabis extract of the invention may be obtained from only part of the inflorescence, such as from the bracts and/or flowers.

According to one embodiment, the extract is obtained from a fresh plant (i.e. a plant not heated prior to the extraction process). Fresh plants include plants taken immediately following harvesting (e.g., up to an hour or several hours) for extraction as well as plants frozen immediately after harvesting (e.g. at about −70° C. to −90° C., e.g. at −80° C., for any required length of time) prior to extraction.

According to one embodiment, the extract is obtained from fresh inflorescence.

According to one embodiment, the extract is obtained from a frozen inflorescence (e.g. frozen immediately after harvesting at about −70° C. to −90° C., e.g. at −80° C., for any required length of time). Thus, for example, the extract may be obtained from a cryopreserved inflorescence, or from an inflorescence frozen in liquid nitrogen or in dry ice.

According to one embodiment, the extract is obtained from an inflorescence which has not been subjected to heating (such as heating at e.g. at 120° C. to 180° C., e.g. at 150° C., for any length of time, such as for 1-5 hours).

According to one embodiment, the extract is obtained from dry *Cannabis* inflorescence. Drying the inflorescence may be carried out using any method known in the art, such as by pulverizing with liquid nitrogen or with dry-ice/alcohol mixture.

In some embodiments, the polar solvent comprises a polar, protic solvent (e.g., ethanol or methanol). In some embodiments, the polar solvent comprises a polar, aprotic solvent (e.g., acetone). Polar solvents suitable for use with the present invention include, but are not limited to, ethanol, methanol, n-propanol, iso-propanol, a butanol, a pentanol, acetone, methylethylketone, ethylacetate, acetonitrile, tetrahydrofuran, dimethylformamide, dimethylsulfoxide, water, and combinations thereof.

In a particular embodiment, the polar solvent is ethanol (e.g. absolute ethanol, i.e. above 99.8%, or in the range of 99-70% in water).

The concentration or amount of a polar solvent used to dry *Cannabis* inflorescence can be varied. Generally, the ratio of a dry *Cannabis* inflorescence to a polar solvent (weight to volume) is the amount of a polar solvent sufficient to extract about 70% or more, about 75% or more, about 85% or more, about 90% or more, about 95% or more, about 97% or more, or about 99% or more of a composition having anti-inflammatory activity. In some embodiments, the ratio of polar solvent to dry *Cannabis* inflorescence is about 1:2 to about 1:20 (w/v), e.g. about 1:4 to about 1:10 (w/v).

In particular embodiments, the extract is an ethanol extract.

In particular embodiments, absolute ethanol is added to the dry inflorescence at a sample-to-absolute ethanol ratio of 1:4 (w/v).

In some embodiments, the dry *Cannabis* inflorescence is contacted with a polar solvent (e.g. ethanol) for about 15 minutes or more, about 30 minutes or more, about 1 hour or more, about 2 hours or more, or about 5 hours or more.

Temperature can also be controlled during the contacting. In some embodiments, the dry *Cannabis* inflorescence is contacted with a polar solvent at temperature of about 15° C. to about 35° C., or about 20° C. to about 25° C.

According to a specific embodiment, the dry Cannabis inflorescence is contacted with a polar solvent (e.g. ethanol) while being constantly mixed e.g. on a shaker.

In some embodiments, the process of the present invention comprises isolating a liquid extract (i.e. filtered extract) from the mixture (i.e. crude extract) comprising the liquid extract and solids. Suitable means for isolating the liquid extract (i.e. filtered extract) include those known in the art of organic synthesis and include, but are not limited to, gravity filtration, suction and/or vacuum filtration, centrifuging, setting and decanting, and the like. In some embodiments, the isolating comprises filtering a liquid extract through a porous membrane, syringe, sponge, zeolite, paper, or the like having a pore size of about 1-5 µm, about 0.5-5 µm, about 0.1-5 µm, about 1-2 µm, about 0.5-2 µm, about 0.1-2 µm, about 0.5-1 µm, about 0.1-1 µm, about 0.25-0.45 µm, or about 0.1-0.5 µm (e.g. about 2 µm, about 1 µm, about 0.45 µm, or about 0.25 µm).

According to a specific embodiment, the crude extract is filtered through a 0.45-µm syringe filter such as that commercially available from Merck, Darmstadt, Germany.

The present inventors contemplate drying (i.e. removal of the polar solvent) and/or freezing the filtered extract following generation thereof.

The method for drying the filtered extract (i.e. removing the polar solvent) is not particularly limited, and can include solvent evaporation at a reduced pressure (e.g., sub-atmospheric pressure) and/or an elevated temperature (e.g., above about 25° C.). In some embodiments, it can be difficult to completely remove a polar solvent from a liquid extract by standard solvent removal procedures such as evaporation. In some embodiments, processes such as co-evaporation, lyophilization, and the like can be used to completely remove the polar solvent from a liquid fraction to form a dry powder, dry pellet, dry granulate, paste, and the like. According to a specific embodiment the polar solvent is evaporated with a vacuum evaporator.

Following generation of the filtered extract, the present inventors further contemplate additional purification steps so as to further purify active agents from the extract.

Thus, for example, the present inventors further propose fractionating the filtered extract. Fractionating can be performed by processes such as, but not limited to: column chromatography, preparative high performance liquid chromatography ("HPLC"), reduced pressure distillation, and combinations thereof. According to a specific embodiment, fractionating is performed by HPLC.

In some embodiments, fractionating comprises resuspending the filtered extract in a polar solvent (such as methanol, as discussed above), applying the polar extract to a separation column, and isolating the Cannabis extract having anti-inflammatory activity by column chromatography.

An eluting solvent is applied to the separation column with the polar extract to elute fractions from the polar extract. Suitable eluting solvents for use include, but are not limited to, methanol, ethanol, propanol, acetone, acetic acid, carbon dioxide, methylethyl ketone, acetonitrile, butyronitrile, carbon dioxide, ethyl acetate, tetrahydrofuran, di-isopropylether, ammonia, triethylamine, N,N-dimethylformamide, N,N-dimethylacetamide, and the like, and combinations thereof.

According to an alternative or an additional embodiment, liquid chromatography comprises high performance liquid chromatography (HPLC).

According to an alternative or an additional embodiment, liquid chromatography is performed on a reverse stationary phase.

According to an alternative or an additional embodiment, liquid chromatography is performed using a mobile phase comprising from 10 to 30% acidic aqueous solution and from 90 to 70% alcohol.

According to a specific embodiment, an eluting solvent comprises 15% solvent A (0.1% acetic acid in water) and 85% solvent B (methanol).

According to an alternative or an additional embodiment, fraction separation may be carried out on a HPLC comprising a stationary phase comprising RP-18 end capped column (such as a 250 mm×4.6 mm available from e.g. Merck KGaA, Darmstadt, Germany) with a guard column (e.g. 4 mm×4 mm), and a mobile phase of 15% solvent A (0.1% acetic acid in water) and 85% solvent B (methanol) at a flow rate of 1.5 mL/min for 28-35 minutes.

According to an alternative or an additional embodiment, fractions comprising components (active ingredients) are detectable by a detector operated at 220 nm are collected.

According to an alternative or an additional embodiment, the detector is a diode array detector.

According to an alternative or an additional embodiment, the detector is a DAD-300 detector.

According to a specific embodiment, the conditions for HPLC include, for example, an UltiMate 3000 HPLC system coupled with WPS-3000(T) Autosampler, HPG-3400 pump, and DAD-300 detector, a Purospher RP-18 end capped column (such as a 250 mm×4.6 mm available e.g. from Merck KGaA, Darmstadt, Germany) with a guard column (e.g. 4 mm×4 mm), and a mobile phase of 15% solvent A (0.1% acetic acid in water) and 85% solvent B (methanol) at a flow rate of 1.5 mL/min for 28-35 minutes.

The extracts and/or fractions obtained may be tested for anti-inflammatory activity and/or for cytotoxic activity.

Exemplary methods for testing the above mentioned activities are described herein below as well as in the Examples section which follows.

For testing the effect of the extracts and/or fractions on inflammation, any in-vivo, in-vitro or ex-vivo assay known in the art for testing anti-inflammatory activity may be used. For example, in-vitro and ex-vivo assays may be used which analyze the effect of the extracts and/or fractions on cell derived factors such as IL-8, IL-6, IFN-gamma, leukotriene B4, nitric oxide, prostaglandins, TNF-alpha and IL-1. For these, common ELISA assays may be used. Additionally or alternatively, in-vitro or ex-vivo assays may be used which analyze the effect of extracts and/or fractions on expression of genes associated with inflammation in cells. Such genes include, but are not limited to, COX2 expression (reviewed by [24]) and MMP9 (reviewed by [25]).

For testing the effect of the extracts and/or fractions on cytotoxic activity, any in-vivo, in-vitro or ex-vivo assay known in the art for testing cytotoxic activity may be used. For example, cell viability assay on cancer cells (e.g. colon cancer cells) as discussed in detail in the examples section which follows.

The extracts and/or fractions of the present invention can also be characterized by analytical methods such as, but not limited to, spectroscopic methods such as, but not limited to, ultraviolet-visible spectroscopy ("UV-Vis"), infrared spectroscopy ("IR"), and the like; mass-spectrometry ("MS") methods such as, but not limited to, time-of-flight MS; quadrupole MS; electrospray MS, Fourier-transform MS, Matrix-Assisted Laser Desorption/Ionization ("MALDI"), and the like; chromatographic methods such as, but not limited to, gas-chromatography ("GC"), liquid chromatograph ("LC"), high-performance liquid chromatography ("HPLC"), and the like; and combinations thereof (e.g., GC/MS, LC/MS, HPLC/UV-Vis, and the like), and other analytical methods known to persons of ordinary skill in the art.

According to an alternative or an additional embodiment, the extracts and/or fractions obtained by the methods of some embodiments of the invention are kept frozen e.g. in a freezer, until further use (e.g. at about −20° C. to −90° C., at about −70° C. to −90° C., e.g. at −80° C.), for any required length of time.

According to an alternative or an additional embodiment, the extracts and/or fractions obtained by the methods of some embodiments of the invention are immediately used (e.g. within a few minutes e.g., up to 30 minutes).

The extracts and/or fractions obtained by the methods of some embodiments of the invention may be used separately. Alternatively, different extracts (e.g. from different plants or from separate extraction procedures) may be pooled together. Likewise, different fractions (from the same extract, from different extracts, from different plants and/or from separate extraction procedures) may be pooled together.

The term "pooled" as used herein refers to collected from the liquid chromatography (e.g. HPLC) either as a single fraction or a plurality of fractions.

According to a specific embodiment, different fractions are obtained from a single extract of Cannabis inflorescence, by subjecting the cannabis extract to liquid chromatography and collecting fractions comprising ingredients that are detectable by a detector operated at 220 nm (as discussed in detail herein above). Thus, for examples, fractions may be obtained at the following retention times when the following conditions are used: HPLC comprise an UltiMate 3000 HPLC system coupled with WPS-3000(T) Autosampler, HPG-3400 pump, and DAD-300 detector, a Purospher RP-18 end capped column a mobile phase of 15% solvent A (0.1% acetic acid in water) and 85% solvent B (methanol) at a flow rate of 1.5 mL/min: F1—retention time 0-5 minutes, F2—retention time 5-9 minutes, F3—retention time 9-12 minutes, F4—retention time 12-14.5 minutes, F5—retention time 18-20, F6—retention time 24-26, F7—retention time 28-35 minutes, F8—retention time 35-37, F9—retention time 37-40

According to an alternative or an additional embodiment, at least two, at least three, at least four, at least five, at least six, at least seven, at least eight or more of the fractions may be pooled together, at any combination thereof.

According to one embodiment, the fraction comprises THCA.

As used herein, the term "THCA" refers to Δ9-tetrahydrocannabinolic acid, the precursor of tetrahydrocannabinol (THC). The term THCA as used herein encompasses native THCA (i.e. originating from the Cannabis plant), or synthetic analogs or derivatives thereof. Any THCA analog may be used in accordance with the present teachings as long as it comprises an anti-inflammatory activity (alone, or as part of the composition discussed herein).

The term "analog" refers to a structural derivative having at least the same anti-inflammatory activity. The analog may be synthetic or naturally occurring.

Exemplary THCA analogs include, but are not limited to, 11-OH-delta9-THCA-A and 11-Nor-delta9-THCA-A carboxylic acid [as discussed in detail in Guillermo Moreno-Sanz, Critical Review and Novel Therapeutic Perspectives of D9-Tetrahydrocannabinolic Acid A, Cannabis and Cannabinoid Research Volume 1.1, (2016)].

According to an alternative or an additional embodiment, the extracts and/or fractions comprise at least about 75-95% THCA, at least about 80-90% THCA, at least about 80-95% THCA, at least about 80-100% THCA, or at least about 90-100% THCA.

According to an alternative or an additional embodiment, the extracts and/or fractions comprise at least about 60% THCA, at least about 65% THCA, at least about 70% THCA, at least about 75% THCA, at least about 80% THCA, at least about 81% THCA, at least about 82% THCA, at least about 83% THCA, at least about 84% THCA, at least about 85% THCA, at least about 86% THCA, at least about 87% THCA, at least about 88% THCA, at least about 89% THCA, at least about 90% THCA, at least about 91% THCA, at least about 92% THCA, at least about 93% THCA, at least about 94% THCA, at least about 95% THCA, at least about 96% THCA, at least about 97% THCA, at least about 98% THCA, at least about 99% THCA, or about 100% THCA.

According to a specific embodiment, the cannabis extracts or fractions comprise 75% or more THCA.

According to a specific embodiment, the cannabis extracts or fractions comprise 80% or more THCA.

According to a specific embodiment, the cannabis extracts or fractions comprise 85% or more THCA.

According to a specific embodiment, the cannabis extracts or fractions comprise 95% or more THCA.

According to an alternative or an additional embodiment, the extracts and/or fractions comprise cannabis derived active ingredients other than the THCA.

According to an alternative or an additional embodiment, the extracts and/or fractions comprise at least one of D-Limonene, β-Caryophyllene, Humulene, malic acid, α-Farnesene, cannabinol (CBN), Δ9-tetrahydrocannabinol (THC), and/or cannabigerol (CBG).

According to an alternative or an additional embodiment, the extracts and/or fractions comprise at least two, at least three, at least four, at least five, at least six, at least seven of D-Limonene, β-Caryophyllene, Humulene, malic acid, α-Farnesene, cannabinol (CBN), Δ9-tetrahydrocannabinol (THC), and/or cannabigerol (CBG).

According to an alternative or an additional embodiment, the extracts and/or fractions comprise D-Limonene, β-Caryophyllene, Humulene, malic acid, α-Farnesene, cannabinol (CBN), Δ9-tetrahydrocannabinol (THC), and cannabigerol (CBG).

According to an alternative or an additional embodiment, the extracts and/or fractions comprise THCA and any one, two, three, four, five, six or seven of D-Limonene, β-Caryophyllene, Humulene, malic acid, α-Farnesene, cannabinol (CBN), Δ9-tetrahydrocannabinol (THC), and/or cannabigerol (CBG).

According to an alternative or an additional embodiment, the extracts and/or fractions comprise THCA, D-Limonene, β-Caryophyllene, Humulene, malic acid, α-Farnesene, cannabinol (CBN), Δ9-tetrahydrocannabinol (THC), and cannabigerol (CBG).

According to an alternative or an additional embodiment, any one of D-Limonene, β-Caryophyllene, Humulene, malic acid, α-Farnesene, cannabinol (CBN), Δ9-tetrahydrocannabinol (THC), and/or cannabigerol (CBG) may be provided as a synthetic analog.

According to an alternative or an additional embodiment, the extracts and/or fractions comprise components as listed in Table 6, herein below.

According to an alternative or an additional embodiment, the extracts and/or fractions of some embodiments of the invention comprise at least one, two, three, four, five, six, seven, eight, nine, ten or more components as listed in Table 6.

According to an alternative or an additional embodiment, the extracts and/or fractions of some embodiments of the invention comprise THCA as well as at least one, two, three, four, five, six, seven, eight, nine, ten or more components as listed in Table 6.

The present invention is also directed to a product prepared by the process of the present invention. In some embodiments, there is provided an anti-inflammatory composition obtainable by the method of some embodiments of the invention.

According to aspect of the invention, there is provided a composition comprising liquid chromatography pooled fractions of cannabis extract comprising active ingredients detectable by a detector operated at 220 nm, the active ingredients comprising THCA (at a level such as described hereinabove).

According to an aspect of the invention, there is provided a composition comprising liquid chromatography-purified cannabis fraction obtainable by subjecting the cannabis extract to liquid chromatography and collecting fractions detectable by a detector operated at 220 nm.

According to one embodiment, the composition is characterized by: (i) having a cytotoxic activity on cancer cells (ii) reducing the level of pro-inflammatory cytokine secretion by cells; and/or (iii) reducing the level of MMP9 and COX2 expression in cells (e.g. inflammatory cells).

According to aspect of the invention, there is provided a composition comprising liquid chromatography pooled fractions of cannabis extract comprising active ingredients detectable by a detector operated at 220 nm, the composition being characterized by: (i) having a cytotoxic activity on cancer cells; (ii) reducing the level of pro-inflammatory cytokine secretion by cells; and/or (iii) reducing the level of MMP9 and COX2 expression in cells (e.g. inflammatory cells).

According to an alternative or an additional embodiment, the composition comprises THCA (e.g. as an active ingredient).

According to an alternative or an additional embodiment, the composition comprises at least about 75-95% THCA, at least about 80-90% THCA, at least about 80-95% THCA, at least about 80-100% THCA, or at least about 90-100% THCA.

According to an alternative or an additional embodiment, the composition comprises at least about 60% THCA, at least about 65% THCA, at least about 70% THCA, at least about 75% THCA, at least about 80% THCA, at least about 81% THCA, at least about 82% THCA, at least about 83% THCA, at least about 84% THCA, at least about 85% THCA, at least about 86% THCA, at least about 87% THCA, at least about 88% THCA, at least about 89% THCA, at least about 90% THCA, at least about 91% THCA, at least about 92% THCA, at least about 93% THCA, at least about 94% THCA, at least about 95% THCA, at least about 96% THCA, at least about 97% THCA, at least about 98% THCA, at least about 99% THCA, or about 100% THCA.

According to a specific embodiment, the composition comprises 75% or more THCA.

According to a specific embodiment, the composition comprises 80% or more THCA.

According to a specific embodiment, the composition comprises 85% or more THCA.

According to a specific embodiment, the composition comprises 95% or more THCA.

In cases wherein the composition does not intrinsically comprise the required level of THCA, the composition may be supplemented with THCA (e.g. from pooled fractions, from THCA synthetic analogs, as discussed above).

According to an alternative or an additional embodiment, the composition comprising THCA (as an active ingredient) may comprise a dose range of THCA of 0.1-1000 mg/ml, 0.1-100 mg/ml, 0.1-50 mg/ml, 0.1-10 mg/ml, 0.1-5 mg/ml, 0.1-2.5 mg/ml, 0.1-1 mg/ml, 0.2-2000 mg/ml, 0.2-200 mg/ml, 0.2-20 mg/ml, 0.2-2 mg/ml, 1-1000 mg/ml, 10-100 mg/ml, 10-50 mg/ml, 2-2000 mg/ml, 20-200 mg/ml, 20-100 mg/ml, e.g. 20-30 mg/ml or e.g. 0.2-0.7 mg/ml.

According to an alternative or an additional embodiment, the composition comprises THCA at a range of 5-100 mg/ml/gr of fresh cannabis, e.g. 20-30 mg/ml mg/ml/gr of fresh cannabis.

According to an alternative or an additional embodiment, the composition comprises cannabis derived active ingredients other than the THCA.

According to an alternative or an additional embodiment, the composition comprises at least one of D-Limonene, β-Caryophyllene, Humulene, malic acid, α-Farnesene, cannabinol (CBN), Δ9-tetrahydrocannabinol (THC), and/or cannabigerol (CBG).

According to an alternative or an additional embodiment, the composition comprises at least two, at least three, at least four, at least five, at least six, at least seven of D-Limonene, β-Caryophyllene, Humulene, malic acid, α-Farnesene, cannabinol (CBN), Δ9-tetrahydrocannabinol (THC), and/or cannabigerol (CBG).

According to an alternative or an additional embodiment, the composition comprises D-Limonene, β-Caryophyllene, Humulene, malic acid, α-Farnesene, cannabinol (CBN), Δ9-tetrahydrocannabinol (THC), and cannabigerol (CBG).

According to an alternative or an additional embodiment, the composition comprises THCA and any one, two, three, four, five, six or seven of D-Limonene, β-Caryophyllene, Humulene, malic acid, α-Farnesene, cannabinol (CBN), Δ9-tetrahydrocannabinol (THC), and/or cannabigerol (CBG).

According to an alternative or an additional embodiment, the composition comprises THCA, D-Limonene, β-Caryophyllene, Humulene, malic acid, α-Farnesene, cannabinol (CBN), Δ9-tetrahydrocannabinol (THC), and cannabigerol (CBG).

According to an alternative or an additional embodiment, the composition comprises components as listed in Table 6, herein below.

According to an alternative or an additional embodiment, the composition of some embodiments of the invention comprises at least one, two, three, four, five, six, seven, eight, nine, ten or more components as listed in Table 6.

According to an alternative or an additional embodiment, the compositions of some embodiments of the invention comprise THCA as well as at least one, two, three, four, five, six, seven, eight, nine, ten or more components as listed in Table 6.

According to an alternative or an additional embodiment, the collective amount of the components in the fraction or composition does not exceed about 30%, about 20%, about 10% or about 5%.

According to an alternative or an additional embodiment, the composition comprises cannabis derived active ingredients other than the THCA.

According to an alternative or an additional embodiment, the extracts and/or fractions obtained by the methods of some embodiments of the invention may supplemented with components not present in the extract/fractions or present in the extract/fractions (such as to increase the level of a specific component).

According to an alternative or an additional embodiment, the composition comprises CBD.

As used herein, the term "CBD" refers to cannabidiol. The term CBD as used herein encompasses native CBD (i.e. originating from the Cannabis plant), or synthetic analogs or derivatives thereof. Any CBD analog may be used in accordance with the present teachings as long as it comprises an anti-inflammatory activity (alone, or as part of the composition discussed herein).

Exemplary CBD analogs include, but are not limited to, (−)-DMH-CBD-11-oic acid, HU-308 (commercially available e.g. from Tocris Bioscience, 3088), O-1602 (commercially available e.g. from Tocris Bioscience 2797/10), DMH-CBD (commercially available e.g. from Tocris Bioscience, 1481) [as discussed in detail in Burstein S, Bioorg Med Chem. (2015) 23(7): 1377-85], Abn-CBD, HUF-101. CBDV, CBDM, CBND-C5, CBND-C3, 6-Hydroxy-CBD-triacetate or CBD-aldehyde-diacetate [as discussed in detail in An Overview on Medicinal Chemistry of Synthetic and Natural Derivatives of Cannabidiol, Frontiers in Pharmacology, June 2017|Volume 8|Article 422].

According to aspect of the invention, there is provided a composition comprising THCA and CBD, wherein the composition is devoid of cannabichromene (CBC).

According to an alternative or an additional embodiment, there is provided a composition comprising THCA and CBD, wherein the composition is devoid of at least one of cannabichromene (CBC), cannabigerolic acid (CBGA), cannabidiolic acid (CBDA), cannabigerol (CBG) and/or cannabinol (CBN).

According to an alternative or an additional embodiment, there is provided a composition comprising THCA and CBD, wherein the composition is devoid of cannabichromene (CBC), cannabigerolic acid (CBGA), cannabidiolic acid (CBDA), cannabigerol (CBG) and cannabinol (CBN).

According to an alternative or an additional embodiment, the composition comprises THCA, CBD and any one, two, three, four, five, six or seven of D-Limonene, β-Caryophyllene, Humulene, malic acid, α-Farnesene, cannabinol (CBN), Δ9-tetrahydrocannabinol (THC), and/or cannabigerol (CBG).

According to an alternative or an additional embodiment, the composition comprises THCA, CBD, D-Limonene, β-Caryophyllene, Humulene, malic acid, α-Farnesene, cannabinol (CBN), Δ9-tetrahydrocannabinol (THC), and cannabigerol (CBG).

According to an alternative or an additional embodiment, the compositions of some embodiments of the invention comprise THCA, CBD as well as at least one, two, three, four, five, six, seven, eight, nine, ten or more components as listed in Table 6.

According to an alternative or an additional embodiment, the different components (e.g. THCA and CBD) are discrete i.e. not comprised in the same fraction.

According to an alternative or an additional embodiment, the fractions are combined into a single composition.

According to an alternative or an additional embodiment, the fractions are comprised in different formulations/compositions.

According to an alternative or an additional embodiment, the composition comprising THCA and CBD (as active ingredients) may comprise a dose range of THCA as discussed above.

According to an alternative or an additional embodiment, the composition comprising THCA and CBD (as active ingredients) may comprise a dose range of CBD of 0.01-1000 mM, 0.01-100 mM, 0.01-10 mM, 0.01-1 mM, 0.1-1000 mM, 0.1-500 mM, 0.1-100 mM, 0.1-50 mM, 0.1-10 mM, 0.1-5 mM, 0.1-2.5 mM, 0.1-1 mM, 0.5-50 mM, 0.5-10 mM, 0.5-5 mM, 0.5-1 mM, e.g. 0.22-0.45 mM or 0.01-0.03.

Since the extracts of the present invention, active fractions derived therefrom, and compositions comprising same have anti-inflammatory activity, they may be used for treating diseases or disorders related thereto.

Thus, according to one aspect of the present invention, there is provided a method of treating an inflammatory disease in a subject in need thereof, the method comprising administering to the subject a therapeutically effective amount of the composition of some embodiments of the invention, thereby treating the inflammatory disease in the subject.

According to one aspect of the present invention, there is provided a therapeutically effective amount of the composition of some embodiments of the invention for use in treating an inflammatory disease in a subject in need thereof.

According to one aspect of the present invention, there is provided a method of treating an inflammatory disease in a subject in need thereof, the method comprising administering to the subject a therapeutically effective amount of a liquid chromatography fraction of a cannabis extract comprising at least about 75% tetrahydrocannabinolic acid (THCA), wherein the fraction comprises cannabis derived active ingredients other than the THCA, thereby treating the inflammatory disease in the subject.

According to one aspect of the present invention, there is provided a therapeutically effective amount of a liquid chromatography fraction of a cannabis extract comprising at least about 75% tetrahydrocannabinolic acid (THCA), wherein the fraction comprises cannabis derived active ingredients other than the THCA, for use in treating an inflammatory disease in a subject in need thereof.

According to one aspect of the present invention, there is provided a method of treating an inflammatory disease in a subject in need thereof, the method comprising administering to the subject a composition of matter comprising a therapeutically effective amount of liquid chromatography pooled fractions of cannabis extract comprising active ingredients detectable by a detector operated at 220 nm, wherein the active ingredients comprise THCA, thereby treating the inflammatory disease in the subject.

According to one aspect of the present invention, there is provided a therapeutically effective amount of liquid chromatography pooled fractions of cannabis extract comprising active ingredients detectable by a detector operated at 220 nm, wherein the active ingredients comprise THCA, for use in treating an inflammatory disease in a subject in need thereof.

As the present inventors have illustrated that THCA has anti-inflammatory activity on its own, it is proposed that THCA can be used as is for the treatment of inflammatory disease in a subject in need thereof.

Thus, according to another aspect of the present invention, there is provided a method of treating an inflammatory disease in a subject in need thereof, the method comprising administering to the subject a therapeutically effective amount of a composition comprising tetrahydrocannabinolic acid (THCA), wherein the THCA constitutes at least about 30% of the active ingredients in the composition, thereby treating the inflammatory disease in the subject.

According to another aspect of the present invention, there is provided a therapeutically effective amount tetrahydrocannabinolic acid (THCA), for use in treating an inflammatory disease in a subject in need thereof, wherein the THCA constitutes at least about 30% of the active ingredients in the composition.

According to an alternative or an additional embodiment, the THCA constitutes at least about 30%, about 40%, about 50%, about 60%, about 70%, about 75%, about 80%, about 85%, about 90%, about 95%, about 99%, or about 100% of the active ingredients in the composition.

As used herein, the term "subject" or "subject in need thereof" refers to a mammalian e.g., human subject, at any age or gender, who has an inflammatory disease.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

A number of diseases and conditions, which involve an inflammatory response, can be treated using the methodology described hereinabove. Examples of such diseases and conditions are summarized infra.

Inflammatory diseases—Include, but are not limited to, chronic inflammatory diseases and acute inflammatory diseases.

Inflammatory Diseases Associated with Hypersensitivity

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like β-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci USA 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12):2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited nto, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E.

et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. Diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann NY Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Graft Rejection Diseases

Examples of diseases associated with transplantation of a graft include, but are not limited to, graft rejection, chronic graft rejection, subacute graft rejection, hyperacute graft rejection, acute graft rejection and graft versus host disease.

Allergic Diseases

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

According to a specific embodiment, the inflammatory disease is an inflammatory bowel disease (IBDs). According to a particular embodiment, the IBD is Crohn's disease (CD) or ulcerative colitis (UC).

According to some embodiment, the method further comprises administering to the subject a therapeutically effective amount of cannabidiol (CBD).

According to some embodiment, the fraction, fractions, THCA or composition for use further comprises the use of a therapeutically effective amount of cannabidiol (CBD).

According to one embodiment, CBD may be administered prior to, concomitantly with, or following administration of the composition of some embodiments of the invention.

According to some embodiment, the method further comprises administering to the subject an agonist of CB1 receptor, CB2 receptor and/or GPR55.

According to some embodiment, the fraction, fractions, THCA or composition for use further comprises the use of an agonist of CB1 receptor, CB2 receptor and/or GPR55.

Any known agonist of CB1 receptor, CB2 receptor and/or GPR55 may be used in accordance with the present teachings. According to one embodiment, an agonist of CB1 receptor comprises, for example, nabilone, WIN 55,212-2, HU210, and anandamide. According to one embodiment, an agonist of CB2 receptor comprises, for example, AM1241, GW405833, JWH133 and WIN 55,212-2. According to one embodiment, an agonist of GPR55 receptor comprises, for example, 2-arachidonoylglycerolphosphoinositol.

According to one embodiment, the agonist of CB1 receptor, CB2 receptor and/or GPR55 may be administered prior to, concomitantly with, or following administration of the composition of some embodiments of the invention.

Each of the compositions described hereinabove can be administered to the individual per se or as part of a pharmaceutical composition which also includes physiologically acceptable carriers or excipients. The purpose of a pharmaceutical composition is to facilitate administration of the active ingredient to an organism.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the cannabis derived active ingredients accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

The term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For transdermal administration, the composition can be formulated in a form of a gel, a cream, an ointment, a paste, a lotion, a milk, a suspension, an aerosol, a spray, a foam, a serum, a swab, a pledget, a pad or a patch. Formulations for transdermal delivery can typically include carriers such as water, liquid alcohols, liquid glycols, liquid polyalkylene glycols, liquid esters, liquid amides, liquid protein hydrolysates, liquid alkylated protein hydrolysates, liquid lanolin, lanolin derivatives, glycerin, mineral oil, silicone, petroleum jelly, lanolin, fatty acids, vegetable oils, parabens, waxes, and like materials commonly employed in topical compositions. Various additives, known to those skilled in the art, may be included in the transdermal formulations of the invention. For example, solvents may be used to solubilize certain active ingredients substances. Other optional additives include skin permeation enhancers, opacifiers, antioxidants, gelling agents, thickening agents, stabilizers, and the like.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran.

Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (cannabis derived active ingredients) effective to prevent, alleviate or ameliorate symptoms of a disorder (e.g., IBD) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Animal models for inflammation are described for example in Webb D R, *Biochem Pharmacol.* (2014) 87(1): 121-30.

According to one embodiment, a therapeutically effective amount of a composition comprising liquid chromatography pooled fractions of cannabis extract comprising active ingredients detectable by a detector operated at 220 nm, wherein the active ingredients comprise THCA, is in the range of 0.1-1000 mg/day/kg, 0.1-100 mg/day/kg, 0.1-50 mg/day/kg, 0.1-10 mg/day/kg, 0.1-5 mg/day/kg, 0.1-2.5 mg/day/kg, 0.1-1 mg/day/kg, 0.2-1.5 mg/day/kg, e.g. 0.2-0.7 mg/day/kg, e.g. 0.7 mg/day/kg.

According to one embodiment, a therapeutically effective amount of a composition comprising a therapeutically effective amount of a liquid chromatography fraction of a cannabis extract comprising at least about 30% THCA (e.g. 60-100% THCA e.g. 75% THCA), wherein the fraction comprises cannabis derived active ingredients other than the THCA, is in the range of 0.1-1000 mg/day/kg, 0.1-500 mg/day/kg, 0.1-100 mg/day/kg, 0.1-50 mg/day/kg, 0.1-10 mg/day/kg, 0.1-5 mg/day/kg, 0.1-2.5 mg/day/kg, 0.1-1 mg/day/kg, 0.2-1.5 mg/day/kg, e.g. 0.2-0.7 mg/day/kg, e.g. 0.7 mg/day/kg.

As mentioned, a synergistic anti-inflammatory affect has been observed when the above described compositions where administered along with CBD.

Accordingly, when CBD is administered in conjunction with a composition comprising liquid chromatography pooled fractions of cannabis extract comprising active ingredients detectable by a detector operated at 220 nm, wherein the active ingredients comprise THCA, a therapeutically effective amount is based on the relation of the CBD to the composition.

Similarly, when CBD is administered in conjunction with a composition comprising a therapeutically effective amount of a liquid chromatography fraction of a cannabis extract comprising at least about 30% THCA (e.g. 60-100% THCA e.g. 75% THCA), wherein the fraction comprises cannabis derived active ingredients other than the THCA, a therapeutically effective amount is based on the relation of the CBD to the composition.

According to one embodiment, CBD can be administered at a dose range of 0.1-1000 mM/day/kg, 0.1-500 mM/day/kg, 0.1-100 mM/day/kg, 0.1-50 mM/day/kg, 0.1-10 mM/day/kg, 0.1-5 mM/day/kg, 0.1-2.5 mM/day/kg, 0.1-1 mM/day/kg, 0.5-50 mM/day/kg, 0.5-10 mM/day/kg, 0.5-5 mM/day/kg, 0.5-1 mM/day/kg, e.g. 0.22-0.45 mM/day/kg.

Thus, according to one embodiment, when the composition is administered at a dose of 0.7 mg/day/kg (wherein the active ingredients comprise THCA), CBD is administered at a dose of 0.45 mM/day/kg, i.e. at a relation of 1.5:1 (composition:CBD).

According to one embodiment when the composition is administered at a dose of 0.7 mg/day/kg (wherein the active ingredients comprise THCA), CBD is administered at a dose of 0.22 mM/day/kg, i.e. at a relation of 3:1 (composition:CBD). Such a dosing can be adjusted as long as the relation of composition:CBD is maintained.

According to one embodiment when CBD is administered at a dose of 0.4 mM/day/kg, the composition (wherein the active ingredients comprise THCA) is administered at a dose of 0.4 mg/day/kg, i.e. at a relation of 1:1 (CBD:composition).

According to one embodiment when CBD is administered at a dose of 0.4 mM/day/kg, the composition (wherein the active ingredients comprise THCA) is administered at a dose of 0.3 mg/day/kg, i.e. at a relation of 1.33:1 (CBD:composition).

According to one embodiment when CBD is administered at a dose of 0.4 mM/day/kg, the composition (wherein the active ingredients comprise THCA) is administered at a dose of 0.2 mg/day/kg, i.e. at a relation of 2:1 (CBD:composition).

Such a dosing can be adjusted as long as the relation of composition:CBD or CBD:composition is maintained as described above, a person of skill in the art can make the proper adjustments based on the subject being treated and the level of the components (e.g. THCA) in the composition.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide cannabis derived active ingredients (the intestinal tissue) levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

According to another embodiment, in order to enhance treatment of the inflammatory disease, the present invention further envisions administering to the subject an additional therapy which may benefit treatment. One of skill in the art is capable of making such a determination.

Thus, for example, the anti-inflammatory therapy may include, without being limited to, NSAIDs (Non-Steroidal Anti-inflammatory Drugs), corticosteroids (such as prednisone) and anti-histamines.

Additional anti-inflammatory agents which may be used according to the present teachings include, but are not limited to, Alclofenac; Alclometasone Dipropionate; Algestone Acetonide; Alpha Amylase; Amcinafal; Amcinafide; Amfenac Sodium; Amiprilose Hydrochloride; Anakinra;

Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Momiflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

Any of the above described agents may be administered individually or in combination.

The cannabis extract of the present invention can be administered to a subject (e.g., a human) in need thereof in a variety of other forms including a nutraceutical composition.

As used herein, a "nutraceutical composition" refers to any substance that may be considered a food or part of a food and provides medical or health benefits, including the prevention and treatment of disease. In some embodiments, a nutraceutical composition is intended to supplement the diet and contains at least one or more of the following ingredients: a vitamin; a mineral; an herb; a botanical; a fruit; a vegetable; an amino acid; or a concentrate, metabolite, constituent, or extract of any of the previously mentioned ingredients; and combinations thereof.

In some embodiments, a nutraceutical composition of the present invention can be administered as a "dietary supplement," as defined by the U.S. Food and Drug Administration, which is a product taken by mouth that contains a "dietary ingredient" such as, but not limited to, a vitamin, a mineral, an herb or other botanical, an amino acid, and substances such as an enzyme, an organ tissue, a glandular, a metabolite, or an extract or concentrate thereof.

Non-limiting forms of nutraceutical compositions of the present invention include: a tablet, a capsule, a pill, a softgel, a gelcap, a liquid, a powder, a solution, a tincture, a suspension, a syrup, or other forms known to persons of skill in the art. A nutraceutical composition can also be in the form of a food, such as, but not limited to, a food bar, a beverage, a food gel, a food additive/supplement, a powder, a syrup, and combinations thereof.

According to another aspect of the invention, there is provided a method of determining an anti-inflammatory activity of the composition of some embodiments of the invention, the method comprising ex-vivo contacting an inflamed tissue of a subject with the composition, wherein an increased anti-inflammatory response of the inflamed tissue above a predetermined threshold is indicative of the anti-inflammatory activity of the composition.

According to one embodiment, the inflamed tissue is a gastrointestinal tissue biopsy. Exemplary tissues include oesophagus, gallbladder, liver, pancreas, stomach, small intestine, bowel (large intestine or colon and rectum), and anus.

According to one embodiment, the inflamed tissue is obtained from a subject at an active stage of an inflammatory disease. Exemplary inflammatory diseases include, but are not limited to, IBD, UC and Crohn's disease.

According to one embodiment, the anti-inflammatory activity of the composition comprises an upregulation in secretion of an anti-inflammatory factor (e.g. cytokine such as, but not limited to, IL-4, IL-10, IL-13, IFN-alpha and TGF-beta) and/or reduction in secretion of a pro-inflammatory factor (e.g. cytokine such as, but not limited to, IL-6, IL-8, IL-1$\beta$, TNF-$\alpha$, INF-$\gamma$, IL-12, IL-18 and GM-CSF).

According to one embodiment, the anti-inflammatory activity of the composition comprises reduction in expression of a gene associated with the inflammation. According to one embodiment, exemplary genes include, but are not limited to, MMP9 and COX2.

According to one embodiment, a predetermined threshold can be established by determining an expression level (e.g. of a gene) or secretion of a factor (e.g. cytokine) by a healthy tissue (e.g. of a healthy donor subject, of the subject before disease onset or during disease remission, or from tissue cultures available commercially).

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Procedures

Extraction of Cannabis Inflorescence

Fresh flowers of *C. sativa* strain AD were harvested from plants. They were either taken immediately for extraction and frozen at −80° C., or baked for 3 hours at 150° C. prior to extraction. Fresh and baked Cannabis flowers (2 g) were pulverized with liquid nitrogen. Absolute ethanol was added to each tube containing the powder at a sample-to-absolute ethanol ratio of 1:4 (w/v). The tubes were mixed thoroughly on a shaker for 30 minutes and then the extract was filtered through a filter paper. The filtrate was transferred to new tubes. The solvent was evaporated with a vacuum evaporator. The dried extract was resuspended in 1 mL of absolute methanol and filtered through a 0.45-μm syringe filter. The filtered liquid was collected for the treatments, the resuspended extract was diluted for cell cultures and biopsies in enzyme-linked immunosorbent assay (ELISA) experiments. Sample dry weight was determined by crushing 1 g of plant material with known fresh weight and incubating overnight at 60° C., then weighing again for dry weight calculation.

Chemical Characterization

Standard Preparation

The cannabinoid standards cannabigerol (CBG), cannabidiol (CBD), cannabidiolic acid (CBDA), cannabinol (CBN), cannabigerolic acid (CBGA), tetrahydrocannabinol (THC), cannabichromene (CBC) and tetrahydrocannabinolic acid (THCA) were diluted to 10 ppm concentration with methanol and then subjected to HPLC separation. For quantification of THC and THCA, the standards were dissolved in methanol at different concentrations from 5 ppm to 40 ppm.

Sample Preparation

For HPLC, the dry extract (the ethanol crude) was resuspended in 1 mL methanol and filtered through a 0.45-μm syringe filter (Merck, Darmstadt, Germany). The filtered extract (the filtrate) was diluted 10 times with methanol and then separated by HPLC. For profile, the filtrate was diluted 50 times with methanol.

HPLC Separation

Sample separation was carried out in an UltiMate 3000 HPLC system coupled with WPS-3000(T) Autosampler, HPG-3400 pump, and DAD-300 detector. The separation was performed on a Purospher RP-18 end capped column (250 mm×4.6 mm I.D.; Merck KGaA, Darmstadt, Germany) with a guard column (4 mm×4 mm I.D.). Solvent gradients were formed by isocratic proportion with 15% solvent A (0.1% acetic acid in water) and 85% solvent B (methanol) at a flow rate of 1.5 mL/min for 35 minutes. The compound peaks were detected at 220, 240 and 280 nm. The 220-nm peaks were taken for further processing. The extracts were fractionated into nine fractions according to the obtained chromatogram.

Gas Chromatograph (GC) with Mass Selective Detector (MSD) (GC/MS) Analysis

GC/MS analyses were carried out using a HP7890 gas chromatograph coupled to a HP6973 mass spectrometer with electron multiplier potential 2 KV, filament current 0.35 mA, electron energy 70 eV, and the spectra were recorded over the range m/z 40 to 400. An Agilent 7683 autosampler was used for sample introduction. Helium was used as a carrier gas at a constant flow of 1.1 ml s-1. One µl of each sample was injected to the GC/MS using a 1:10 split ratio injection mode. An isothermal hold at 50° C. was kept for 2 minutes, followed by a heating gradient of 6° C. min-1 to 300° C., with the final temperature held for 4 minutes. A 30 m, 0.25 mm ID 5% cross-linked phenylmethyl siloxane capillary column (HP-5MS) with a 0.25 µm film thickness was used for separation and the injection port temperature was 220° C. The MS interface temperature was 280° C. Peak assignments were performed with a spectral library (NIST 14.0) and compared with published and MS data obtained from the injection of standards purchased from LGC standards. Prior to GC/MS analysis, 200 µL of N,O-bis(trimethylsilyl)trifluoroacetamide (BSTFA, purchased from Sigma-Aldrich, Israel) containing 1% of trimethylchlorosilane (TMCS) was added to each completely dried extract and heated to 70° C. for 20 minutes. One µL of each sample was injected to the GC/MS (described above) using a 1:10 split ratio injection mode.

Mass Spectrometry (MS) Analysis

Analysis of the fractions was carried out using ESI (Q-TOF) 6545 (high resolution) (Agilent). The MS conditions were as follows: ESI positive mode, m/z 50-1500, gas temperature 350° C., injection volume 5 µL, solvent composition 0.1% formic acid in water (46%), acetonitrile (50%) and water (4%) (v/v).

Nuclear Magnetic Resonance (NMR) Analysis $^1$H and $^{13}$C spectra were recorded in a Bruker Avance-400 instrument (400.1 and 100.6 MHz, respectively) in $CDCl_3$ as the solvent, containing Tetramethylsilane (TMS) as an internal reference, at 300K. In addition, three 2D experiments were performed: COSY ($^1$H-$^1$H correlation), HMQC (one-bond $^1$H-$^{13}$C correlation) and HMBC (long-range $^1$H-$^{13}$C correlation).

Cell Cultures and Determination of Anti-Inflammatory Activity in HCT116, HT29 Cells and CaCO2 Cells HCT116 (ATCC CCL-247), HT29 (ATCC HTB-38) and CaCO2 (ATCC HTB-37) colon cells were grown at 37° C. in a humidified 5% $CO_2$-95% air atmosphere. Cells were maintained in McCoy's 5a Modified Medium (HCT116 and HT29) and Dulbecco's modified Eagle's medium (DMEM) supplemented with 10% fetal bovine serum (CaCO2).

Cells were seeded, in triplicate, into a 24-well plate at a concentration of 50,000 cells per well in 500 µL, of growing media, and then incubated for 24 hours at 37° C. in a humidified 5% $CO_2$-95% air atmosphere. When cell excitation was performed with TNF-α, cultures in each well were treated with 50-300 ng/mL recombinant human TNF-α (PeproTech, Rocky Hill, N.J., USA) and 50 µL plant extract, as described above (dilution index 57 or 280). The supernatant was taken and the level of IL-8 [12] was measured 4-16 hours post-treatment using the commercial Human CXCL8/IL-8 DuoSet ELISA kit (R&D Systems, Minneapolis, Minn., USA). As a positive control dexamethasone (Sigma-Aldrich, St. Louis, Mo., USA) at 20, 200 and 400 µM final concentration was used.

The involvement of the receptors (CB1, CB2 and GPR55) was examined by treating the cells with 20 µM of the CB1 receptor antagonist/inverse agonist Rimonabant (Abcam, Cambridge, Mass., USA), CB2 receptor antagonist/inverse agonist SR144528 (Abcam) and GPR55 antagonist/inverse agonist CID16020046 (Sigma-Aldrich, Buchs, Switzerland). The whole extract from fresh flowers (C2F) or the active fraction (F7) was applied to cells along with TNF-α 1 hour after the antagonist treatment. Cell treatment with purified compounds was performed with CBD (Restek, Pa., USA) at different concentrations (as indicated in each experiment), THCA (THCA-A; Restek) at a final concentration of 0.2 mM and THC (Restek) at a final concentration of as indicated in each experiment mM to confirm the activity of each cannabinoid.

Resazurin (R&D Systems) was used to check the cytotoxic effect of extracts. For this, 10% Resazurin was added to each well of the treatments with different dilution. Then the plate was incubated for 2-4 hours at 37° C. in a humidified 5% $CO_2$-95% air atmosphere. Supernatant (100 µL from each well) was transferred to a 96-well plate and the relative fluorescence at the excitation/emission of 544/590 nm was measured. The number of live cells was calculated with a linear standard concentrate curve built by seeding different concentrations of cells in 24-well plates treated with Resazurin. Values were calculated as percentage of live cells relative to the non-treated (cells without TNF-α and treatments) control after reducing auto-fluorescence of Alamar Blue without cells.

For dose response assays, data points were connected by non-linear regression lines of the sigmoidal dose-response relation. GraphPad Prism (version 6 for windows, GraphPad software Inc. San Diego, USA) was employed to produce dose-response curves and $IC_{50}$ doses were calculated using nonlinear regression analysis.

Culture of Biopsies

Three biopsies from both healthy and inflamed intestine of IBD (inflammatory bowel disease) patients were obtained from 29 patients with either Crohn's disease (CD) or ulcerative colitis (UC) scheduled for colonoscopy as deemed necessary by their physician, Helsinki approval no. 0094-16 was obtained. After obtaining informed consent, biopsies from inflamed and normal tissue were taken and placed in tissue culture media. Upon receiving the biopsies, PBS was replaced with 75 µL dispase (StemCell Technologies, Cambridge, UK) and 150 µL collagenase 1A (StemCell Technologies) solution. Tubes were then incubated at 37° C. for 1 hour. After incubation, the tubes containing the biopsies were centrifuged at 8000 rpm (11,885×g) for 1 minute. Then the supernatant was removed and tissues were washed three times with Hank's balanced salt solution. After each wash, tubes were centrifuged as described above. Then the tissues were placed on a small petri dish and cut into 2-3 pieces with a clean scalpel. The pieces were then placed on Millicel hydrophilic PTFE tissue-culture inserts (Millipore, 30 mm, 0.4 µm). The inserts were placed in 6-well plastic tissue-culture dishes (Costar 3506) along with 1.5 mL of tissue-culture medium (Dulbecco's modified Eagle's medium supplemented with 10% v/v heat-inactivated fetal calf serum, 100 U/mL penicillin, 100 µg/mL streptomycin, 50 µg/mL leupeptin, 1 mM PMSF, and 50 µg/mL soybean trypsin inhibitor). When dexamethasone was included in the media, its concentration was 200 µg/mL. This was followed by treating the tissues with extracts as mentioned above, or leaving them untreated (control). When TNF-α was added to induce interleukins (IL) expression, the concentration was 50 ng/mL. Cultures were then incubated at 37° C. in a humidified 5% $CO_2$-95% air atmosphere. To evaluate TNF-α expression, supernatants were taken after 1 hour of incubation. For other ILs, supernatants were taken after overnight incubation unless otherwise stated. The supernatants from the biopsies were used for determination of IL-8 cytokine profile by measuring its levels with a commercial ELISA kit. Levels of cytokines from inflamed, cannabis-treated and non-treated tissue were compared.

Quantitative Real-time (qRT) PCR

Cells were seeded into a 6-well plate at a concentration of 1,500,000 cell/mL per well. After 24 hours incubation at 37° C. in a humidified 5% $CO_2$-95% air atmosphere, cells were treated with TNF-α (final concentration of 1 ng/mL) and incubated overnight under the same conditions. Non-treated cells or cells treated only with TNF-α served as negative and positive controls, respectively. Cells were then reincubated for 5 hours with C2F (0.2 mg crude dry extract/mL) or F7 (0.08 mg/mL) at 37° C. in a humidified 5% $CO_2$-95% air atmosphere. The next day, cells were harvested and total RNA was extracted using TRI reagent (Sigma-Aldrich) according to the manufacturer's protocol. For biopsies, all treatments were added overnight, after which the biopsies were stored at −20° C. in RNA Save solution (Biological Industries, Beit Haemek, Israel). RNA was extracted from frozen biopsies. Tissue samples were homogenized with an appropriate homogenizer in TRI reagent, as done for the cells. RNA (50 ng for biopsies: four UC patients and one CD patient) or 2.5 μg (for cells) was reverse-transcribed in a total volume of 20 μL using Maxima reverse transcriptase (Thermo Scientific, Boston, Mass., USA) according to the manufacturer's protocol. All primers were designed using Primer3Plus software. PCR was performed in triplicate using a Rotor-Gene 6000 instrument (QIAGEN, Zurich, Switzerland) and Maxima SyGreen Mix (Thermo Scientific) according to the manufacturer's protocol. The expression of each target gene was normalized to the expression of GAPDH mRNA in the 2-ΔΔCt and is presented as the ratio of the target gene to GAPDH mRNA, expressed as 2-ΔCt, where Ct is the threshold cycle and ΔCt=Ct Target–Ct GAPDH. Experiments were repeated three times. The primers were: for COX2 (forward, SEQ ID NO: 1) 5'-ATTGACCAGAGCAGGCAGAT-3' and (reverse, SEQ ID NO: 2) 5'-CAGGATACAGCTCCACAGCA-3', and for MMP9 (forward, SEQ ID NO: 3) 5'-TTGACAGCGACAAG-AAGTGG-3' and (reverse, SEQ ID NO: 4) 5'-TCACGTCG-TCCTTATGCAAG-3'.

Analysis of Combined Drug Effects

In order to examine if there is a synergy between CBD and F7, ELISA assay was used to measure the anti-inflammatory activity of the fractions on HCT116 cells. Cells were seeded into a 24-well plates at 50,000 cells per well in triplicate in normal growing media. After 24 hours of incubation at 37° C. in a humidified 5% CO2-95% air atmosphere, cells were treated with different concentration of F7 (5 μg/mL to 80 μg/mL) with and without CBD (30 μM) along with 300 ng/mL of TNF-α or with different concentration of CBD (5 μM to 120 μM) with and without F7 (30 μg/mL) along with 300 ng/mL of TNF-α for 4 hours. Following, the supernatant was taken and the levels of IL-8 were measured using the commercial Human CXCL8/IL-8 DuoSet ELISA kit (R&D Systems, Minneapolis, Minn., USA). Resazurin (R&D Systems) was used to check the cytotoxic effect of extracts.

Drug synergy was determined by Bliss independence drug interaction model which is defined by the following equation:

$$Exy=Ex+Ey-(ExEy)$$

Where (Exy) is the additive effect of the drug x and y as predicted by their individual effects (Ex and Ey). For calculation purpose, in this paper, the drug's anti-cancer effect was defined as complementary to the obtained results (1−Exy). The observed combined percentage viability is then compared to the calculated value. If the observed value of Exy is greater than the calculated Exy value, the combination treatment is considered as worse than expected, which means antagonism effect. If the observed value is less than the calculated one, then the combination treatment is considered as better than expected, thus showing synergism effect. If both values are equal, the combination treatment is considered as the same for the addition of the two drugs, which means additive effect (independent).

Statistical Analyses

Results are presented as mean±SE of replicate analyses and are either representative of or include at least two independent experiments. Means of replicates were subjected to statistical analysis by Tukey-Kramer test ($P≤0.05$) using the JMP statistical package and considered significant when $P≤0.05$.

Example 1

*C. sativa* Extracts From Fresh Flowers are Highly Active in Reducing Inflammation in Colon Cell Lines Anti-inflammation activity was determined for absolute ethanol extracts of fresh (C2F) and baked (C2B) flowers of *C. sativa* (Cs-AD var.). The activity was determined as the level of reduction of IL-8 in HCT116 colon cancer cell cultures pretreated with TNF-α to induce IL-8 expression and then treated with C2F or C2B (FIGS. 1B and 1E). Notably, IL-8 was used in several other studies, in HCT116 as well as other cell models and in IBD patients as an indicator for the level of IBD-related inflammation [Ihenetu K. et al., Eur J Pharmacol. (2003) 458:207-215; Banks C et al., J Pathol. (2003) 199:28-35]. At different concentrations of C2F and C2B (114-207 μg/mL), both extracts significantly reduced IL-8 levels when compared to TNF-α. Under these conditions, dexamethasone (at concentrations of 200 and 400 μM) was inactive in reducing IL-8 level (FIGS. 1B and 1E). As both ethanol extracts of *C. sativa* significantly reduced IL-8 levels they were implicated to have anti-inflammatory activity. Moreover, C2F extracts were significantly more active than those of C2B in reducing IL-8 levels (FIG. 1B).

To determine that the reduction in IL-8 is due to anti-inflammatory rather than cytotoxic effect, cell viability was examined for the C2F and C2B treatments at different concentrations. At most examined concentrations C2B had significant cytotoxic activity, whereas C2F did not (FIGS. 1A and 1F). These results suggest that although the reduction in IL-8 level following treatment with C2B may be derived from cell death, that reduction following treatment with C2F is solely based on anti-inflammatory activity.

Similar anti-inflammatory activity results for C2F and C2B were obtained in HT29 and CaCO2 cells, with C2F being significantly more active than C2B, and both being significantly more active than dexamethasone (FIGS. 1C-D and FIGS. 1G-J). Of note, slightly increased cytotoxicity (at higher concentrations) was determined for C2F in the CaCO2 cell line (FIGS. 1I-J).

Taken together, the results demonstrated strong activity of C. sativa extracts in conferring a reduction in IL-8, with C2F being more potent than C2B. Similar concentration values were found for $IC_{50}$ of C2F and C2B (0.0839 mg/mL and 0.0841 mg/mL for C2F and C2B, respectively; FIGS. 1C-D). Thus, these results demonstrated the strong, dose-dependent, anti-inflammation activity of C. sativa C2F, mostly absent in C2B.

Example 2

Chemical Composition of C. sativa Extracts From Fresh and Baked Flowers

HPLC chromatogram and main active compounds were determined for the anti-inflammation active extract, C2F, and for the less active extract, C2B (FIGS. 2A-B and Table 1).

TABLE 1

HPLC peak area and % of area for Cannabis fresh and baked flowers

| RT | C2F | | C2B | | Known compound |
|---|---|---|---|---|---|
| (Minutes) | Area of peak (mAU) | Area (%) | Area of peak (mAU) | Area (%) | |
| 2.604 | 7279491 | 0.61 | 4834101 | 0.63 | |
| 4.015 | 15943959 | 1.33 | 19329498 | 2.52 | |
| 5.947 | 5640210 | 0.47 | 9625348 | 1.26 | CBG |
| 6.466 | 3614080 | 0.30 | 84359176 | 11.00 | CBD |
| 7.996 | 14896186 | 1.24 | 6041859 | 0.79 | CBDA |
| 10.931 | 115095840 | 9.61 | 68550632 | 8.94 | CBN |
| 11.339 | 3592090 | 0.30 | 32233628 | 4.20 | CBGA |
| 13.146 | 25512280 | 2.13 | 518303552 | 67.59 | THC |
| 17.575 | 0 | 0.00 | 22981120 | 3.00 | CBC |
| 29.373 | 1006329152 | 84.01 | 544761 | 0.07 | THCA |
| | 1197903288 | 100.00 | 766803675 | 100.00 | |

Eight major cannabinoids were identified in the fresh and baked crude extracts at 220 nm. These peaks were identified as CBG, CBD, CBDA, CBN, CBGA, THC, CBC and THCA, with retention times of 5.9, 6.4, 7.9, 10.9, 11.3, 13.1, 17.5 and 29.3 minutes, respectively, relative to the HPLC profile of cannabinoid standards (not shown). The levels of CBD, CBGA and THC were 36, 14 and 32 times higher in the C2B versus C2F extract. CBC was not identified in C2F but appeared in C2B. The levels of THCA and CBDA in C2B were reduced 1200 and 1.5 times, respectively, compared to those in C2F (FIGS. 2A-B and Table 1), due to decarboxylation of CBDA and THCA during heating (e.g., [22]).

Example 3

Identification of an Active Fraction of the Fresh Flower Extract of C. sativa and the Effect of Combinations with Whole Extract C2F (at a concentration of 163 μg/mL) was fractionated (FIG. 3A) by HPLC. Fractions were collected and high concentrations (0.9 mg/ml) were examined for anti-inflammatory activity, determined as the level of IL-8 in HCT116 cells. One fraction, F7, significantly reduced the level of IL-8 per HCT116 cell to that of the whole extract treatment (C2F and F1-F9 pooled; FIGS. 3B and 3E). No significant reduction in IL-8 levels was observed for any of the other fractions (FIGS. 3B-C and 3E). None of the fractions reduced cell viability, whereas treatment with some showed even increased cell proliferation (e.g., F3, F9; FIG. 3F). Similar results of anti-inflammatory activity were obtained for F7 in HT29 and CaCO2 cells (FIGS. 1G-J).

Subsequently, C2F and F7 activities were compared on HCT116 cells by dilution of extracts and examination of anti-inflammatory and cytotoxic activities of C2F, F7, F1-F9 pool-without F7 and combined treatment of all fractions, including F7 (FIGS. 3B-3C and 3G-3H). As expected, F7 and C2F had similar anti-inflammatory activity, whereas F1-F9—excluding F7 treatment was inactive (FIGS. 3C and 3E). However, once F7 was added to F1-F9—excluding F7 treatment, anti-inflammatory activity was retained (FIGS. 3C and 3G). As for the cytotoxic activity, a marked induction of cytotoxicity was found for combined treatment of F1-F9—excluding F7 and addition of F7 at concentrations of 190 and 190 μg/mL, respectively, and even more profoundly, at concentrations of 163 and 190 μg/mL, for F1F9—excluding F7 and F7, respectively (FIG. 3H). These results suggest that F7 denotes anti-inflammatory activity in colon cell lines, whereas certain combinations of treatment with all fractions of the extract lead to a significant increase in the cytotoxic activity.

Example 4

CBD Reduces Inflammation Only at Lower Doses Yet its Cytotoxic Activity is Dose Dependent The fraction containing CBG, CBD and CBDA (F2) did not show any anti-inflammatory activity in HCT116 cells in terms of IL-8 reduction (FIGS. 3A-B). This is in contrast to several publications that have suggested that CBD is the main anti-inflammatory compound for IBD (reviewed by [23]). To further examine CBD activity, the anti-inflammatory and cytotoxic activity of pure CBD (purity was verified by HPLC, not shown) in HCT116, HT29, and CaCO2 cells. Treatment with purified CBD at different concentrations (16-252 μg/mL) leads to a reduction in IL-8 levels at lower concentrations of CBD (FIG. 3I). Yet, no anti-inflammatory activity for CBD was determined for the higher CBD concentrations in HCT116 cells (FIGS. 3D and 3I). CBD was active in reduction of IL-8 levels in CaCO2 and HT29 cells (FIG. 3I). However, treatments with CBD lead to a dose-dependent cell death in HCT116 and in CaCO2 cells, and to a lesser extent in HT29 cells (FIGS. 3J and FIG. 6).

Example 5

The Active Fraction of C. sativa Extract Contains Mainly THCA

The chemical composition of the active fraction (F7) was analyzed by HPLC and electrospray ionization mass spectrometry (ESI-MS). F7 was obtained as a broad peak in the HPLC chromatogram. To analyze its structure and verify its purity, it was analyzed at different dilutions, in comparison to a THCA standard. The results suggested that F7 is THCA (FIG. 4). ESI-MS results further confirmed that F7 contains THCA: $C_{22}H_{30}O_4$ (358.214); m/z (MH+) 359.222, (MNa+) 381.203. $^1H$ and $^{13}C$ spectra were taken to verify the exact structure and determine the purity of F7. The NMR results showed that F7 is indeed THCA, at a purity range of 80-95%. Of note, different samples of F7 (from different collections) were taken for analysis in two different methods, thus the difference between the purities. In GC/MS, the purity is the average of 5 different samples.

Example 6

THCA is Active Against Inflammation in HCT116 Cells

Since THCA was found to be the main compound in the active fraction of the *C. sativa* extract, the anti-inflammatory activity of the THCA (commercially available with purity of 99%) in HCT116 cells was determined. Treatments with THCA (purity verified by HPLC, not shown) significantly reduced IL-8 levels in HCT116 cells (FIG. 5). To further determine whether the activity in F7 derives only from THCA, its concentration in this fraction was determined to be 22.81 mg/mL, and F7 was diluted 280-fold, to correspond to 0.2 mM THCA. Under these conditions, the activities of F7 and THCA were similar (FIG. 5), further suggesting that the anti-inflammatory activity of F7 derives from that of THCA.

Together, the present results suggest that THCA, but not CBD, has anti-inflammatory activity in HCT116 cell lines. Moreover, the whole cannabis extract, C2F, or the pooled fractions, have higher activity than that of F7 or F1-F9 excluding F7, evident also for relatively low concentrations of the fractions. This suggests interactions between fractions such that the combination of F7 (THCA) and compound(s) present in *C. sativa* fresh extract is more potent than F7 (THCA) only, in reducing HCT116 cell inflammation.

Example 7

GPR55 Receptor Antagonist Significantly Reduces the Anti-inflammatory Activity of F7, Whereas CB2 Receptor Antagonist Significantly Increases HCT116 Cell Proliferation To determine whether C2F and F7 activity in HCT116 cells is conferred via the CB or GPR55 receptors, the effects of CB1, CB2 and GPR55 receptor antagonists (Rimonabant, SR144528 and CID16020046, respectively) on the anti-inflammatory were determined. CB1 and CB2 receptor antagonists did not significantly change the anti-inflammatory activity of F7 or F1-F9 (FIG. 7). However, addition of GPR55 antagonist led to a significant reduction in activity and to an increase in IL-8 levels in these treatments (FIG. 7). Addition of GPR55 antagonist did not change IL-8 level in control (FIG. 7).

Transcripts for CB1, CB2 and GPR55 were detected by qPCR in HCT116 cells. Expression of CB2 and GPR55 were significantly increased upon treatment with TNF-α in these cells (values are the steady-state level of gene expression in TNF-α-treated versus non-treated cells; Table 2).

TABLE 2

Relative gene expression in HCT-116 cells. CB1, CB2 and GPR55 gene expression was measured following overnight treatment of the cells with TNF-α.

| Gene | Mean relative expression | Std Err | Statistics |
| --- | --- | --- | --- |
| CB1 | 1.31 | 0.19 | AB |
| CB2 | 5.84 | 1.04 | A |
| GPR55 | 5.26 | 1.57 | B |

Of note, values of gene transcripts were determined as a ratio between target genes (CB1, CB2 and GPR55) versus a reference gene (GAPDH), using the 2-ΔΔCT method.

Example 8

Treatment with *C. sativa* Extracts C2F and F7 Leads to Reduction in IL-8 Levels in Patient Colon Tissue Since cell lines do not fully reflect the conditions in colon tissue, the inflammation-reducing activity of C2F and F7 was further verified in biopsies of colon tissue taken from IBD patients. Biopsies were maintained ex vivo and the levels of IL-8 and IL-6 were determined in non-treated versus C2F- and F7-treated tissue. Treatment with C2F reduced significantly both IL-8 and IL-6 levels compared to non-treated controls (n=29). These results confirmed the anti-inflammatory effect of C2F and F7 on colon tissues derived from IBD patients (FIG. 8).

Example 9

Treatment of HCT116 Cells and Biopsies With *C. sativa* Extracts C2F, F7 and the Purified Compounds, but not CBD, Leads to Reduction in MMP9 and COX2 Expression COX2 expression is induced in the large intestine of IBD patients (reviewed by [24]) and MMP9 is among the predominant proteinases expressed in the gut mucosa during active IBD, associated with disease severity [25]. The steady-state levels of MMP9 and COX2 expression were examined as markers for inflammation level in HCT116 cells and colon biopsies of IBD patients (four UC and one CD). Expression of both COX2 and MMP9 was significantly induced in HCT116 cells treated with TNF-α and significantly reduced by treatment with C2F and F7. F7 was more effective at reducing COX2 expression than C2F (FIG. 9A). In colon tissues, both COX2 and MMP9 expression was downregulated by C2F and F7 treatments (FIG. 9B). As with the cell lines, F7 was more effective than C2F at reducing COX2 expression (FIG. 9B).

Example 10

Synergistic Effects of Cannabinoids From *Cannabis sativa* Extracts in Anti-inflammatory Activity on Colorectal Cancer Cell Line (HT29)

To determine whether the interaction of F7 and CBD is synergistic, i.e., their combined activity is greater than the sum of their separate activities, the extent of their activity was examined at different concentrations. First, a dose response was carried out for F7, CBD and THC. FIG. 10 illustrates the dose response (in the anti-inflammatory activity) of F7 in HT29 cells after 4 hours of treatment. As evident from the results, treatment with F7 leads to a dose dependent reduction of IL-8 levels in HT29 cells. FIG. 11 illustrates the dose response (in the anti-inflammatory activity) of CBD in HT29 cells after 4 hours of treatment. As evident from the results, treatment with CBD leads to a dose dependent reduction of IL-8 levels in HT29 cells and there is a significant decrease in the IL-8 level even in low concentrations (below 20 µM). FIG. 12 illustrates the dose response (in the anti-inflammatory activity) of THC in HT29 cells after 4 hours of treatment. As evident from the results, treatment with THC leads to a dose dependent reduction of IL-8 levels in HT29 cells.

The $EC_{50}$ of F7, CBD and THC were calculated from the anti-inflammatory assay (50% of activity) (FIGS. 13A-C).

The $EC_{50}$ of F7, CBD and THC were determined to be 35.14, 30.35 and 102.2 µg/ml, respectively. These concentrations were further used in the next experiments of combinations of treatments.

The anti-inflammatory activity of F7 in different concentrations with and without CBD at its $EC_{50}$ dose (FIG. 14) and the anti-inflammatory activity of CBD at different concentrations with and without F7 at its $EC_{50}$ dose (FIG. 15) clearly shows that combination of the treatments enhanced the anti-inflammatory activity of either CBD or F7 alone.

To determine whether the interaction of F7 and CBD is synergistic, the extent of their activities was examined when combined at different concentrations. The partial effect of the drugs was calculated according to the Bliss independence model for each combination experiment. Five concentrations of each combination were examined. Synergistic interaction was found for the following combinations: F7 at a concentration of 30 µg/ml+CBD at concentrations of 20 and 10 µM and CBD at a concentration of 30 µM+F7 at concentrations of 30, 20 and 15 µg/ml (as shown in Tables 4 and 3, respectively, below). Marked in bold are concentrations which show synergism.

TABLE 3

Experimental and calculated values of ELISA experiment according to bliss model for combination of constant CBD and different concentrations of F7

| | CBD 30 uM | | | | |
|---|---|---|---|---|---|
| | F7 30 µg/mL | F7 20 µg/mL | F7 15 µg/mL | F7 10 µg/mL | F7 5 µg/mL |
| Calculated value | 32.36 | 51.23 | 58.49 | 56.72 | 60.69 |
| Experimental value | 27.41 | 41.15 | 50.28 | 63.71 | 64.60 |

TABLE 4

Experimental and calculated values of ELISA experiment according to bliss model for combination of constant F7 and different concentrations of CBD

| | F7 30 µg/mL | | | |
|---|---|---|---|---|
| | CBD 40 µM | CBD 20 µM | CBD 10 µM | CBD 5 µM |
| Calculated value | 25.93 | 47.82 | 54.19 | 57.42 |
| Experimental value | 29.23 | 21.42 | 40.96 | 67.35 |

Furthermore, the present inventors wanted to examine if there is synergism also between the standards (CBD and THCA). Five concentrations of THCA were examined (from 5 µg/mL to 30 µg/mL) along with CBD at a concentration of 30 Mm). Synergistic interaction was found for the following combinations: CBD (30 µM)+THCA in 30, 20, 15, 10, 5 µg/mL, as shown in Table 5, below.

TABLE 5

Experimental and calculated values of ELISA experiment according to bliss model

| | CBD 30 µM | | | | |
|---|---|---|---|---|---|
| | THCA 30 µg/mL | THCA 20 µg/mL | THCA 15 µg/mL | THCA 10 µg/mL | THCA 5 µg/mL |
| Calculated value | 59.51 | 86.12 | 78.47 | 82.26 | 81.33 |
| Experimental value | 15.64 | 56.97 | 37.23 | 54.77 | 64.39 |

Example 11

The Chemical Composition of Fraction 7

Further analysis of fraction F7 illustrates that F7 contains THCA, THC, CBD and CBN, additional acids (palmitic acid, Linolenic acid, malic acid, Arachidonic acid, stearic acid and myristic acid) and compounds as detailed in Table 6, below

TABLE 6

Composition for Fraction 7 (F7) as repeatedly collected from the analytical HPLC (summarized results from 5 repeats) and analyzed using GC/MS with NIST 14.0

| C2F_F7 Compounds | % | of 1 gr fresh flower mg/mL |
|---|---|---|
| D-Limonene | 0.097 | 0.036011 |
| Glycerol | 0.086 | 0.031928 |
| β-Caryophyllene | 0.103 | 0.038239 |
| Humulene | 0.03 | 0.011138 |
| malic acid | 0.035 | 0.012994 |
| α-Farnesene | 0.034 | 0.012623 |
| myristic acid | 0.023 | 0.008539 |
| palmitic acid ME | 0.014 | 0.005198 |
| palmitic acid | 0.514 | 0.190823 |
| alkane | 0.015 | 0.005569 |
| Linolenic acid | 0.074 | 0.027473 |
| Linoleic acid | 0.388 | 0.144045 |
| stearic acid | 3.135 | 1.163869 |
| Arachidonic acid | 0.022 | 0.008168 |
| CBD | 0.036 | 0.013365 |
| Cholesterol | 0.499 | 0.185254 |
| THC | 1.724 | 0.640035 |
| THCA | 83.172 | 30.87761 |
| CBG | 1.399 | 0.519379 |
| CBN | 3.537 | 1.313111 |
| b-sitosterol | 1.697 | 0.630011 |
| stigmasterol | 1.468 | 0.544995 |
| silyl | 1.184 | 0.43956 |
| alkane | 0.714 | 0.265073 |
| | | 37.125 |

Of note: all samples were introduced to GC/MS after silylation with 100 µL BSTFA with 1% TMCS.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Other References are Cited Throughout the Document

[1] Sartor R B. Mechanisms of disease: Pathogenesis of Crohn's disease and ulcerative colitis. Nat Rev Gastroenterol Hepatol. 2006; 3:390-407
[2] Sturm A, Dignass A U. Epithelial restitution and wound healing in inflammatory bowel disease. World J Gastroenterol. 2008; 14:348.
[3] D'Haens G R, Sartor R B, Silverberg M S, Petersson J, Rutgeerts P. Future directions in inflammatory bowel disease management. J Crohns Colitis. 2014; 8:726-734.
[4] Wright K, Duncan M, Sharkey K. Cannabinoid CB2 receptors in the gastrointestinal tract: A regulatory system in states of inflammation. Br J Pharmacol. 2008; 153:263-270.
[5] Schicho R, Storr M. Cannabis finds its way into treatment of Crohn's disease. Pharmacology. 2013; 93:1-3.
[6] Aizpurua-Olaizola O, Soydaner U, Öztürk E, Schibano D, Simsir Y, Navarro P, Etxebarria N, Usobiaga A. Evolution of the cannabinoid and terpene content during the growth of *Cannabis sativa* plants from different chemotypes. J Nat Prod. 2016; 79:324-331.
[7] Mechoulam R, Shani A, Edery H, Grunfeld Y. Chemical basis of hashish activity. Science. 1970; 169:611-612.
[8] Mechoulam R, Gaoni Y. Hashish-iv: The isolation and structure of cannabinolic cannabidiolic and cannabigerolic acids. Tetrahedron. 1965; 21:1223-1229.
[9] Mechoulam R, Parker L A, Gallily R. Cannabidiol: An overview of some pharmacological aspects. J Clin Pharmacol. 2002; 42:11S-19S.
[10] Greineisen W E, Turner H. Immunoactive effects of cannabinoids: Considerations for the therapeutic use of cannabinoid receptor agonists and antagonists. Int Immunopharmacol. 2010; 10:547-555.
[11] Romano B, Pagano E, Orlando P, Capasso R, Cascio M G, Pertwee R, Di Marzo V, Izzo A A, Borrelli F. Pure A 9-tetrahydrocannabivarin and a *Cannabis sativa* extract with high content in Δ9-tetrahydrocannabivarin inhibit nitrite production in murine peritoneal macrophages. Pharmacol Res. 2016; 113:199-208.
[12] Ihenetu K, Molleman A, Parsons M E, Whelan C J. Inhibition of Interleukin-8 release in the human colonic epithelial cell line HT-29 by cannabinoids. Eur J Pharmacol. 2003; 458:207-215.
[13] Ryberg E, Larsson N, Sjögren S, Hjorth S, Hermansson N O, Leonova J, Elebring T, Nilsson K, Drmota T, Greasley P. The orphan receptor GPR55 is a novel cannabinoid receptor. Br J Pharmacol. 2007; 152:1092-1101.
[14] Stančić A, Jandl K, Hasenöhrl C, Reichmann F, Marsche G, Schuligoi R, Heinemann A, Storr M, Schicho R. The GPR55 antagonist CID16020046 protects against intestinal inflammation. Neurogastroenterol Motil. 2015; 27:1432-1445.
[15] Storr M A, Keenan C M, Zhang H, Patel K D, Makriyannis A, Sharkey K A. Activation of the cannabinoid 2 receptor (CB2) protects against experimental colitis. Inflamm Bowel Dis. 2009; 15:1678-1685.
[16] Izzo A A, Camilleri M. Cannabinoids in intestinal inflammation and cancer. Pharmacol Res. 2009; 60:117-125.
[17] Naftali T, Lev L B, Yablecovitch D, Half E, Konikoff F M. Treatment of Crohn's disease with cannabis: An observational study. Isr Med Assoc J. 2011; 13:455-8.
[18] Naftali T, Schleider L B, Dotan I, Lansky E P, Benjaminov F S, Konikoff F M. Cannabis induces a clinical response in patients with Crohn's disease: a prospective placebo-controlled study. Clin Gastroenterol Hepatol. 2013; 11:1276-1280.
[19] Pagano E, Capasso R, Piscitelli F, Romano B, Parisi O A, Finizio S, Lauritano A, Di Marzo V, Izzo A A, Borrelli F. An Orally Active Cannabis Extract with High Content in Cannabidiol attenuates Chemically-induced Intestinal Inflammation and Hypermotility in the Mouse. Front Pharmacol. 2016; 7: 341.
[20] Hill T D, Cascio M G, Romano B, Duncan M, Pertwee R G, Williams C M, Whalley B J, Hill A J. Cannabidivarin-rich cannabis extracts are anticonvulsant in mouse and rat via a CB1 receptor-independent mechanism. Br J Pharmacol. 2013; 170:679-692.
[21] Russo E B. Taming THC: Potential cannabis synergy and phytocannabinoid-terpenoid entourage effects. Br J Pharmacol. 2011; 163:1344-1364.
[22] Smith R, Vaughan C. The decomposition of acidic and neutral cannabinoids in organic solvents. J Pharm Pharmacol. 1977; 29:286-290.
[23] Esposito G, Filippis D D, Cirillo C, Iuvone T, Capoccia E, Scuderi C, Steardo A, Cuomo R, Steardo L. Cannabidiol in inflammatory bowel diseases: A brief overview. Phytother Res. 2013; 27:633-636.
[24] Wang D, DuBois R N. The role of COX-2 in intestinal inflammation and colorectal cancer. Oncogene. 2010; 29:781-788.
[25] Castaneda F E, Walia B, Vijay-Kumar M, Patel N R, Roser S, Kolachala V L, Rojas M, Wang L, Oprea G, Garg P. Targeted deletion of metalloproteinase 9 attenuates experimental colitis in mice: Central role of epithelial-derived MMP. Gastroenterology. 2005; 129:1991-2008.
[26] Moreno-Sanz G. Can you pass the acid test? Critical review and novel therapeutic perspectives of δ9-tetrahydrocannabinolic acid a. Cannabis Cannabinoid Res. 2016; 1:124-130.
[27] Verhoeckx K C, Korthout H A, van Meeteren-Kreikamp A, Ehlert K A, Wang M, van der Greef J, Rodenburg R J, Witkamp R F. Unheated *Cannabis sativa* extracts and its major compound THC-acid have potential immunomodulating properties not mediated by CB 1 and CB 2 receptor coupled pathways. Int Immunopharmacol. 2006; 6:656-665.
[28] Ruhaak L R, Felth J, Karlsson P C, Rafter J J, Verpoorte R, Bohlin L. Evaluation of the cyclooxygenase inhibiting effects of six major cannabinoids isolated from *Cannabis sativa*. Biol Pharm Bull. 2011; 34:774-778.
[29] Kolho K-L, Sipponen T, Valtonen E, Savilahti E. Fecal calprotectin, MMP-9, and human beta-defensin-2 levels in pediatric inflammatory bowel disease. Int J Colorectal Dis. 2014; 29:43-50.
[30] Annaházi A, Molnár T, Farkas K, Rosztóczy A, Izbéki F, Gecse K, Inczefi O, Nagy F, Földesi I, Szűcs M. Fecal MMP-9: A new noninvasive differential diagnostic and activity marker in ulcerative colitis. Inflamm Bowel Dis. 2012; 19:316-320.

[31] El Miedany Y, Youssef S, Ahmed I, El Gaafary M. The gastrointestinal safety and effect on disease activity of etoricoxib, a selective COX-2 inhibitor in inflammatory bowel diseases. Am J Gastroenterol. 2006; 101:311-317.

[32] Xu L, Stevens J, Hilton M B, Seaman S, Conrads T P, Veenstra T D, Logsdon D, Morris H, Swing D A, Patel N L. COX-2 inhibition potentiates antiangiogenic cancer therapy and prevents metastasis in preclinical models. Sci Transl Med. 2014; 6:242ra84-242ra84.

[33] Romano B, Borrelli F, Pagano E, Cascio M G, Pertwee R G, Izzo A A. Inhibition of colon carcinogenesis by a standardized *Cannabis sativa* extract with high content of cannabidiol. Phytomedicine. 2014; 21:631-639.

[34] Martínez-Martínez E, Gómez I, Martín P, Sánchez A, Román L, Tejerina E, Bonilla F, Merino A G, de Herreros A G, Provencio M, García J M. Cannabinoids receptor type 2, CB2, expression correlates with human colon cancer progression and predicts patient survival. Oncoscience. 2015; 2:131.

What is claimed is:

1. A method of treating an inflammatory disease in a subject in need thereof, the method comprising administering to the subject a therapeutically effective amount of a liquid chromatography fraction of a cannabis extract containing components

| Compounds | % |
| --- | --- |
| D-Limonene | 0.097 |
| Glycerol | 0.086 |
| β-Caryophyllene | 0.103 |
| Humulene | 0.03 |
| malic acid | 0.035 |
| α-Farnesene | 0.034 |
| myristic acid | 0.023 |
| palmitic acid ME | 0.014 |
| palmitic acid | 0.514 |
| alkane | 0.015 |
| Linolenic acid | 0.074 |
| Linoleic acid | 0.388 |
| stearic acid | 3.135 |
| Arachidonic acid | 0.022 |

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 1
attgaccaga gcaggcagat                                                   20

<210> SEQ ID NO 2
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 2
caggatacag ctccacagca                                                   20

<210> SEQ ID NO 3
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 3
ttgacagcga caagaagtgg                                                   20

<210> SEQ ID NO 4
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 4
tcacgtcgtc cttatgcaag                                                   20
```

-continued

| Compounds | % |
|---|---|
| CBD | 0.036 |
| Cholesterol | 0.499 |
| THC | 1.724 |
| THCA | 83.172 |
| CBG | 1.399 |
| CBN | 3.537 |
| b-sitosterol | 1.697 |
| stigmasterol | 1.468 |
| silyl | 1.184 |
| alkane | 0.714, | thereby treating the inflammatory disease in the subject.

2. The method of claim 1, wherein said liquid chromatography comprises high pressure liquid chromatography (HPLC).

3. The method of claim 1, wherein said liquid chromatography is performed on a reverse stationary phase.

4. The method of claim 1, wherein said extract is an ethanol extract.

5. The method of claim 1, wherein said inflammatory disease is an inflammatory bowel disease (IBD).

6. The method of claim 5, wherein said IBD is selected from the group consisting of ulcerative colitis and Crohn's disease.

7. A liquid chromatography fraction of a cannabis extract comprising components

| Compounds | % |
|---|---|
| D-Limonene | 0.097 |
| Glycerol | 0.086 |
| β-Caryophyllene | 0.103 |
| Humulene | 0.03 |
| malic acid | 0.035 |
| α-Farnesene | 0.034 |
| myristic acid | 0.023 |
| palmitic acid ME | 0.014 |
| palmitic acid | 0.514 |
| alkane | 0.015 |
| Linolenic acid | 0.074 |
| Linoleic acid | 0.388 |
| stearic acid | 3.135 |
| Arachidonic acid | 0.022 |
| CBD | 0.036 |
| Cholesterol | 0.499 |
| THC | 1.724 |
| THCA | 83.172 |
| CBG | 1.399 |
| CBN | 3.537 |
| b-sitosterol | 1.697 |
| stigmasterol | 1.468 |
| silyl | 1.184 |
| alkane | 0.714. |

8. The fraction of claim 7, wherein said liquid chromatography comprises high pressure liquid chromatography (HPLC).

9. The fraction of claim 7, wherein said liquid chromatography is performed on a reverse stationary phase.

10. The fraction of claim 7, wherein said extract is an ethanol extract.

* * * * *